(12) United States Patent
Kahn et al.

(10) Patent No.: US 10,092,568 B2
(45) Date of Patent: *Oct. 9, 2018

(54) CBP/CATENIN ANTAGONISTS FOR ENHANCING ASYMMETRIC DIVISION OF SOMATIC STEM CELLS

(71) Applicant: University of Southern California, Los Angeles, CA (US)

(72) Inventors: Michael Kahn, Altadena, CA (US); Jia-Ling Teo, Altadena, CA (US); Michael McMillan, Alhambra, CA (US); Yi Zhao, South Pasadena, CA (US); Yongfeng Wu, San Gabriel, CA (US)

(73) Assignee: University of Southern California, Los Angeles, CA (US)

( * ) Notice: Subject to any disclaimer, the term of this patent is extended or adjusted under 35 U.S.C. 154(b) by 1211 days.

This patent is subject to a terminal disclaimer.

(21) Appl. No.: 13/895,220

(22) Filed: May 15, 2013

(65) Prior Publication Data

US 2013/0280233 A1     Oct. 24, 2013

Related U.S. Application Data

(63) Continuation of application No. PCT/US2011/061062, filed on Nov. 16, 2011.

(60) Provisional application No. 61/545,033, filed on Oct. 7, 2011, provisional application No. 61/414,334, filed on Nov. 16, 2010, provisional application No. 61/414,348, filed on Nov. 16, 2010.

(51) Int. Cl.
| | | |
|---|---|---|
| *A61K 31/519* | (2006.01) | |
| *A61K 38/50* | (2006.01) | |
| *C07D 487/04* | (2006.01) | |
| *A61K 31/4375* | (2006.01) | |
| *A61K 31/167* | (2006.01) | |
| *A61K 31/4985* | (2006.01) | |
| *A61K 31/506* | (2006.01) | |
| *A61K 31/5575* | (2006.01) | |
| *A61K 31/58* | (2006.01) | |
| *A61K 45/06* | (2006.01) | |
| *A61K 31/573* | (2006.01) | |

(52) U.S. Cl.
CPC .......... *A61K 31/519* (2013.01); *A61K 31/167* (2013.01); *A61K 31/4375* (2013.01); *A61K 31/4985* (2013.01); *A61K 31/506* (2013.01); *A61K 31/5575* (2013.01); *A61K 31/573* (2013.01); *A61K 31/58* (2013.01); *A61K 38/50* (2013.01); *A61K 45/06* (2013.01); *C07D 487/04* (2013.01)

(58) Field of Classification Search
CPC .. C07D 487/04; A61K 31/519; A61K 31/167; A61K 31/4375; A61K 31/4985; A61K 31/506; A61K 31/5575; A61K 31/573; A61K 31/58; A61K 38/50; A61K 45/06
See application file for complete search history.

(56) References Cited

U.S. PATENT DOCUMENTS

| | | |
|---|---|---|
| 5,262,321 A | 11/1993 | Livingston et al. |
| 5,658,784 A | 8/1997 | Eckner et al. |
| 6,063,583 A | 5/2000 | Montminy |
| 6,413,963 B2 | 7/2002 | Kahn et al. |
| 6,762,185 B1 | 7/2004 | Kahn et al. |
| 7,531,320 B2 | 5/2009 | Kahn et al. |
| 7,563,825 B1 | 7/2009 | Kahn |
| 2004/0072831 A1 | 4/2004 | Moon et al. |
| 2005/0059628 A1 | 3/2005 | Kahn et al. |
| 2005/0250780 A1 | 11/2005 | Qabar |
| 2005/0280780 A1 | 12/2005 | Matsumoto et al. |

(Continued)

FOREIGN PATENT DOCUMENTS

| | | |
|---|---|---|
| EP | 0267878 A1 | 5/1988 |
| JP | 63-135384 A | 6/1988 |

(Continued)

OTHER PUBLICATIONS

Abraham et al., "p300, and p300-associated proteins, are components of TATA-binding protein (TBP) complexes" Oncogene, 8(6), 1993, pp. 1639-1647.

Adams et al., "3,400 new expressed sequence tags identify diversity of transcripts in human brain," Nature Genetics, 4, 1993, pp. 256-267.

Al-Hajj et al., "Therapeutic implications of cancer stem cells," Current Opinion in Genetics & Development, 14(1), Feb. 2004, pp. 43-47.

(Continued)

*Primary Examiner* — Kortney L. Klinkel
*Assistant Examiner* — Ibrahim D Bori
(74) *Attorney, Agent, or Firm* — Barry L. Davison; Davis Wright Tremaine LLP

(57) ABSTRACT

Provided are: methods for treating aging or an age-related condition, symptom or disease; methods for stimulating hair growth, regrowth or pigmentation (or preventing hair loss); methods for increasing the expression of an adenosine receptor in dermal cells (in combination with hair growth); methods for treating a condition or disease of the skin or at least one symptom thereof, including cosmetic treatment (e.g., wrinkles, hyperpigmentation, redness, rosacea, dryness, cracking, loss of firmness, loss of elasticity, thinning, and loss of vibrance). The methods comprise administering a sufficient amount of a CBP/catenin (e.g., CBP/β-catenin) antagonist as disclosed, and particularly wherein administration is in an amount and manner sufficient to provide for increasing the number of asymmetric renewing divisions relative to, or at the expense of symmetric divisions in relevant somatic stem cell population. In particular aspects, the CBP/catenin (e.g., CBP/β-catenin) antagonist comprises an alkyl and/or fatty acid ester derivative thereof as disclosed herein.

19 Claims, 18 Drawing Sheets

(56) References Cited

U.S. PATENT DOCUMENTS

| | | |
|---|---|---|
| 2006/0084655 A1 | 4/2006 | Moon |
| 2006/0094655 A1 | 5/2006 | Guyon et al. |
| 2007/0021425 A1 | 1/2007 | Moon et al. |
| 2007/0021431 A1 | 1/2007 | Moon et al. |
| 2007/0043052 A1 | 2/2007 | Moon et al. |
| 2007/0128669 A1 | 6/2007 | Kahn |
| 2008/0009500 A1 | 1/2008 | Kahn |
| 2010/0120758 A1 | 5/2010 | Moon et al. |
| 2010/0222303 A1 | 9/2010 | Moon et al. |
| 2010/0240662 A1 | 9/2010 | Moon et al. |
| 2011/0311534 A1 | 12/2011 | Ernst |

FOREIGN PATENT DOCUMENTS

| | | |
|---|---|---|
| JP | 11-501006 A | 1/1999 |
| JP | 2002-500880 A | 1/2002 |
| JP | 2003-533504 A | 11/2003 |
| JP | 2005-517731 A | 6/2005 |
| JP | 2008-533155 A | 8/2008 |
| JP | 2009-517085 A | 4/2009 |
| JP | 2010-504081 A | 2/2010 |
| JP | 2014509298 A | 4/2014 |
| WO | 1996/008228 A2 | 3/1996 |
| WO | 1999/037753 A1 | 7/1999 |
| WO | 2001/087824 A2 | 11/2001 |
| WO | 2003/070675 A2 | 8/2003 |
| WO | WO-2006101858 A1 | 9/2006 |
| WO | WO-2007139346 A1 | 12/2007 |
| WO | WO-2009051399 A2 | 4/2009 |
| WO | WO-2010044485 A1 | 4/2010 |
| WO | WO-2010124365 A1 | 11/2010 |
| WO | WO-2010128685 A1 | 11/2010 |
| WO | WO-2012068299 A2 | 5/2012 |
| WO | WO-2012115286 A1 | 8/2012 |

OTHER PUBLICATIONS

An et al., "Direct Association of p300 with Unmodified H3 and H4 N Termini Modulates p300-dependent Acetylation and Transcription of Nucleosomal Templates," The Journal of Biological Chemistry, 278(3), Jan. 17, 2003, pp. 1504-1510.

Angers et al., "Proximal events in Wnt signal transduction," Nature Reviews Molecular Cell Biology, 10, Jul. 2009, pp. 468-477.

Batlle et al., "β-catenin and TCF mediate cell positioning in the intestinal epithelium by controlling the expression of EphB/ephrinB," Cell, 111(2), Oct. 18, 2002, pp. 251-263.

Beaudoin et al., "Hairless triggers reactivation of hair growth by promoting Wnt signaling," Proceedings of the National Academy of Sciences of the United States of America, 102(41), Oct. 11, 2005, pp. 14653-14658.

Bedford et al., "Target gene context influences the transcriptional requirement for the KAT3 family of CBP and p300 histone acetyltransferases," Epigenetics, 5(1), 2010, pp. 9-15.

Beildeck et al., "Control of TCF-4 expression by VDR and vitamin D in the mouse mammary gland and colorectal cancer cell lines," PLoS One, 4(11), e7872, Nov. 17, 2009, 14 pages.

Borrelli et al., "Adenovirus-2 E1A products repress enhancer-induced stimulation of transcription," Nature, 312, Dec. 1984, pp. 608-612.

Botchkareva et al., "Survivin in the Human Hair Follicle" Journal of Investigative Dermatology, 127, 2007, pp. 479-482.

Brack et al., "Increased Wnt signaling during aging alters muscle stem cell fate and increases fibrosis," Science, 317(5839), Aug. 10, 2007, pp. 807-810.

Braun et al., "Inhibition of muscle differentiation by the adenovrious E1a protein: repression of the transcriptional activating funcntion of the HLH protein Myf-5," Genes & Development, 6, 1992, pp. 888-902.

Bultje et al., "Mammalian Par3 regulates progenitor cell asymmetric division via notch signaling in the developing neocortex," Neuron, 63(2), Jul. 30, 2009, pp. 189-202.

Cairns et al., "Mutation selection and the natural history of cancer," Nature, 255, May 15, 1975, pp. 197-200.

Caruso et al., "Regulation of MyoD gene transcription and protein function by the transforming domains of the adenovirus E1A oncoprotein," Oncogene, 8(2), 1993, pp. 267-278.

Cho et al., "Cardamonin suppresses melanogenisis by inhibition of Wnt/beta-catenin signalling," Biochemical and Biophysical Research Communications, 390(3), Dec. 18, 2009, pp. 500-505, Academic Press Inc., Orlando, FL, US.

Chrivia et al., "Phosphorylated CREB binds specifically to the nuclear protein CBP," Nature, 365, 1993, pp. 855-859.

Cissé et al., "Reversing EphB2 depletion rescues cognitive functions in Alzheimer model," Nature, 469, Jan. 6, 2011, pp. 47-52.

Creyghton et al., "PR72, a novel regulator of Wnt signaling required for Naked cuticle function," Genes & Development, 19, 2005, pp. 376-386.

Davis et al., "ZD6126: A Novel Vascular-targeting Agent That Causes Selective Destruction of Tumor Vasculature," Cancer Research, 62(24), Dec. 15, 2002, pp. 7247-7253.

De Lau et al., "Wnt signaling in the normal intestine and colorectal cancer," Frontiers in Bioscience, 12, 2007, pp. 471-491.

Eckner et al., "Molecular cloning and functional analysis of the adenovirus E1A-associated 300-kD protein (p300) reveals a protein with properties of a transcriptional adaptor," Genes & Development, 8(8), 1994, pp. 869-884.

Emami et al., "A small molecule inhibitor of beta-catenin/CREB-binding protein transcription [corrected]," Proceedings of the National Academy of Sciences of the United States of America, 101(34), Aug. 24, 2004, pp. 12682-12687.

Extended European Search Report issued by the European Patent Office in EP Patent Application No. 118417674, dated Apr. 29, 2015, 9 pages.

Extended European Search Report issued by the European Patent Office in EP Patent Application No. 128389335, dated Apr. 28, 2015, 5 pages.

Fathke et al., "Wnt signaling induces epithelial differentiation during cutaneous wound healing," BMC Cell Biology, 7(4), Jan. 20, 2006, 9 pages.

Fleisher et al., "Improved oral drug delivery: solubility limitations overcome by the use of prodrugs," Advanced Drug Delivery Reviews, 19(2), May 22, 1996, pp. 115-130.

Foley et al., "Further case of Rubinstein Taybi syndrome due to a deletion in EP300," American Journal of Medical Genetics Part A, 149A(5), May 2009, pp. 991-1000.

Giehl et al., "Microevironmental regulation of E-cadherin-mediated adherens junctions," Frontiers in Bioscience, Landmark, 13, May 1, 2008, pp. 3975-3985.

Golik et al., "Synthesis and antitumor evaluation of paclitaxel phosphonooxymethyl ethers: a novel class of water soluble paclitaxel pro-drugs," Bioorganic & Medicinal Chemistry Letters, 6(15), Aug. 6, 1996, pp. 1837-1842.

Gudjonsson et al (The Journal of Investigative Dermatology 130:1849-1859, 2010).

Gusterson et al., "The Transcriptional Co-activators CREB-binding Protein (CBP) and p300 Play a Critical Role in Cardiac Hypertrophy That Is Dependent on Their Histone Acetyltransferase Activity," The Journal of Biological Chemistry, 278(9), Feb. 28, 2003, pp. 6838-6847.

Harlow et al., "Associated of Adenovirus Early-Region 1A Proteins with Cellular Polypeptides," Molecular and Cellular Biology, 6(5), May 1986, 1579-1589.

Hasegawa et al., "Wnt signaling orchestration with a small molecule DYRK inhibitor provides long-term xeno-free human pluripotent cell expansion," Stem Cells Translational Medicine, 1(1), Jan. 2012, pp. 18-28.

Henderson, Jr. et al., "Inhibition of Wnt/β-catenin/CREB binding protein (CBP) signaling reverses pulmonary fibrosis," Proceedings of the National Academy of Sciences of the United States of America, 107(32), Aug. 10, 2010, pp. 14309-14314.

Hernandez et al., "Functional coupling between the extracellular matrix and nuclear lamina by Wnt signaling in progeria," Developmental Cell, 19(3), Sep. 14, 2010, pp. 413-425.

(56) References Cited

OTHER PUBLICATIONS

Hirota et al., "Smad2 functions as a co-activator of canonical Wnt/beta-catenin signaling pathway independent of Smad4 through histone acetyltransferase activity of p300," Cellular Signaling, 20(9), Sep. 2008, pp. 1632-1641.
Howe et al., "Retinoblastoma growth suppressor and a 300-kDa protein appear to regulate cellular DNA synthesis," Proceedings of the National Academy of Sciences of the United States of America, 87(15), Aug. 1, 1990, pp. 5883-5887.
Huelsken et al., "The Wnt signalling pathway," Journal of Cell Science, 115, 2002, pp. 3977-3978.
Inestrosa et al., "Emerging roles of Wnts in the adult nervous system," Natura Reviews Neuroscience, 11, Feb. 2010, pp. 77-86.
International Search Report and Written Opinion issued in International Patent Application No. PCT/US2011/061062, dated May 9, 2012, 5 pages.
International Search Report and Written Opinion issued in International Patent Application No. PCT/US2012/038003, dated Dec. 3, 2012, 10 pages.
Jeannet et al., "Long-term, multilineage hematopoiesis occurs in the combined absence of β-catenin and gamma-catenin," Blood, 111(1), Jan. 1, 2008, pp. 142-149.
Kawasaki et al., "Distinct roles of the co-activators p300 and CBP in retinoic-acid-induced F9-cell differentiation," 393, May 21, 1998, pp. 284-289.
Kelly et al., "β-catenin enhances Oct-4 activity and reinforces pluripotency through a TCF-independent mechanism," Cell Stem Cell, 8(2), Feb. 4, 2011, pp. 214-227.
Kim et al., "GSK-3 is a master regulator of neural progenitor homeostasis," Nature Neuroscience, 12, 2009, pp. 1390-1397.
Kim et al., "The gamma catenin/CBP complex maintains survivin transcription in β-catenin deficient/depleted cancer cells," Current Cancer Drug Targets, 11(2), Feb. 2011, pp. 213-225.
Kohn et al., "Wnt and calcium signaling: β-catenin-independent pathways," Cell Calcium, 38(3-4), Sep.-Oct. 2005, pp. 439-446.
Kumar et al., "Preferential induction of EphB4 over EphB2 and its implication in colorectal cancer progression," Cancer Research, 69(9), May 1, 2009, pp. 3736-2745.
Kung et al., "Gene dose-dependent control of hematopoiesis and hematologic tumor suppression by CBP," Genes & Development, 14, 2000, pp. 272-277.
Kwon et al., "PKG inhibits TCF signaling in colon cancer cells by blocking β-catenin expression and activating FOXO4," Oncogene, 29, 2010, pp. 3423-3434.
Labarge et al., "The difficulty of targeting cancer stem cell niches," Clinical Cancer Research, 16(12), Jun. 15, 2010, pp. 3121-3129.
Li et al., "Minoxidil-Induced Hair Growth is Mediated by Adenosine in Cultured Dermal Papilla Cells: Possible Involvement of Sulfonylurea Receptor 2B as a Target of Minoxidil," Journal of Investigative Dermatology, 117(6), Dec. 2001, pp. 1594-1600.
Lindvall et al., "Wnt signaling, stem cells, and the cellular origin of breast cancer," Stem Cell Reviews, 3(2), 2007, pp. 157-168.
Liu et al., "Augmented Wnt signaling in a mammalian model of accelerated aging," Science, 317(5839), Aug. 10, 2007, pp. 803-806.
Lloyd et al., "Transformation suppressor activity of a Jun transcription factor lacking its activation domain," Nature, 352, Aug. 15, 1991, pp. 635-638.
Logan et al., "The Wnt signaling pathway in development and disease," Annual Review of Cell and Developmental Biology, 20, 2004, pp. 781-810.
Lyubimova et al., "Neural Wiskott-Alrich syndrome protein modulates Wnt signaling and is required for hair follical cycling in mice," The Journal of Clinical Investigation, 120(2), Feb. 1, 2010, pp. 446-456.
Ma et al., "Differential roles for the coactivators CBP and p300 on TCF/β-catenin-mediated survivin gene expression," Oncogene, 24, 2005, pp. 3619-3631.

Mai et al., "Cloning of the human homolog of conductin (AXIN2), a gene mapping to chromosome 17q23-24," Genomics, 55(3), Feb. 1999, pp. 341-344.
Malhotra et al., "Wnt-related molecules and signaling pathway equilibrium in hematopoiesis," Cell Stem Cell, 4(1), Jan. 9, 2009, pp. 27-36.
Mani et al., "The epithelial-mesenchymal transition generates cells with properties of stem cells," Cell, 133(4), May 16, 2008, pp. 704-715.
Marson et al., "Wnt signaling promotes reprogramming of somatic cells to pluripotency," Cell Stem Cell, 3(2), Aug. 7, 2008, pp. 132-135.
McMillan et al., "Investigating Wnt Signaling, a Chemogenomic Safari," Drug Discovery Today, 10(21), Nov. 1, 2005, pp. 1467-1474.
Merchant et al., "Targeting Hedgehog—a cancer stem cell pathway," Clinical Cancer Research, 16(12), Jun. 15, 2010, pp. 3130-3140.
Miyabayashi et al., "Wnt/β-catenin/CBP signaling maintains long-term murine embryonic stem cell pluripotency," Proceedings of the National Academy of Sciences of the United States of America, 104(13), Mar. 27, 2007, pp. 5668-5673.
Monga , "Wnt/β-catenin signaling in liver metabolism and cancer," The International Journal of Biochemistry & Cell Biology, 43(7), Jul. 2011, pp. 1021-1029.
Moon et al., "The Promise and Perils of Wnt Signalling Through β-Catenin," Science, 296(5573), May 31, 2002, pp. 1644-1646.
Moran et al., "Interactions between cell growth-regulating domains in the products of the adenovirus E1A oncogene," Molecular and Cellular Biology, 8(4), Apr. 1988, pp. 1756-1764.
Morin, "β-catenin signaling and cancer," Bioessays, 21(12), Dec. 1999, pp. 1021-1030.
Nagahata et al., "Amplification, up-regulation and over expression of DVL-1, the human counterpart of the *Drosophila* disheveled gene, in primary breast cancers," Cancer Science, 94(6), Jun. 2003, pp. 515-518.
Nakamura et al., "Epithelial-mesenchymal transition in the skin," Journal of Dermatological Science, 61(1), Jan. 1, 2011, pp. 7-13.
Nemeth et al., "β-Catenin expression in the bone marrow microenvironment is required for long-term maintenance of primitive hematopoietic cells," Stem Cells, 27(5), May 2009, pp. 1109-1119.
Otero et al., "β-catenin signaling is required for neural differentiation of embryonic stem cells," Development, 131, 2004, pp. 3545-3557.
Oving et al., "Molecular causes of colon cancer," European Journal of Clinical Investigation, 32(6), Jun. 2002, pp. 448-457.
Pannuti et al., "Targeting Notch to target cancer stem cells," Clinical Cancer Research, 16(12), Jun. 15, 2010, pp. 3141-3152.
Radich et al., "Gene expression changes associated with progression and response in chronic myeloid leukemia," Proceedings of the National Academy of Sciences of the United States of America, 103(8), Feb. 21, 2006, pp. 2794-2799.
Rebel et al., "Distinct roles for CREB-binding protein and p300 in hematopoietic stem cell self-renewal," Proceedings of the National Academy of Sciences of the United States of America, 99(23), Nov. 12, 2002, pp. 14789-14794.
Ribgy et al., "Three in One and One in Three: It all Depends on TBP," Cell, 72(1), Jan. 15, 1993, pp. 7-10.
Rikitake et al., DNA-Binding Properties of the E1A-Associated 300-Kilodalton Protein, Molecular and Cellular Biology, 12(6), Jun. 1992, pp. 2826-2836.
Ring et al., "Targeting β-cetenin/CBP interaction in breast cancer," Journal of Clinical Oncology, 29(15 _suppl), 2011 ASCO Annual Meeting Abstracts Part 1, May 2011, Abstract No. 10516.
Roh et al., "Gene expression profiling of breast cancers with emphasis of β-catenin regulation," Journal of Korean Medical Science, 19(2), Apr. 2004, pp. 275-282.
Roth et al., "Differential role of p300 and CBP acetyltransferase during myogenesis: p300 acts upstream of MyoD and Myf5," The EMBO Journal, 22(19), 2003, pp. 5186-5196.
Sakanaka et al., Recent Progress in Hormone Research, 55, 2000, pp. 225-236.

(56) References Cited

OTHER PUBLICATIONS

Sato et al., "Maintenance of pluripotency in human and mouse embryonic stem cells through activation of Wnt signaling by a pharmacological GSK-3-specific inhibitor," Nature Medicine, 10, 2004, pp. 55-63.

Schenke-Layland et al., "Recapitulation of the embryonic cardiovascular progenitor cell niche," Biomaterials, 32(11), Apr. 2011, pp. 2748-2756.

Schneider et al., "Mutational Analysis of the Adenovirus E1 a Gene: the role of transcriptional regulation in transformation" The EMBO Journal, 6(7), 1987, pp. 2053-2060.

Stein et al., "Analysis of E1A-Mediated Growth Regulation Functions: Binding of the 300-Kilodalton Cellular Product Correlates with E1A Enhancer Repression Function and DNA Synthesis-Inducing Activity," Journal of Virology, 64(9), Sep. 1990, pp. 4421-4427.

Szeto et al., "Overexpression of the retinoic acid-responsive gene Stra6 in human cancers and its synergistic induction by Wnt-1 and retinoic acid," Cancer Research, 61, May 15, 2001, pp. 4197-4205.

Takemaru et al., "The Transcriptional Coactivator CBP Interacts with β-Catenin to Activate Gene Expression," Journal of Cell Biology, 149(2), Apr. 17, 2000, pp. 249-254.

Tanaka et al., "Abnormal skeletal patterning in embryos lacking a single Cbp allele: a partial similarity with Rubinstein-Taybi syndrome," Proceedings of the National Academy of Science of the United States of America, 94(19), Sep. 16, 1997, pp. 10215-10220.

Teo et al., "Specific inhibition of CBP/beta-catenin interaction rescues defects in neuronal differentiation caused by a presenilin-1 mutation," Proceedings of the National Academy of Sciences of the United States of America, 102(34), Aug. 23, 2005, pp. 12171-12176.

Thompson et al., "Hairless and Wnt Signaling: Allies in Epithelial Stem Cell Differentiation," Cell Cycle, 5(17), Sep. 1, 2006, pp. 1913-1917.

Ugai et al., "The coactivators p300 and CBP have different functions during the differentiation of F9 cells," Journal of Molecular Medicine, 77(6), Jun. 1999, pp. 481-494.

Ugolini et al., "Differential expression assay of chromosome arm 8p genes identifies Frizzled-related (FRP1/FRZB) and Fibroblast Growth Factor Receptor 1 (FGFR1) as candidate breast cancer genes," Oncogene, 18, 1999, pp. 1903-1910.

Van Dam et al., "Differential Effects of the Adenovirus E1A Oncogene on Members of the AP-1 Transcription Factor Family," Molecular and Cellular Biology, 10(11), Nov. 1990, pp. 5857-5864.

Velcich et al., "Adenovirus E1 a proteins repress transcription from the SV40 early promoter," Cell, 40(3), Mar. 1985, pp. 705-716.

Wang et al., "E1A Induces Phosphorylation of the Retino-blastoma Protein Independently of Direct Physical Association between the E1A and Retinoblastoma Products,", Molecular and Cellular Biology, 11(8), Aug. 1991, pp. 4253-4265.

Weinmann et al., "Identification of unknown target genes of human transcription factors using chromatin immunoprecipitation," Methods, 26(1), Jan. 2, 2002, pp. 37-47.

Wend et al., "Wnt signaling in stem and cancer cells," Seminars in Cell and Developmental Biology, 21(8), Oct. 1, 2010, pp. 855-863, Academic Press, GB.

Wend et al., "Wnt/β-catenin signalling induces MLL to create epigenetic changes in salivary gland tumours," The EMBO Journal, 32(14), published online Jun. 4, 2013, pp. 1977-1989.

Whyte et al., "Cellular Targets for Transformation by the Adenovrius E1A Proteins" Cell, 56(1), Jan. 1989, pp. 67-75.

Wodarz et al., "Mechanisms of Wnt Signalling in Development," Annual Review of Cell and Developmental Biology, 14, Nov. 1998, pp. 59-88.

Yaciuk et al., "Analysis with Specific Polyclonal Antiserum Indicates that the E1A-Associated 300-kDa Product is a Stable Nuclear Phosphoprotein That Undergoes Cell Cycle Phase-Specific Modification," Molecular and Cellular Biology, 11(11), Nov. 1991, pp. 5389-5397.

Yamauchi et al., "Increased insulin sensitivity despite lipodystrophy in Crebbp heterozygous mice," Nature Genetics, 30, 2002, pp. 221-226.

Yao et al., "Gene dosage-dependent embryonic development and proliferation defects in mice lacking the transcriptional integrator p300," Cell, 93(3), May 1, 1998, pp. 361-372.

Yee et al., "Detection of cellular proteins associated with human adenovirus type 5 early region 1A polypeptides" Virology, 147(1), Nov. 1985, pp. 142-153.

Yilmaz et al., "Pten dependence distinguishes haematopoietic stem cells from leukaemia-initiating cells," Nature, 441, May 25, 2006, pp. 475-482.

Yong et al. "Wnt Signal Transduction Pathways and Hair Follicle Stem Cells," Journal of Biomedical Engineering, 27(4), Aug. 2010, pp. 945-948.

Zechner et al., "β-Catenin signals regulate cell growth and the balance between progenitor cell expansion and differentiation in the nervous system," Developmental Biology, 258(2), Jun. 15, 2003, pp. 406-418.

Zeng et al., "Naked cuticle encodes an inducible antagonist of Wnt signalling," Nature, 403, Feb. 17, 2000, pp. 789-795.

Zerler et al., "Different functional domains of the adenovirus E1A gene are involved in regulation of host cell cycle products," Molecular and Cellular Biology, 7(2), Feb. 1987, pp. 821-829.

Zhou et al., "Biological features of Wnt pathway in the development and regenerative repair of skin," Chinese Journal of Clinical Rehabilitation, 8(29), Oct. 15, 2009, pp. 6472-6473.

Cairns, J., "Cancer and the Immortal Strand Hypothesis," Genetics 174:1069-1072, Nov. 2006.

Japanese Office Action dated Aug. 25, 2016, issued in Japanese Patent Application No. 2013-539987, filed Nov. 16, 2011, 5 pages.

Larsen, C.S., and J. Østergaard, "Textbook of Drug Design and Discovery," 3rd ed., Taylor & Francis, New York, NY, 2002, Chapter 14 "Design and Application of Prodrugs," pp. 460-514.

CBP/CATENIN ANTAGONISTS FOR ENHANCING ASYMMETRIC DIVISION OF SOMATIC STEM CELLS

CROSS-REFERENCE TO RELATED APPLICATIONS

The present application is a continuation of International Patent Application Serial No. PCT/US2011/061062, filed 16 Nov. 2011 and entitled "CBP/CATENIN ANTAGONISTS FOR ENHANCING ASYMMETRIC DIVISION OF SOMATIC STEM CELLS," which claims the benefit of priority to U.S. Provisional Patent Application Ser. Nos. 61/545,033 filed 7 Oct. 2011 and entitled "COMPOSITIONS COMPRISING CBP/CATENIN ANTAGONISTS FOR USE IN MODULATION OF SYMMETRIC VERSUS ASYMMETRIC DIVISION FOR TREATING AGING AND AGING-RELATED CONDITIONS," 61/414,334 filed 16 Nov. 2010 and entitled "COMPOSITIONS COMPRISING CBP/CATENIN ANTAGONISTS FOR USE IN PROMOTING HAIR REGROWTH AND/OR PREVENTING OR RETARDING HAIR LOSS," and 61/414,348 filed 16 Nov. 2010 and entitled "COMPOSITIONS COMPRISING CBP/CATENIN ANTAGONISTS FOR USE IN COSMETICS AND FOR TREATING DERMATOLOGICAL DISORDERS," all of which are incorporated herein by reference in their entirety.

FIELD OF THE INVENTION

Particular aspects relate generally to aging, and more particularly to the use of CBP/Catenin (e.g., CBP/β-catenin) antagonists (e.g., ICG-001, and alkyl and fatty acid ester derivatives thereof, and other compounds disclosed herein) in modulation of symmetric versus asymmetric division for treating aging and aging-related conditions (e.g., wrinkles, hyperpigmentation, dryness, redness, cracking, rosacea, firmness, elasticity, thickness, scarring, appearance). Additional aspects relate generally to the use of said CBP/Catenin (e.g., CBP/β-catenin) antagonists in treating skin related diseases (e.g., wounds, acne, sun damage, effects of aging, treatment of latent infection (e.g., HSV, HPV), viral clearance (epidermal and mucosal tissue), ulcers (diabetic and others), burns, atopic dermatitis, psoriasis, age-related skin conditions including wrinkles, hyperpigmentation, redness, rosacea, dryness, cracking, loss of firmness, loss of elasticity, thinning, and loss of vibrance, etc.) and/or for cosmetic (skin and/or hair) purposes, and in particular aspects for promoting hair growth and/or regrowth and/or pigmentation, and preventing or retarding hair loss (e.g., age-related hair loss or loss of pigmentation). Additional aspects relate to method for increasing adenosine receptor levels in in dermal cells, preferably dermal papilla cells, to facilitate hair growth. Adjunctive and combination therapy embodiments are encompassed.

BACKGROUND OF THE INVENTION

The decision to divide asymmetrically or symmetrically may be the major fundamental intrinsic difference between normal stem and cancer stem cells. The decision to utilize either CBP/catenin or p300/catenin driven transcription, i.e. to divide symmetrically or asymmetrically, appears to be an extremely fundamental event as it is already critical even at the 8-cell stage of embryogenesis. The ultimate decision for a cell to retain potency or initiate differentiation is dependent upon numerous inputs including the activation of different growth factors, cytokines, and hormones and the subsequent activation of different signal transduction complexes and kinase cascades, nutrient levels, oxygen levels, genetic mutations, adhesion to substratum. In the end these multiple pathways must be integrated and funneled down into a simple decision point, i.e., a yes/no binary decision. While it is known how to pharmacologically manipulate the balance of differential catenin coactivator usage (i.e., catenin/CBP versus catenin/p300) in stem/progenitor cell populations, understanding how a cell reads the enormously complex array of information from its environment to arrive at an eventual 0/1 binary decision remains to be understood.

SUMMARY OF THE INVENTION

According to particular aspects, as disclosed herein, the equilibrium between CBP-mediated and p300-mediated catenin transcription plays a central role in decision to divide asymmetrically or symmetrically by integrating numerous inputs including the activation of different growth factors, cytokines, and hormones and the subsequent activation of different signal transduction complexes and kinase cascades, nutrient levels, oxygen levels, genetic mutations, adhesion to substratum.

CBP/catenin (e.g. beta and gamma) antagonists function by regulating human endogenous stem cells and/or surrounding cell function. Based on animal toxicity studies, and as recognized in the art, these compounds are extremely safe at effective dose levels. Since treating aging and aging-related conditions may require long-term administration, a large safety margin is optimal to physicians and patients alike.

According to particular aspects, CBP/catenin (e.g., CBP/β-catenin) antagonists can be used for modulating symmetric versus asymmetric stem cell division for treating aging and aging-related conditions.

Particular aspects provide a method for treating aging or a disease of aging or at least one condition or symptom thereof, comprising administering to a subject in need thereof an amount of a CBP/catenin (e.g., CBP/β-catenin) antagonist sufficient for increasing the number of asymmetric renewing divisions at the expense of symmetric divisions in the stem cell population, wherein a method for treating aging or a disease of aging or at least one symptom thereof is afforded.

Additional aspects provide a method for treating hair loss (e.g., preventing hair loss and/or promoting hair growth or regrowth and/or pigmentation (e.g., in aging subjects), comprising administering (e.g., topically or otherwise) to a subject in need thereof an amount of a CBP/catenin (e.g., CBP/β-catenin) antagonist sufficient for increasing the number of symmetric renewing divisions at the expense of symmetric divisions in the relevant stem cell population (e.g., hair follicle or epidermal stem cells), wherein a method for treating hair loss (e.g., preventing hair loss and/or promoting hair growth; e.g., in aging subjects) is afforded.

Further aspects provide methods for treating a condition or disease of the skin or at least one symptom thereof, comprising administering to a subject in need thereof an amount of a CBP/catenin (e.g., CBP/β-catenin) antagonist sufficient for treating a condition or disease of the skin or at least one symptom thereof.

Exemplary Preferred Aspects:

Particular aspects provide a method for treating aging or an age-related condition, symptom or disease, comprising: identifying a mammalian subject having somatic stem cells for least one tissue compartment or type having an age-related condition, symptom or disease; and administering to the subject a CBP/Catenin (e.g., CBP/β-catenin) antagonist in a manner and amount sufficient to provide for increasing the number of asymmetric renewing divisions relative to, or at the expense of symmetric divisions of the somatic stem cells for the at least one tissue compartment or type, wherein the age related condition, symptom or disease of the tissue compartment or type is decreased or ameliorated, wherein a method for treating aging or an age-related condition, symptom or disease is afforded. In certain aspects, the somatic stem cells for the at least one tissue compartment or type comprise quiescent somatic stem cells, and wherein administering the CBP/β-catenin antagonist comprises CBP/β-catenin antagonist-mediated activation of the quiescent somatic stem cells to enhance or accelerate asymmetric renewing divisions relative to, or at the expense of symmetric divisions among the somatic stem cells of the at least one tissue compartment or type.

In particular aspects, the somatic stem cells comprise at least one selected from the stem cell group consisting of skin including keratinocyte stem cells, epidermal, follicular, hematopoietic, mammary, intestinal epithelium including crypt cells, mesenchymal including muscle satellite cells, melanocyte stem cells, osteoblasts and chondrocyte progenitors, endothelial, neural, including either the ependymal or the subventricular zone cells, neural crest, olfactory, testicular, uterine.

In particular hair growth aspects, the somatic stem cells for the at least one tissue compartment or type, comprise hair follicle stem cells of a skin tissue compartment, and wherein increased hair growth or hair pigmentation is provided at the skin tissue compartment or type, preferably at the scalp tissue compartment or type. In certain embodiments, the CBP/β-catenin antagonist is present in an amount sufficient to modulate or increase the expression of an adenosine receptor in dermal cells, preferably dermal papilla cells. In certain embodiments, the adenosine receptor is at least one selected from A1, A2A, and A2B. In certain hair growth aspects, the CBP/Catenin (e.g., CBP/β-catenin) antagonist is present in an amount sufficient to modulate or increase the expression of sulfonylurea receptor 2B in dermal cells, preferably dermal papilla cells.

Certain hair growth aspects comprise co-administration of or adjunct treatment with at least one other hair growth stimulating agent, or hair loss preventing agent (e.g., at least one selected from the group consisting of minoxidil, finasteride, dutasteride, bimatoprost and antiandrogen receptor blockers including fluridil).

In particular skin repair homeostatic maintenance aspects of the disclosed methods, the somatic stem cells for the at least one tissue compartment or type, comprise skin stem cells of a skin tissue compartment or type, and wherein enhanced skin repair and/or homeostatic maintenance is provided at the skin tissue compartment or type. In particular aspects, enhanced skin repair and/or homeostatic maintenance relates to at least one age-related condition, symptom or disease selected from the group consisting of skin conditions including wrinkles, hyperpigmentation, redness, rosacea, dryness, cracking, loss of firmness, loss of elasticity, thinning, loss of vibrance, wounds, scars, acne, sun damage, susceptibility to viral infection (e.g., to HSV, HPV), ulcers including diabetic ulcers, burns, atopic dermatitis, psoriasis, and hair loss or loss of hair coloration. Certain skin repair homeostatic maintenance aspects comprise treating with a CBP/Catenin (e.g., CBP/β-catenin) antagonist to decrease scarring in the wound to the surface tissue, wherein scarring is reduced. In certain embodiments, treating comprises accelerating epidermal or dermal layering and/or increasing cellular migration of at least one type of cell to the wound (e.g., wherein the type of cellular migration or proliferation comprises at least one cell selected from the group consisting of: keratinocytes, fibroblasts, epidermal cells, dermal cells, epithelial cells, mast cells, neutrophils, lymphocytes, and macrophages). In particular aspects, treating accelerates neoangiogenesis of blood vessels or lymphatic vessels, and/or increases collagen deposition at the wound. Certain aspects comprise treating a wound to a surface tissue or a symptom thereof of at least one wound type selected from the group consisting of lacerations, abrasions, rupture, puncture wounds, chemical, thermal, or radiation-induced burns, cuts, scrapes, incisions, blisters, diabetic ulcers, bedsores or pressure ulcers, skin grafts, and surgical wounds.

In particular aspects, the age-related condition, symptom or disease, comprises at least one condition, symptom or disease selected from the group consisting of skin conditions including wrinkles, hyperpigmentation, redness, rosacea, dryness, cracking, loss of firmness, loss of elasticity, thinning, loss of vibrance, wounds, scars, acne, sun damage, latent viral infection (e.g., to HSV, HPV), ulcers including diabetic ulcers, burns, atopic dermatitis, psoriasis, and hair loss or loss of hair coloration.

In particular embodiments, the CBP/Catenin (e.g., CBP/β-catenin) antagonist is at least one selected from the group of compounds and salts thereof of Table 1, or another compound disclosed herein. In certain aspects, the CBP/Catenin (e.g., CBP/β-catenin) antagonist comprises an alkyl and/or fatty acid ester derivative thereof as disclosed herein. In particular aspects, the CBP/β-catenin antagonist comprises ICG-001 or an active alkyl and/or fatty acid ester derivative thereof as disclosed herein.

In certain aspects, administration of the CBP/Catenin (e.g., CBP/β-catenin) antagonist comprises at least of one topical, gingival, buccal, sub cutaneous, and oral administration.

Certain aspects comprise co-administration of or adjunct treatment with at least one other therapeutic agent (e.g., with an anti-inflammatory agent; e.g., a steroid or glucocorticoid steroid). In certain aspects, said anti-inflammatory agent comprises at least one anti-inflammatory agent is selected from the group consisting of: short-acting β$_2$-agonists, long-acting β$_2$-agonists, anticholinergics, corticosteroids, systemic corticosteroids, mast cell stabilizers, leukotriene modifiers, methylxanthines, β$_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methylprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, glucocorticoid steroids, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof.

In certain aspects, the one additional therapeutic agent is selected from the group consisting of anti-microbial agents, antifungal agents, and antibiotic agents (e.g., ciclosporin, hyaluronic acid, carmellose, macrogol(s), dextran and hyprolose, sodium and calcium, sodium and povidone, hypromellose, carbomer, amikacin, gentamicin, kanamycin, neomycin, netilmicin, streptomycin, tobramycin, paromomycin, geldanamycin, herimycin, loracarbef, ertapenem, imipenem/cilastatin, meropenem, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, peperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, tinidazole, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, teronazole, terbinafine, amorolfine, naftifine, butenafine, anidulafungin, caspofungin, micafungin, ciclopirox, flucytosine, griseofulvin, Gentian violet, haloprogin, tolnaftate, undecylenic acid, and combinations thereof), and antiviral (e.g., acyclovir, docosanol).

Additional aspects provide methods for stimulating hair growth, regrowth or pigmentation, comprising administering to a subject in need thereof an amount of a CBP/Catenin (e.g., CBP/β-catenin) antagonist sufficient for stimulating at least one of hair growth, regrowth, and pigmentation. Certain aspects comprise administering the CBP/Catenin (e.g., CBP/β-catenin) antagonist in a manner and amount sufficient to provide for increasing the number of asymmetric renewing divisions relative to, or at the expense of symmetric divisions of somatic follicular stem cells, wherein at least one of hair growth, regrowth, and pigmentation is afforded. In particular embodiments, the CBP/β-catenin antagonist is present in an amount sufficient to modulate or increase the expression of an adenosine receptor (e.g., at least one selected from A1, A2A, and A2B) in dermal cells (e.g., dermal papilla cells). In certain aspects, the CBP/Catenin (e.g., CBP/β-catenin) antagonist is present in an amount sufficient to modulate or increase the expression of sulfonylurea receptor 2B in dermal papilla cells.

In particular embodiments for stimulating hair growth, the CBP/Catenin (e.g., CBP/β-catenin) antagonist is at least one selected from the group of compounds and salts thereof of Table 1, or another compound disclosed herein. In certain aspects, the CBP/Catenin (e.g., CBP/β-catenin) antagonist comprises an alkyl and/or fatty acid ester derivative thereof as disclosed herein. In particular aspects, the CBP/Catenin (e.g., CBP/β-catenin) antagonist comprises ICG-001 or an active alkyl and/or fatty acid ester derivative thereof as disclosed herein.

In certain aspects, administration of the CBP/Catenin (e.g., CBP/β-catenin) antagonist comprises at least of one topical, gingival, buccal, sub cutaneous, and oral administration.

Certain embodiments for stimulating hair growth comprise co-administration of or adjunct treatment with at least one other hair growth stimulating agent, or hair loss preventing agent (e.g., at least one selected from the group consisting of minoxidil, finasteride, dutasteride, bimatoprost and antiandrogen receptor blockers including fluridil). Certain aspects comprise co-administration of or adjunct treatment with at least one anti-inflammatory agent (e.g., at least one anti-inflammatory agent is selected from the group consisting of: short-acting $\beta_2$-agonists, long-acting $\beta_2$-agonists, anticholinergics, corticosteroids, systemic corticosteroids, mast cell stabilizers, leukotriene modifiers, methylxanthines, $\beta_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, glucocorticoid steroids, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof).

Further aspects of the invention provide methods for increasing the expression of an adenosine receptor in dermal cells, comprising administering to a subject in need thereof an amount of a CBP/Catenin (e.g., CBP/β-catenin) antagonist sufficient for increase the expression of an adenosine receptor (e.g., is at least one selected from A1, A2A, and A2B) in dermal cells, preferably dermal papilla cells. In certain aspects of the methods, the CBP/Catenin (e.g., CBP/β-catenin) antagonist is present in an amount sufficient to modulate or increase the expression of sulfonylurea receptor 2B in dermal papilla cells.

In particular embodiments for increasing the expression of an adenosine receptor in dermal cells, the CBP/Catenin (e.g., CBP/β-catenin) antagonist is at least one selected from the group of compounds and salts thereof of Table 1, or another compound disclosed herein. In certain aspects, the CBP/Catenin (e.g., CBP/β-catenin) antagonist comprises an alkyl and/or fatty acid ester derivative thereof as disclosed herein. In particular aspects, the CBP/Catenin (e.g., CBP/β-catenin) antagonist comprises ICG-001 or an active alkyl and/or fatty acid ester derivative thereof as disclosed herein.

In certain aspects, administration of the CBP/Catenin (e.g., CBP/β-catenin) antagonist comprises at least of one topical, gingival, buccal, sub cutaneous, and oral administration.

Yet further aspects provide methods for treating a condition or disease of the skin or at least one symptom thereof, comprising administering to a subject in need thereof an amount of a CBP/Catenin (e.g., CBP/β-catenin) antagonist sufficient for treating a condition or disease of the skin or at least one symptom thereof. Certain aspects of the methods comprise administering the CBP/Catenin (e.g., CBP/β-catenin) antagonist in a manner and amount sufficient to provide for increasing the number of asymmetric renewing divisions relative to, or at the expense of symmetric divisions of somatic skin stem cells, wherein treating a condition or disease of the skin or at least one symptom thereof is afforded. In particular embodiments, the condition or disease of the skin, comprises at least one condition or disease selected from the group consisting of wounds, scars, acne, sun damage, latent viral infection (e.g., to HSV, HPV), ulcers including diabetic ulcers, burns (including sunburn, UVB damage), atopic dermatitis, psoriasis, and effects of aging including wrinkles, hyperpigmentation, redness, rosacea, dryness, cracking, loss of firmness, loss of elasticity, thinning, and loss of vibrance.

In particular embodiments for treating a condition or disease of the skin or at least one symptom thereof, the CBP/Catenin (e.g., CBP/β-catenin) antagonist is at least one selected from the group of compounds and salts thereof of Table 1, or another compound disclosed herein. In certain aspects, the CBP/Catenin (e.g., CBP/β-catenin) antagonist comprises an alkyl and/or fatty acid ester derivative thereof as disclosed herein. In particular aspects, the CBP/Catenin (e.g., CBP/β-catenin) antagonist comprises ICG-001 or an active alkyl and/or fatty acid ester derivative thereof as disclosed herein.

In certain aspects, administration of the CBP/Catenin (e.g., CBP/β-catenin) antagonist comprises at least of one topical, gingival, buccal, sub cutaneous, and oral administration.

Certain aspects for treating a condition or disease of the skin or at least one symptom thereof comprise co-administration of or adjunct treatment with at least one other therapeutic agent (e.g., with an anti-inflammatory agent; e.g., steroid or glucocorticoid steroid, etc.). In particular embodiments, the at least one anti-inflammatory agent is selected from the group consisting of: short-acting $β_2$-agonists, long-acting $β_2$-agonists, anticholinergics, corticosteroids, systemic corticosteroids, mast cell stabilizers, leukotriene modifiers, methylxanthines, $β_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, glucocorticoid steroids, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof.

In additional aspects of methods for treating a condition or disease of the skin or at least one symptom thereof, the one additional therapeutic agent is selected from the group consisting of anti-microbial agents, antifungal agents, and antibiotic agents (e.g., ciclosporin, hyaluronic acid, carmellose, macrogol(s), dextran and hyprolose, sodium and calcium, sodium and povidone, hypromellose, carbomer, amikacin, gentamicin, kanamycin, neomycin, netilmicin, streptomycin, tobramycin, paromomycin, geldanamycin, herimycin, loracarbef, ertapenem, imipenem/cilastatin, meropenem, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, peperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, tinidazole, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, teronazole, terbinafine, amorolfine, naftifine, butenafine, anidulafungin, caspofungin, micafungin, ciclopirox, flucytosine, griseofulvin, Gentian violet, haloprogin, tolnaftate, undecylenic acid, and combinations thereof).

Particular aspects of methods for treating a condition or disease of the skin or at least one symptom thereof comprise treating a wound to decrease scarring in the wound to the surface tissue, wherein scarring is reduced, and/or accelerating epidermal or dermal layering. In certain embodiments, the treating comprises increasing cellular migration of at least one type of cell to the wound (e.g., wherein the type of cellular migration or proliferation comprises at least one cell selected from the group consisting of: keratinocytes, fibroblasts, epidermal cells, dermal cells, epithelial cells, mast cells, neutrophils, lymphocytes, and macrophages). In particular embodiments the treating accelerates neoangiogenesis of blood vessels or lymphatic vessels and/or increases collagen deposition at the wound. Certain aspect comprise treating a wound to a surface tissue or a symptom thereof of at least one wound type selected from the group consisting of lacerations, abrasions, rupture, puncture wounds, chemical, thermal, or radiation-induced burns, cuts, scrapes, incisions, blisters, diabetic ulcers, bedsores or pressure ulcers, skin grafts, and surgical wounds.

Yet additional aspects comprise methods for cosmetically treating a condition of the skin or at least one symptom thereof, comprising administering to a subject in need thereof an amount of a CBP/Catenin (e.g., CBP/β-catenin) antagonist sufficient for cosmetically treating a condition of the skin or at least one symptom thereof. Certain embodiments of the methods comprise administering the CBP/Catenin (e.g., CBP/β-catenin) antagonist in a manner and amount sufficient to provide for increasing the number of asymmetric renewing divisions relative to, or at the expense of symmetric divisions of somatic skin stem cells, cosmetically treating a condition of the skin or at least one symptom thereof is afforded. Certain aspects comprise treating at least one condition or disease selected from the group consisting of wrinkles, scarring, hyperpigmentation, redness, rosacea, dryness, cracking, loss of firmness, loss of elasticity, thinning, and loss of vibrance.

In particular embodiments for methods for cosmetically treating a condition of the skin or at least one symptom thereof, the CBP/Catenin (e.g., CBP/β-catenin) antagonist is at least one selected from the group of compounds and salts thereof of Table 1, or another compound disclosed herein. In certain aspects, the CBP/Catenin (e.g., CBP/β-catenin) antagonist comprises an alkyl and/or fatty acid ester derivative thereof as disclosed herein. In particular aspects, the CBP/Catenin (e.g., CBP/β-catenin) antagonist comprises ICG-001 or an active alkyl and/or fatty acid ester derivative thereof as disclosed herein. In certain aspects, administration of the CBP/Catenin (e.g., CBP/β-catenin) antagonist comprises at least of one topical, gingival, buccal, sub cutaneous, and oral administration.

DETAILED DESCRIPTION

Figure 1:
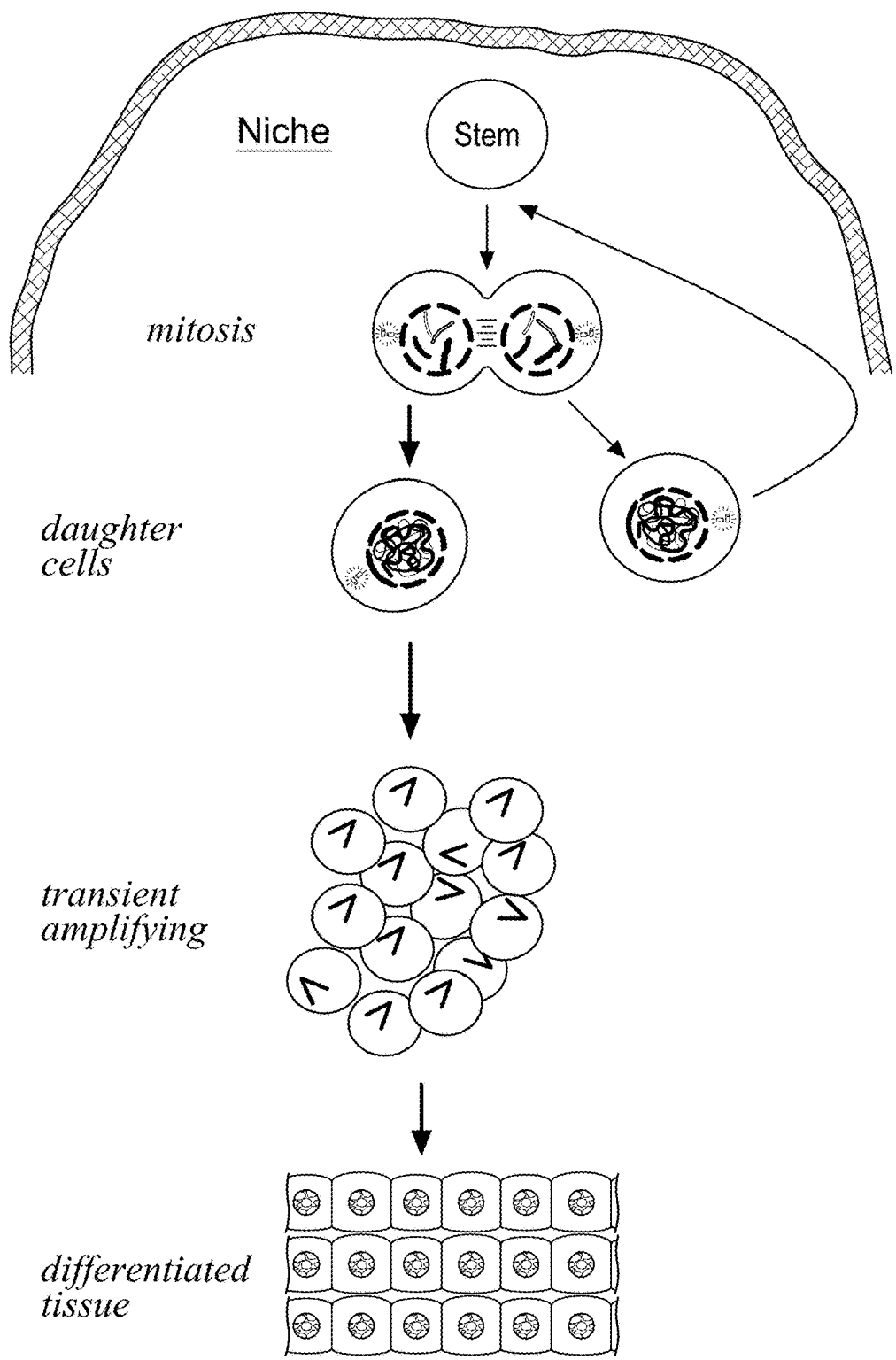
FIG. 1 shows a schematic of Balanced Asymmetric Division of Stem Cells. Ideally, upon entry into mitosis, one of the 2 daughter cells will remain in its niche as a stem cell, while the other goes on to initially transiently amplify and subsequently to differentiate to maintain tissue homeostasis.

Definitions. The term "CBP protein" refers to the protein that is also known as CREB-binding protein, where CREB is an abbreviation for "cAMP-response element binding". This protein is well known in the art, see, e.g., Takemaru et al., J. Cell Biol. 149:249-54 (2000) and U.S. Pat. No. 6,063,583. CBP 1-111 refers to the first 111 amino acids of the protein CBP, as identified from the N-terminus of CBP.

The term "p300 protein" refers to a protein that is well known in the art. See, e.g., Gusterson, R. J. et al., J. Biol. Chem. 2003 Feb. 28; 278(9):6838-47; An and Roeder, J. Biol. Chem. 2003 Jan. 17; 278(3):1504-10; Rebel, V. I. et al., Proc Natl Acad Sci USA. 2002 Nov. 12; 99(23):14789-94; and U.S. Pat. No. 5,658,784, as well as references cited therein. p300 1-111 refers to the first 111 amino acids of the protein p300, as identified from the N-terminus of p300.

The phrase "Wnt pathway" refers to a signaling cascade that may be initiated by the binding of Wnt proteins (secreted glycoproteins) to frizzled seven-transmembrane-span receptors. This pathway is known and characterized in the art and is the subject of numerous articles and reviews (see, e.g., Huelsken and Behrens, J. Cell Sci. 115: 3977-8, 2002;

Wodarz et al., *Annu. Rev. Cell Dev. Biol.* 14:59-88 (1998); Morin, P. J., *Bioessays* 21:1021-30 (1999); Moon et al., *Science* 296:1644-46 (2002); Oving et al., *Eur. J. Clin. Invest* 32:448-57 (2002); Sakanaka et al., *Recent Prog. Horm. Res.* 55: 225-36, 2000).

The phrase "the activity of the Wnt pathway" refers to the activity of at least one component of the pathway. For example, the activity of the Wnt pathway, in certain embodiments, may refer to the activity of β-catenin in inducing expression of targeted genes. Many components of the Wnt pathway are known in the art, and include but are not limited to Cerberus (Cer), FrzB, Dickkopf (DKK), LRP, heterotrimeric G protein, Dsh, casein kineaase 1a (CK1a), GSK3β, βTrCP, ACP, Axin, CBP, p300, β-catenin, TCF, Froucho, etc.

A compound that "activates the Wnt pathway" refers to a compound that leads to β-catenin induced expression of target genes when present in a system having the Wnt pathway. Many target genes whose expression is induced by β-catenin are known in the art, and include but are not limited to Conductin, Myc, Twin, Cyclin D1, Nkd, Ubx, En-2, PPARd, Xbra, ID2, Siamois, Xnr3, MMP7, TCF-1, survivin, etc. Such genes may also be referred to as "genes targeted by the Wnt/β-catenin pathway."

The phrase "selectively inhibiting expression of genes targeted by the Wnt/β-catenin pathway" refers to inhibiting the expression of a subset of genes targeted by the Wnt/β-catenin pathway, but not inhibiting the expression of the other genes targeted by the Wnt/β-catenin pathway. Although not wished to be bound to any particular mechanism, the inventors of the present invention speculate that the selective inhibition of gene expression may be accomplished by interrupting the interaction between β-catenin and some, but not all, of its potential binding partners.

I. Aging and Age-related Conditions

Particular aspects of the present invention provide compositions comprising CBP/catenin (e.g., CBP/β-catenin) antagonists for use in increasing the number of asymmetric renewing divisions at the expense of symmetric divisions in a stem cell population to provide for treating aging or a condition or disease of aging, or at least one symptom thereof.

According to particular aspects, the decision for a stem cell to undergo a symmetric versus an asymmetric differentiation is a critical cellular decision process in adults, underlies a variety of conditions and diseases associated with a decrease in tissue maintenance/homeostasis and/or ability to repair properly (as in wound healing, hematopoiesis, fibrosis and osteoporosis), and is a key underlying problem associated in general with aging. Interestingly and importantly, the decision to divide asymmetrically or symmetrically is likely a major fundamental intrinsic difference between normal somatic stem and cancer stem cells. Based upon work done primarily in applicants' laboratory over the past 10 years (both published and unpublished data), the following disclosure supports the critical importance of symmetric versus asymmetric divisions and the role of differential coactivator usage (e.g., CBP vs. p300) in the Wnt/catenin signaling cascade in stem cells and how they can be pharmacologically manipulated.

Symmetry versus asymmetry in somatic stem cells. A stem cell, for present purposes, is a cell located in a specific microenvironment or niche that has the ability to either remain quiescent (i.e., essentially do nothing) or to enter the cell cycle and undergo mitosis (i.e., cell division) giving rise to two daughter cells. Ideally, an asymmetric balance is maintained, whereby one of the daughter cells remains in the niche as a stem cell, while the other daughter proceeds forward in the differentiation process to provide a "transient amplifying population" to maintain tissue homeostasis (FIG. 1).

According to particular aspects, this asymmetric balance of fates between the two daughter cells is not always maintained and in some instances, the two daughter cells end up either both as stem cells, or both going on to differentiate, thereby losing their "stemness". This type of symmetric division is, according to particular aspects, deleterious to the normal stem cell population.

Although symmetry versus asymmetry is in essence an extremely simple binary decision process (a 0/1 decision as in computer logic), the stem cell in the niche undergoing mitosis must read an enormously complex array of information from its environment (e.g., oxygen levels, nutrient levels, light/dark i.e. circadian cycles, growth factors, adhesion molecules, cell/cell contacts, etc.) to arrive at this eventual binary decision. The question then is; how does a stem cell in the niche read this plethora of information and distill it down into a simple molecular 0/1 decision point? Applicant's lab has made significant progress in understanding various players and circuitry involved in this binary decision of symmetry versus asymmetry. Utilizing a set of unique pharmacologic tools that were developed through a forward chemical genomic approach, applicant can now can manipulate and modulate this binary decision in both normal stem/progenitor populations as well as cancer stem/progenitor populations.

The findings herein indicate that the decision to divide asymmetrically or symmetrically is a fundamental intrinsic difference between normal stem and cancer stem cells, and further that modulation of the balance between symmetric and asymmetric division provides a way to treat aging.

Pharmacologic Tools

Wnt Signaling. Applicant's initial goal was not to develop pharmacologic tools for studying symmetry versus asymmetry but rather to find a way to inhibit aberrant Wnt pathway activation. Due to mutations in the genes Adenomatous Polyposis Coli (APC) or beta-catenin, approximately 90% of colon cancers have constitutive activation of the Wnt signaling cascade. Therefore, the original notion was that if this aberrant Wnt signal could be antagonized, it may provide a new therapeutic strategy for colorectal cancer.

The Wnt signaling cascade is enormously complex. Wnt signaling plays important roles throughout development and also in day-to-day processes, for example, maintenance of the skin and hair, maintenance of intestinal homeostasis, regulation of hematopoietic stem/progenitors as well as lineage commitment of progenitors during hematopoiesis (i.e., in general blood homeostasis) etc. (1, 2). Other cell replacement activities that occur in the human body, e.g., liver turnover, neurogenesis, etc., also involve Wnt signal transduction (3-5). Although, there is general agreement that Wnt signaling is important in stem cell biology, there is no consensus and a great deal of controversy, as to whether Wnt signaling is important for proliferation and maintenance of pluripotency or multipotency, or on the other hand differentiation of the same stem/progenitor cells. Classical Wnt/signaling (termed canonical Wnt signaling or Wnt/beta-catenin signaling) has as its hallmark a soluble pool of cytoplasmic beta-catenin, associated with the degradation complex that consists of the core proteins Axin, APC, GSK3 (glycogen synthase kinase 3), and CK1-alpha (casein kinase 1-alpha). In the absence of Wnt ligand, beta-catenin is phosphorylated within this complex thereby targeting it for ubiquitination and subsequent destruction by the proteasomal machinery (6). Activation of the Wnt pathway triggers a series of events that disrupts the APC/Axin/GSK3 complex that is required for the targeted destruction of beta-catenin, and thereby promotes the stabilization and accumulation of beta-catenin in the cytoplasm. This build-up in the cytoplasm coincides with the translocation of beta-catenin into the nucleus through a mechanism that is still not entirely defined. In the nucleus, beta-catenin, in the classical definition of the Wnt signaling cascade, forms a complex with members of the TCF/LEF family of transcription factors. To generate a transcriptionally active complex, beta-catenin recruits the transcriptional coactivators, cAMP response element-binding protein (CREB)-Binding Protein (CBP) or its closely related homolog, p300 (E1A-Binding Protein, 300-KD) as well as other components of the basal transcription machinery, leading to the expression of a host of downstream target genes (7, 8). Applicants' research has also demonstrated that CBP's partnership with members of the catenin family is not restricted to beta-catenin. In the absence of beta-catenin, CBP can also partner with other catenin-like molecules (e.g., gamma-catenin) (9).

CBP and p300. CBP and p300 are large proteins of about 300 kd. They have long been considered as having redundant roles, and treated in the literature as one and the same protein. Recent work has documented that CBP and p300 interact with hundreds of proteins in their roles as master orchestrators of transcription. Despite their high degree of homology, accumulating evidence indicates that CBP and p300 are not redundant but have definitive and unique roles both in vitro and in vivo (10-12). Targeted mutagenesis studies in mice have demonstrated that mammalian development is extremely sensitive to CBP and p300 gene dosage. Mice heterozygous for a targeted mutation of CBP (CBP+/−) have been shown to exhibit skeletal abnormalities, some of which resemble a relatively rare genetic disorder Rubinstein-Taybi Syndrome (RTS) (13). Analysis of p300 mutant mice indicated that the gene dosage of p300 is also important for development (14). Strikingly, both CBP heterozygous (CBP+/−) and p300 heterozygous (p300+/−) mouse embryos display an exencephalic phenotype similar to the knockout (p300−/− and CBP−/−) mouse embryos (15). Despite their high degree of homology and similar patterns of expression, it is becoming very evident that CBP and p300 play unique and distinct roles in gene regulation. Applicant recently demonstrated that CBP and p300 have distinct functions in the regulation of TCF/β-catenin mediated survivin transcription (16, 17). These results are consistent with other publications demonstrating the non-redundant roles for CBP and p300 in cell growth, differentiation and development (10, 14, 18, 19). Rebel et al. (20), using a hematopoietic stem cell (HSC) model, concluded that CBP and not p300, is essential for HSC self-renewal, whereas p300 is critical for proper hematopoietic differentiation. Ugai et al. (21) found that p300, but not CBP, is absolutely required for RA-induced F9 differentiation.

Figure 2A:
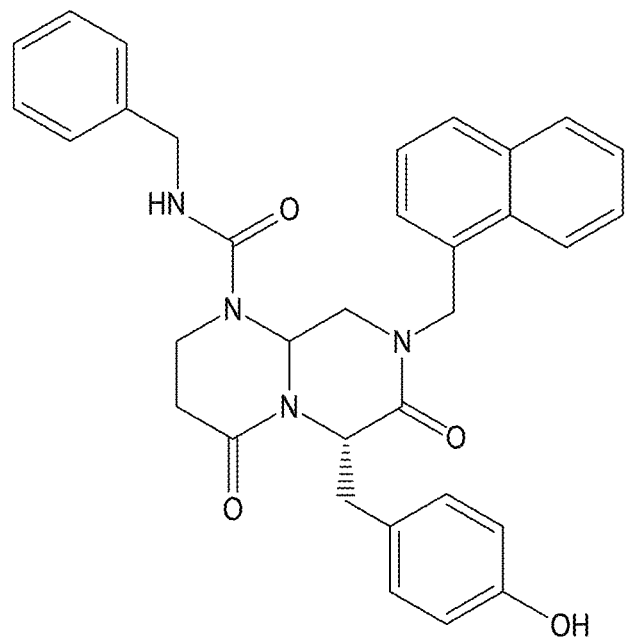
FIG. 2 shows the structures of the Catenin Coactivator Modulators (a) ICG-001 and (b) IQ-1.

ICG-001. Applicant's pharmacologic tools were identified using cell-based forward chemical genomic screens of small molecule secondary structure template chemical libraries (22). Due to mutations in the gene APC, SW480 colon carcinoma cells exhibit constitutive translocation of beta-catenin to the nucleus, and thus high basal Wnt/catenin transcription as assessed by the consensus TCF/catenin luciferase reporter construct TOPFLASH. Using this reporter system, Applicant previously identified the compound ICG-001, which had an $IC_{50}$ of 30 µM (FIG. 2a). Utilizing an affinity chromatography approach, it was determined and subsequently validated, using a gain-of function/loss-of-function strategy, that ICG-001 binds specifically and with high affinity (~1 nM) to the coactivator CBP, but importantly, not to its closely related homolog p300, despite the fact that these two coactivators are up to 93% identical, with even higher homology, at the amino acid level (22, 23).

Applicant next mapped the binding domains between CBP and beta-catenin, as well as between p300 and beta-catenin. The C-terminal trans-activating region of beta-catenin (647-781) interacted with the same 1-111 amino acids of both CBP and p300 (23). However, only the interaction between CBP and beta-catenin was disrupted by ICG-001, and not the p300/beta-catenin interaction. Subsequent binding and isothermal calorimetry studies demonstrated that ICG-001 bound selectively and directly with high affinity (~1 nM) to the N-terminus of CBP. In summary, Applicant's data confirmed a direct association between CBP and ICG-001, and the ability of ICG-001 to selectively disrupt the CBP/beta-catenin interaction, without affecting the p300/beta-catenin interaction despite the extremely high degree of homology between the two coactivators.

ICG-001 provides a unique tool that enables one to specifically and selectively block only the very amino terminus of CBP, which is responsible for the interaction between CBP and catenin. As the region that ICG-001 binds to on CBP is limited to the very amino terminus, it follows that the downstream changes that this compound effects are not global, but limited only to functions that this region of CBP controls. An analogy can be drawn between a basketball and a golf ball—when a golf ball is placed up against the basketball, the surface area that the golf ball covers on the basketball is not very large, thus leaving the rest of the basketball unaffected. In the same way, ICG-001 blocks a very small region of CBP, leaving the other regions on the coactivator unaffected and open to interactions with its other cognate binding partners.

Figure 2B:
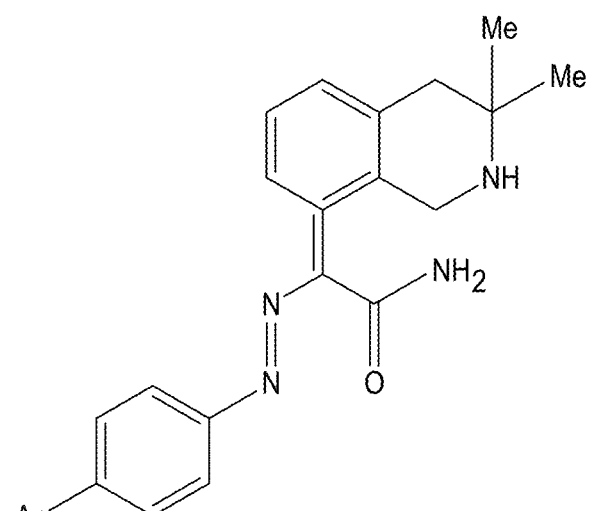

IQ-1. In addition to ICG-001, a screen of a large chemical library for maintenance of pluripotency in mES cells led to the identification of another compound, termed IQ-1 (FIG. 2b). IQ-1 maintains the pluripotency of murine embryonic stem cells (mESCs) in long-term culture in a Wnt-dependent manner. Subsequently, Applicant determined that IQ-1 binds to the PR72/130 subunit of the serine/threonine phosphatase PP2A. The binding of IQ-1 to PR72/130 leads to decreased phosphorylation of the coactivator protein p300 at Ser-89, through an as yet undetermined mechanism. Applicant also demonstrated that the phosphorylation of p300 at Ser-89 enhances the binding affinity of beta-catenin to p300. I-Q-1 diminishes the interaction between p300 and beta-catenin thereby increasing the CBP/beta-catenin interaction (24).

Figure 3A:
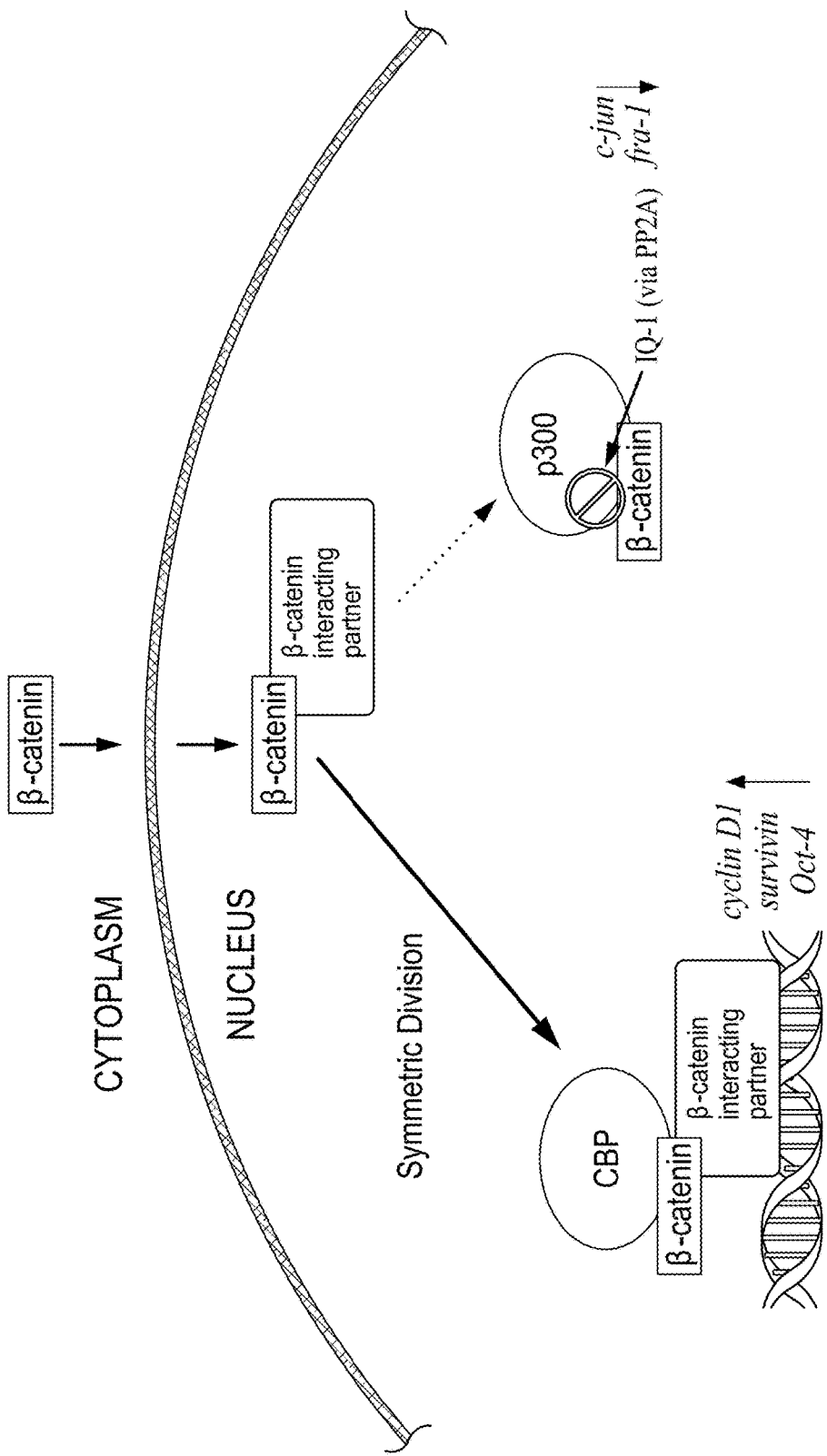
FIG. 3 shows a model of Differential Coactivator Usage. (A) IQ-1 antagonizes the interaction between p300 and catenin thus forcing the stem/progenitor cell to utilize CBP/catenin-driven transcription. This results in increased symmetric divisions. (B) ICG-001 blocks the interaction between CBP and catenin, thus forcing the cell to utilize p300/catenin-driven transcription. This initiates the transcription of genes involved in initiating the differentiation process.

FIG. 3A & B show a pictorial representation of the molecular targets of ICG-001 and IQ-1 and their points of interaction within the context of Wnt/catenin signaling. With these tools in hand, applicant explored the effects of CBP or p300 differential coactivator usage on catenin mediated transcription. This would have been difficult, if not impossible to do using classical "knockout" or "knockdown" techniques as CBP and p300 interact with a very large number (at least 400) of partners other than beta-catenin (25). Genetic deletion of CBP or p300 has complex consequences affecting a multitude of different transcription factors. This highlights the importance of the forward chemical genetic approach if appropriately utilized (22).

Wnt Signaling in Proliferation and Differentiation

Wnt signaling plays important roles throughout development. Although almost all would agree that Wnt/catenin signaling is important in stem cell biology, there is no consensus as to whether Wnt signaling is important for proliferation and maintenance of potency (pluri- or multipotency) or differentiation of stem/progenitor cells. Wnt/catenin signaling has been demonstrated to maintain pluripotency in ES cells (24, 26) and recently, a critical role for beta-catenin for the maintenance of expression of the key pluripotency transcription factor Oct4, in a TCF-independent fashion, has been demonstrated (27). Wnt/catenin signaling has been shown to enhance neuronal stem/progenitor cell proliferation.

However, Wnt/catenin signaling is also required for neural differentiation of ES cells, fate decision in neural crest stem cells and Wnt3a has been reported to promote differentiation into the neural and astrocytic lineages by inhibiting neural stem cell maintenance (28-30). These dramatically diverse and divergent responses that result from the activation of the Wnt signaling pathway, by essentially the same Wnts in the same cell types, has fueled enormous controversy concerning the role of Wnt signaling in the maintenance of potency versus the induction of differentiation. It also begs the question of how the Wnt signaling network integrates the various inputs that a cell receives to elicit the correct and coordinated responses. Until now, a rationale for the dichotomous behavior of Wnt/catenin signaling in controlling both proliferation and differentiation has been unclear.

Non-redundant Roles of CBP and p300 in Wnt/Catenin Signaling

Figure 3B:
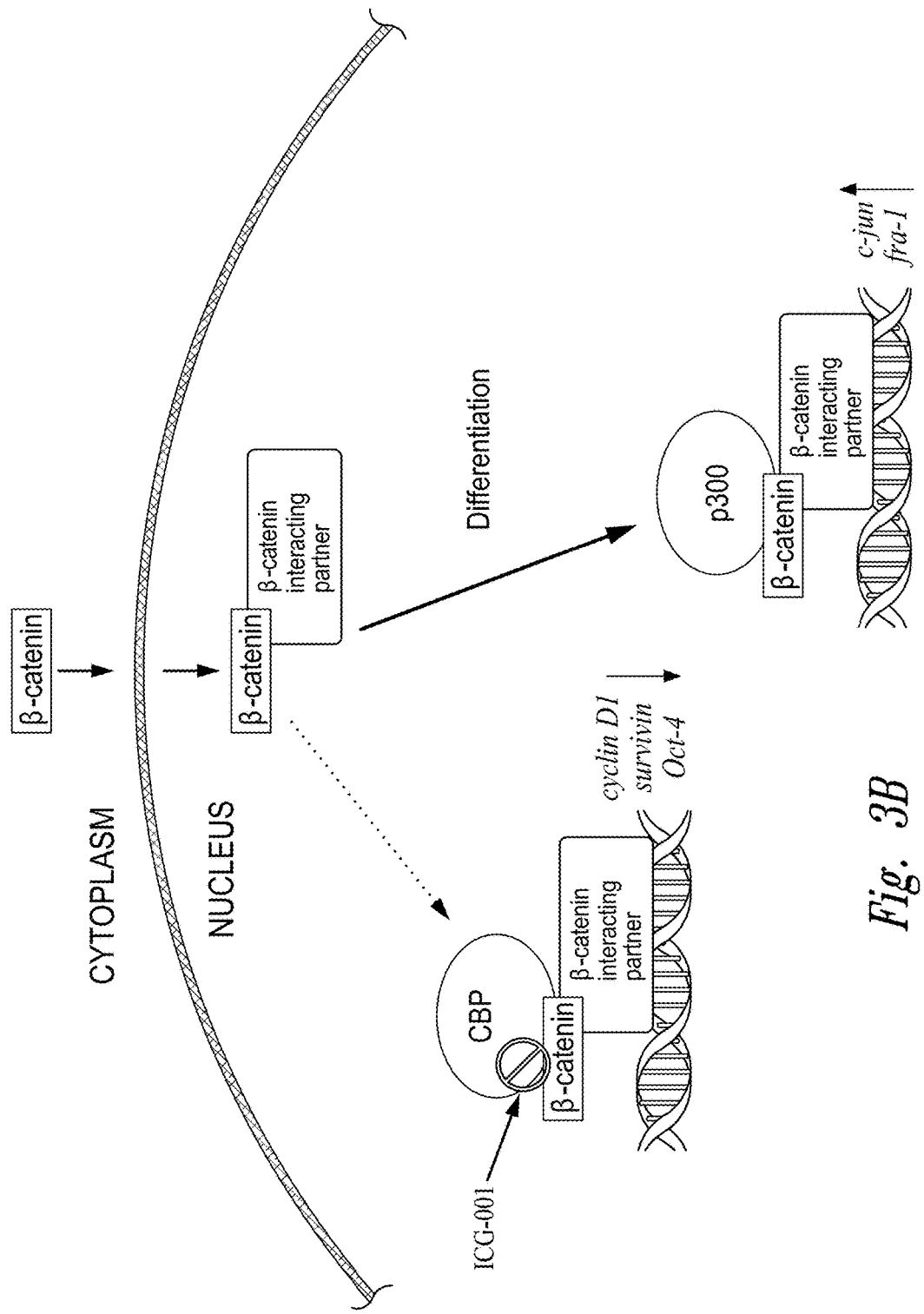

One of applicant's earlier studies demonstrated that selectively blocking the interaction between the two proteins CBP and beta-catenin with ICG-001 led to the initiation of a differentiative program. This led to the development of applicant's model of differential coactivator usage (16, 24). The model highlights the distinct roles of the coactivators CBP and p300 in the Wnt/catenin signaling cascade (FIGS. 3A and 3B). The critical feature of the model is that the decision to utilize either CBP or p300 is the first decision that guides the cell to initiate either a proliferative/maintenance of potency or differentiative transcriptional program, respectively. Note that this first step is followed by other epigenetic modifications (e.g., histone methylation/demethylation and histone acetylation/deacetylation, etc.) as well as the recruitment of additional transcription factors for both the subsequent expansion of transient amplifying populations and/or lineage commitment (Wend et al. manuscript under revision Cancer Cell, Ma et al Oncogene 2005). In other words, the first step of catenin partnering with either p300 or CBP is not the be all and end all, but rather the initiating process, which is followed by the involvement of other endogenous proteins, coactivators, enzymes (e.g., histone deacetylaces, DNA methyl transferases etc.) and transcription factors, depending on the level of cellular potency, lineage and context. This model posits that a CBP/catenin-mediated transcription is critical for stem cell/progenitor cell maintenance and proliferation, whereas the usage of p300/catenin mediates a transcriptional program that initiates differentiation, and a decrease in cellular potency.

The decision to utilize either CBP/catenin or p300/catenin driven transcription appears to be an extremely fundamental event as it is already critical even at the first cellular potency decision point. The earliest differentiation event, hence the first asymmetric division in mammals, occurs in the preimplantation embryo at the 8-cell stage resulting in the formation of two distinct cell populations; the outer trophectoderm (TE) and the inner cell mass (ICM). Prior to this point, all cellular divisions appear to be symmetric and all cells remain essentially equivalent and pluripotent. Cells within the ICM are considered pluripotent as they will give rise to the components of all three germ layers, as well as, cells contributing to extraembryonic endoderm and mesoderm. The outer layer of TE, on the other hand, does not contribute to any embryonic tissue but gives rise to extraembryonic ectoderm and can differentiate into multiple trophoblast cell types. Applicant has demonstrated that even at this earliest and arguably the most important cellular decision point, the choice between ICM and TE is governed by differential coactivator usage by catenin: i.e., CBP/catenin is required for maintenance of the ICM and expression of Oct4, whereas the usage of p300/catenin initiates the formation of Cdx2 positive trophectoderm (31). According to particular aspects of the present invention, this fundamental decision process that occurs at the first symmetric versus asymmetric differentiation is carried through all somatic stem cell lineages throughout the life of the organism.

Blocking the interaction between p300 and catenin through the use of IQ-1, forces, for example, mouse ES cells to utilize CBP as its coactivator and thereby promotes CBP/catenin-driven maintenance of pluripotency and long-term expansion, and prevents spontaneous differentiation even in the absence of leukemia inhibitory factor (LIF). Similarly, knockdown of p300 in mES cells prevents spontaneous differentiation upon withdrawal of LIF from the media (31). Similar results upon selectively antagonizing the p300/catenin interaction have also been obtained with human ES cells (32; Hasegawa, K. et al. accepted Stem Cells Translation Medicine 2011). Blocking the CBP/catenin interaction with ICG-001 can prevent the induction of pluripotency, whereas selectively antagonizing the p300/catenin interaction can enhance reprogramming (33; present applicant unpublished data). These results are all consistent with applicant's model, wherein some catenin-transcriptionally regulated genes (e.g., Oct4, survivin) utilize only CBP as their coactivator, while others (e.g., Cdx2) selectively utilize p300 for transcriptional coactivation, whereas yet other catenin-regulated gene promoters are permissive and can utilize either CBP or p300 for productive transcription (17).

Figure 4:
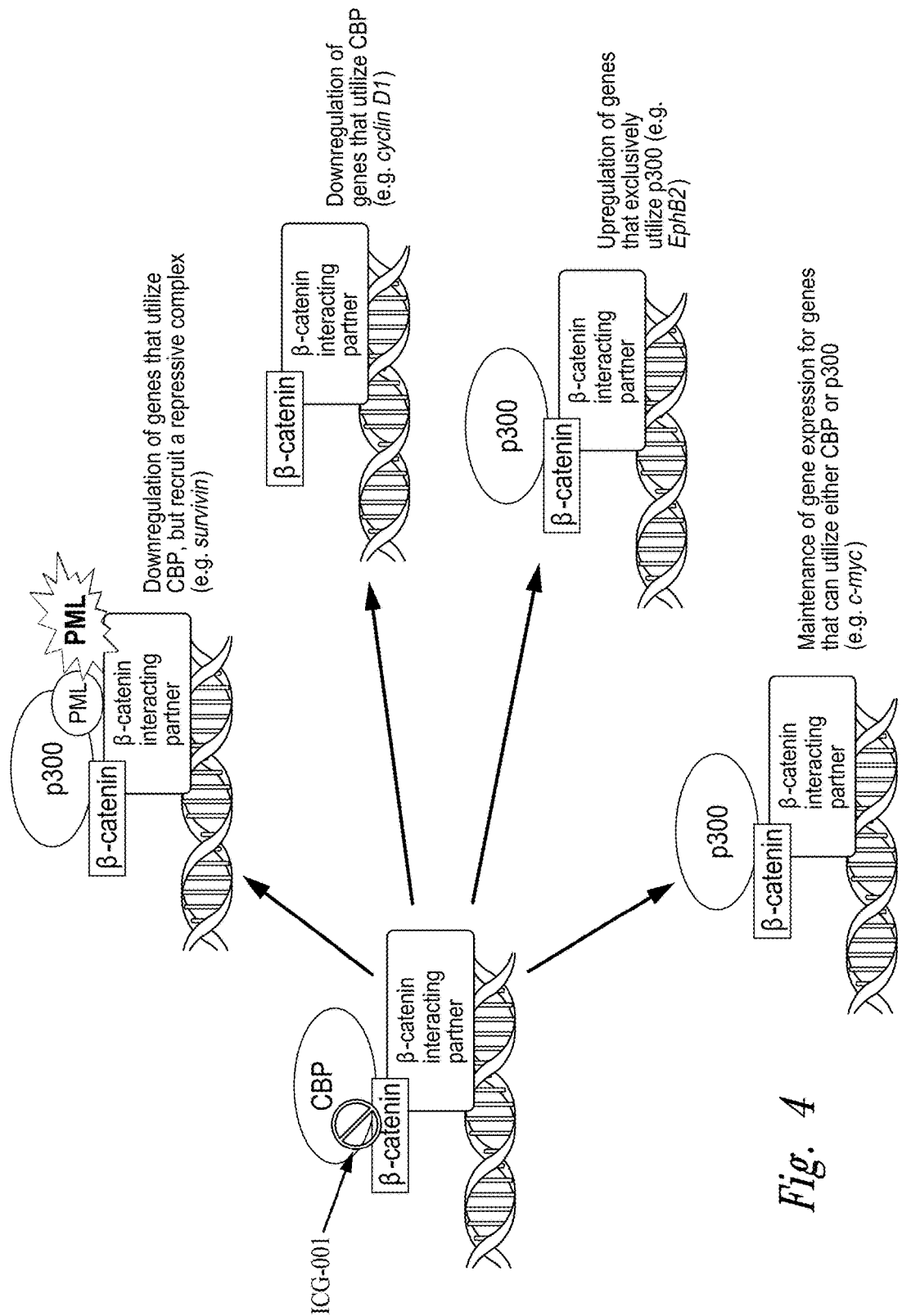
FIG. 4 shows a depiction of Four Potential Promoter Specific Outcomes due to Differential Coactivator Recruitment and Gene Expression. When the CBP/catenin interaction is antagonized by ICG-001, genes that can only utilize CBP for coactivation (e.g., cyclinD1 in colon cancer cells) are downregulated. Genes that are permissive (e.g., c-myc in colon cancer cells) utilize additional p300 to make up for the loss of CBP at their promoters. Genes that are p300 dependent (e.g., EpB2) become transcriptionally active with recruitment of p300 to their promoter. Some genes (e.g., survivin), after dismissal of CBP and a decrease in transcription, recruit a repressive complex to their promoter via p300, thus further shutting down gene expression.

The effects of CBP/catenin antagonism on Wnt target genes are highly promoter specific. Colorectal cancer cells were treated with ICG-001, thereby disrupting the CBP/catenin interaction, and then examined for coactivator occupancy at the promoter regions of several Wnt/beta-catenin regulated target genes using a Chromatin Immuno-precipitation Assay (ChIP), a technique that allows one to determine what proteins are associated with a particular promoter. At the cyclin D1 promoter, applicant observed dismissal of CBP, a decrease in message and no recruitment of p300 (23). At the c-myc promoter, applicant observed dismissal of CBP, a slight increase in message with increased p300 occupancy, whereas at the survivin promoter, applicant also observed decreased message with dismissal of CBP. Interestingly though, at the survivin promoter, applicant found increased recruitment of p300 along with additional proteins associated with transcriptional repression and the corresponding decrease in survivin message after ICG-001 treatment (17) (FIG. 4). In short, these results confirm that some Wnt/catenin-regulated genes (e.g., survivin) utilize only CBP as its coactivator for transcription, whereas other gene promoters are permissive and can utilize either CBP or p300 for productive transcription. Furthermore, there are other Wnt/catenin-regulated genes that selectively utilize p300 for transcriptional coactivation. An interesting example of this differential coactivator usage concerns the expression of the gene EphB2, a known Wnt/TCF/beta-catenin target gene. As almost 90% of colon cancers have high aberrant Wnt/TCF/ beta-catenin activation, it would follow that EphB2 expression would be increased with colon cancer disease progression. This, however, is not the case as EphB2 expression is generally lost in late stage colorectal cancers (34). Furthermore, disruption of EphB2 in the Min mouse, which carries a defective APC tumor suppressor gene, results in highly invasive carcinomas as opposed to the normal adenomas. What had been called a "conundrum", i.e., the disappearance of a direct Wnt target gene in colon cancer, a disease whose hallmark is aberrantly increased Wnt/catenin signaling, is relatively easily explained by the fact that the expression of EphB2 is p300/beta-catenin dependent and with colon cancer disease progression, there is increased biasing towards the use of the coactivator CBP in regards to Wnt/catenin signaling. In the event, antagonizing the CBP/catenin interaction through the use of ICG-001, colon cancer cells are forced to utilize p300 as their coactivator for Wnt/catenin signaling, thereby increasing the expression of EphB2 (35).

Figure 5:
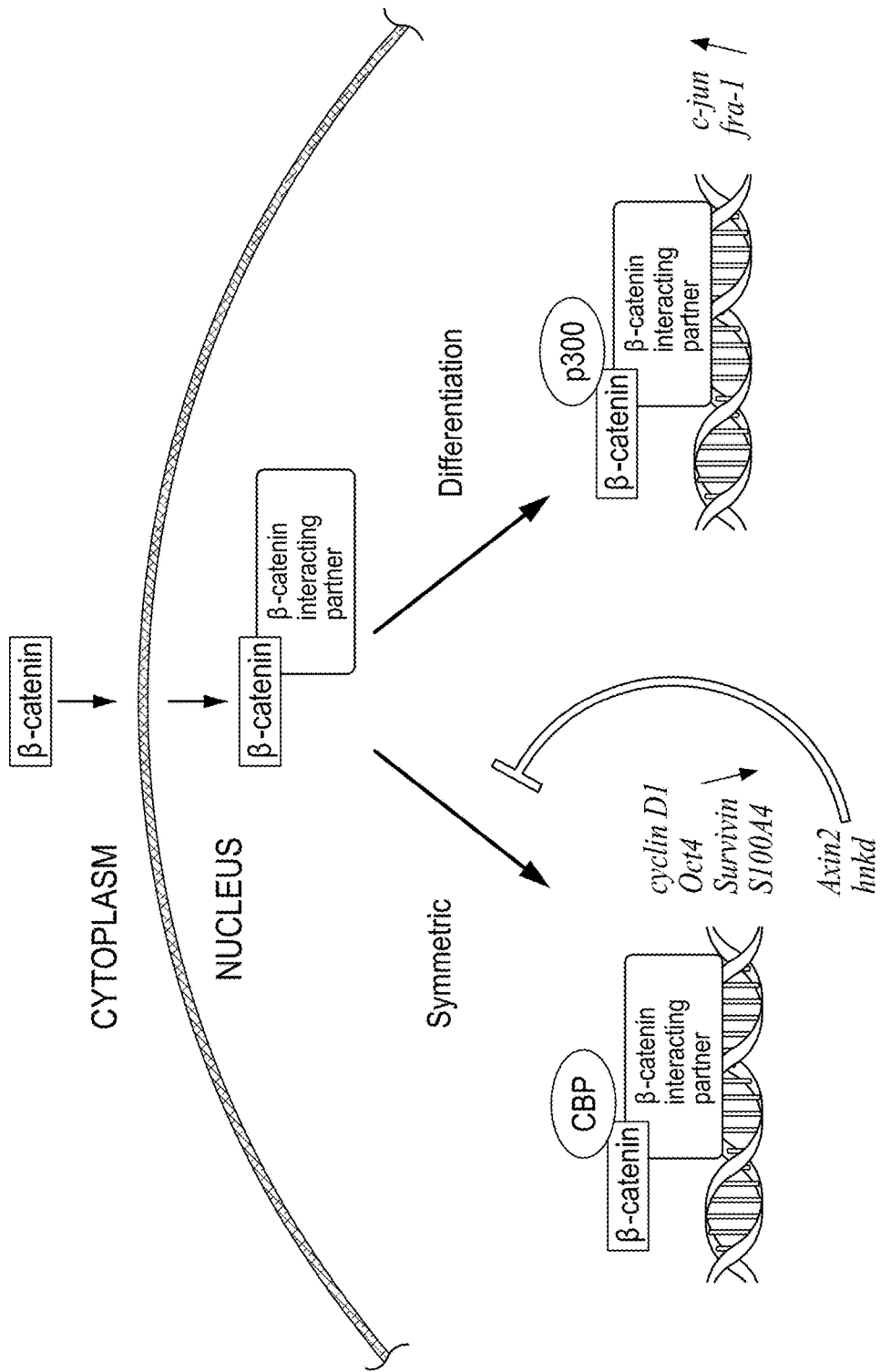
FIG. 5 shows a Negative Feedback Loop. Although maintenance of potency via CBP/catenin mediated gene transcription may be the default, some CBP/catenin regulated genes are part of a negative feedback loop that serves to turn off the CBP/catenin arm of the pathway, thus initiating the differentiation process via the p300/catenin arm.

An added level of complexity to this model is that although a subset of the gene expression cassette that is regulated by the CBP/catenin arm is critical for the maintenance of potency and proliferation (e.g., Oct4, survivin, etc.), other genes that are regulated in this manner (e.g., hNkd and axing) are in fact negative regulators of the CBP/catenin arm of the cascade (36, 37). This type of a negative feedback arm inherently makes perfect sense. Assuming potency and activation of the CBP/catenin arm is the default pathway, at some point, in order for development to proceed, one must stop proliferation, exit cell cycle divide asymmetrically and initiate the process of differentiation (FIG. 5). Interestingly, Axin2 expression is frequently silenced via DNA methylation in a wide array tumor types.

Another feature that emerged from applicant's work is that Wnt/CBP/catenin or Wnt/p300/catenin-mediated signaling is not exclusively TCF-dependent. Apart from TCF/LEFs, catenins, either beta or gamma, are also known to partner with a wide array of transcription factors, including members of the nuclear receptor family, Smads, Foxo, etc. (38-40). In this regard, the use of TopFlash—a reporter construct with multiple TCF binding elements driving a luciferase reporter gene—as the sine qua non functional readout for Wnt signaling is not accurate and furthermore, underestimates the total transcriptional role of nuclear catenin. Even in the absence of any TopFlash activity, nuclear beta catenin can still be transcriptionally active via partnering with TFs other than members of the TCF family (e.g., FOXO proteins) as TCFs are clearly not the only transcriptionally relevant binding partner for nuclear catenin. As a case in point, although our knowledge concerning the role of Wnt signaling in breast cancer is far from complete, its importance and significance has been the subject of numerous reports during the past 5 years (41). In human breast cancer, there are many reports of inactivation of negative regulators of the Wnt signaling pathway. Disheveled (Dsh), a downstream activator, is amplified and up regulated in 50% of ductal breast cancers [42]. Frizzled-related protein 1 (FRP1/FRZB), a secreted Wnt inhibitor, is frequently deleted in human breast cancers. In approximately 80% of malignant breast carcinomas, Frp1 expression is either repressed, or absent, making it one of the most frequent alterations in breast cancer (43). Axin exhibits frequent loss of heterozygosity (LOH) in breast cancers and is also downregulated in breast cancers (44, 45). Both are negative regulators of the canonical Wnt signaling pathway. Despite the fact that Wnt signaling clearly plays an important role in breast cancer, there is essentially no TopFlash activity in breast cancer cells.

Yet another issue that adds to the controversies surrounding this field, especially in regard to the use of genetic deletion of beta-catenin, is the ability of other catenins (e.g., gamma-catenin/plakoglobin) to at least partially compensate transcriptionally for the loss of beta-catenin. Even beta-gamma double knockout mice still exhibit Wnt signaling, which is functional at least in some tissues/organs (9, 46). Additionally, beta-catenin plays a critical role in cell-cell interactions at adherence junction. Therefore, the loss of beta-catenin can affect both its transcriptional role and its role in cell-cell interactions. Further adding to the complexity associated with Wnt/catenin signaling, is the fact that there are multiple mechanisms/pathways beyond the Wnt signaling cascade that can increase the nuclear translocation of beta-catenin, including numerous growth factors (TGF beta, EGF, HGF, etc.), kinases (e.g., Src, bcr-abl) and inactivation of adhesion molecules (e.g., E-cadherin) (*Front Biosci.* 2008 May 1; 13:3975-85. Microenvironmental regulation of E-cadherin-mediated adherens junctions. Giehl K, Menke A.)

Finally, although nuclear catenin is clearly critical for transcription, the absolute level may not be. Rather, the amount of transcriptionally competent catenin and its choice or balance of usage between the limiting amounts of the two coactivators (CBP and p300), is the ultimate deciding factor in the cells decision to divide symmetrically or asymmetrically. (35 and Ring, A. et al. Poster presentation ASCO 2011).

In summary, the selective pharmacologic tools ICG-001 and IQ-1 have proven invaluable for applicant's investigations. According to particular aspects of the present invention, using these tools, in conjunction with more traditional genetic knockouts or knockdowns, applicant has demonstrated that increased CBP/catenin-mediated transcription is associated with symmetric divisions, whereas p300/catenin mediated transcription is critical to initiate differentiation in a wide array of stem and progenitor cells in both rodents and humans.

Selective CBP/catenin antagonists: Is there a Natural Analog?

Figure 6:
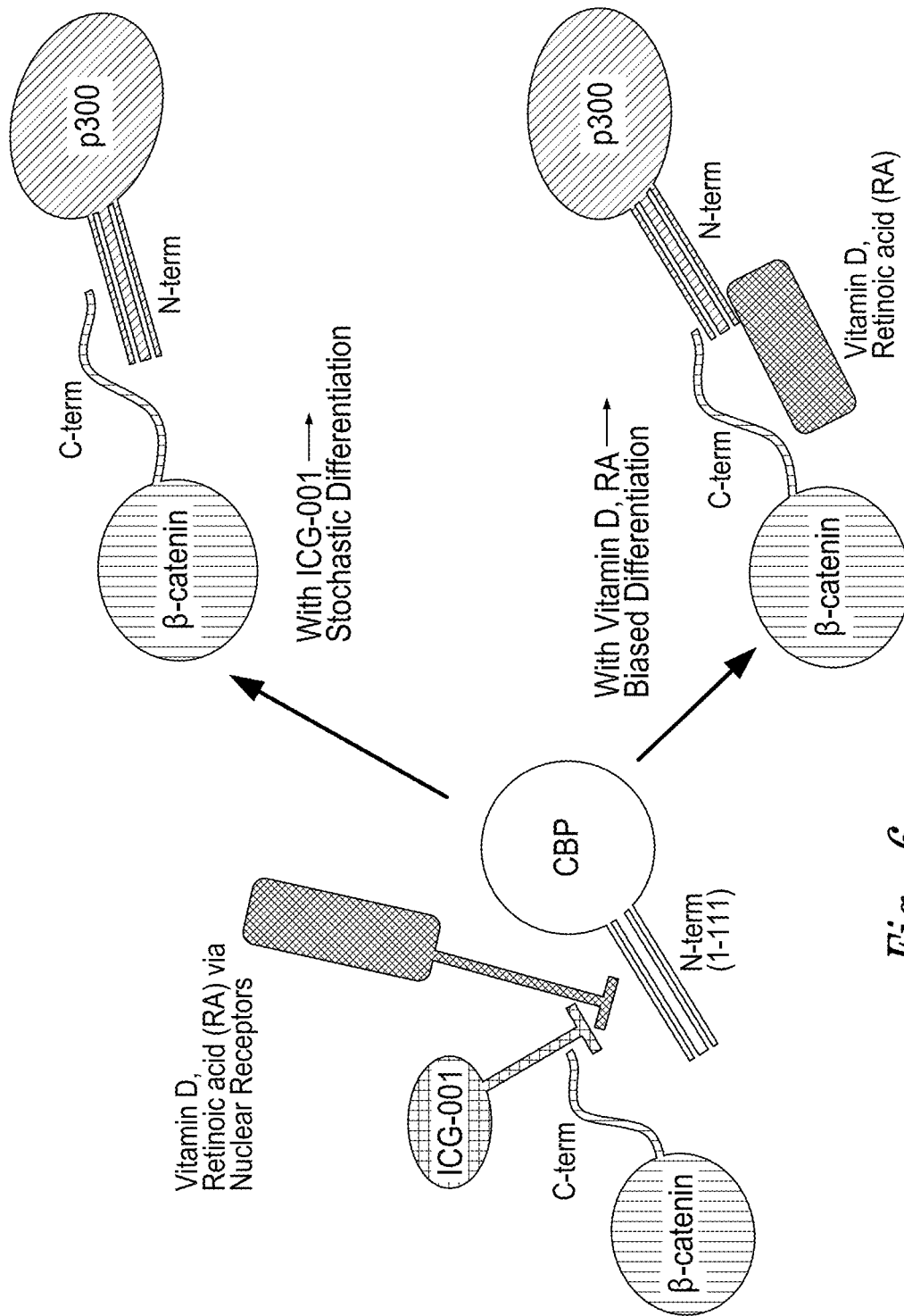
FIG. 6 shows a model depicting mechanistic overlap and differences between vitamin A & D (via their respective receptor complexes) and ICG-001.

Acute Promyelocytic Leukemia (APL) is unique among myeloid leukemias due to its sensitivity to all-trans retinoic acid (ATRA), a derivative of vitamin A. Treatment with ATRA dissociates the NCOR-HDACL complex from RAR and allows DNA transcription and differentiation of the immature leukemic promyelocytes into mature granulocytes by targeting the oncogenic transcription factor and its aberrant action. Unlike most other chemotherapies, ATRA does not directly kill the malignant cells but induces them to differentiate. A large number of scientific studies have also investigated a possible role for vitamin D in cancer prevention, including colon, prostate, breast, pancreatic and skin cancer. Interestingly both ATRA and Vitamin D, via their respective transcriptional complexes (RAR/RXR and VDR/RXR), can in some settings (e.g., colorectal cancer cells) antagonize aberrant Wnt signaling. However, there are also reports of synergistic effects on the activation of gene expression by ATRA and Wnt for example (47). Interestingly, an LXXLL sequence in the amino termini of both CBP and p300 can recruit these as well as other nuclear receptor signaling complexes (e.g., ER, AR and PPAR). This is the same region of these coactivator proteins (i.e., CBP and p300) that partners with catenin (both beta and gamma) and the CBP/catenin antagonists (e.g., ICG-001) also bind to this region. These nuclear receptor ligands have many of the same differentiating effects on stem cell populations that applicant has observed with specific CBP/catenin antagonists. Although, both Vitamin A and D are required during development and have many beneficial health effects in adulthood, both are teratogenic at high levels. Therefore, perhaps one of the most surprising findings during the course of our investigations of mouse development was that selectively antagonizing the CBP/catenin interaction with ICG-001, even at very high levels, appears to be extremely safe and had apparently no deleterious effects. Mice born from mothers treated topically with high doses of ICG-001 (0.5M) throughout pregnancy essentially from conception (~E0.5) to birth (~E20) at 6 weeks of age exhibited normal weight and size compared to their control littermates and could breed a second generation, testifying to the fact that there were no deleterious effects on germ cell populations. This is in dramatic contrast to selective antagonism of the p300/catenin interaction in utero, which causes dramatic defects in development in virtually every organ system investigated (i.e., vasculature, heart, lung, CNS, limbs etc.) (Kahn, unpublished). Based upon the data discussed above, applicant is proposing that agents like Vitamin A (ATRA) and Vitamin D are naturally occurring molecules that behave to some degree like applicant's small molecule CBP/catenin antagonists. They can antagonize the CBP/catenin interaction by binding to CBP, via their nuclear receptor complexes (i.e., RAR/RXR and VDR/RXR respectively). However, and very importantly, there are several major differences. CBP/catenin antagonists are direct (i.e., they bind directly to CBP and do not require any co-receptors, co-receptors are often decreased or silenced/lost in cancers) and pure CBP antagonists. Furthermore, they allow for stochastic differentiation (i.e., non-deterministic), whereas, Vitamin A or D, after antagonizing the CBP/catenin interaction, presumably via their lineage biasing agonistic properties, have deleterious effects at high doses on embryonic development (FIG. 6).

Therapeutic Applications of CBP/Catenin Antagonists

Cancer. The importance of Wnt signaling in colorectal cancer is undisputed. Applicant's investigation on the therapeutic utility of ICG-001 therefore quite naturally began with colon cancer. Applicant has shown that this compound down-regulated survivin. Survivin, is the number four transcript universally upregulated in cancer and is a known inhibitor of caspase activation and also important in cytokinesis. Increased caspase activation subsequent to survivin inhibition is manifested in selective cytotoxicity in colorectal cancer cells, but not in normal colonic epithelial cells. In vivo, ICG-001 is efficacious in both the Min mouse in reducing polyps and nude mouse SW620 xenograft model of colon cancer in reducing tumor growth (23).

According to particular aspects of the present invention, the similarities between normal adult somatic/tissue stem cells and cancer stem cells (CSC) suggest that the signaling pathways (e.g., Wnt, Hedgehog, and Notch) involved in regulating somatic stem cell maintenance are also involved in the regulation of CSCs (48-50). Aberrant regulation of these same pathways leads to neoplastic proliferation in the same tissues. Over the past few years, there has been growing evidence of the existence of cancer stem cells in leukemia, breast, lung, brain tumors, colon, prostate, and pancreatic cancers. These cancer stem cells possess similar markers and cellular behavior to somatic or tissue stem cells. CSCs are believed to be the cause of recurrence and metastasis. Within a tumor, the bulk is comprised of drug sensitive/differentiated cells and CSCs generally represent only a small percentage within the tumor. Current therapies are designed to kill the bulk of the drug-sensitive/differentiated cells but not the CSCs, which remain at least partially protected by multi-drug resistance genes, leading to recurrence and metastases. Recently, in a variety of CSC types, applicant has been able to demonstrate that by selectively inhibiting the interaction between CBP and catenin with ICG-001, the cancer stem cells can be forced to differentiate to what phenotypically looks and behave like the bulk of the tumor cell population, thereby sensitizing them to standard existing therapies. Within the context/scope of this disclosure, applicant will briefly highlight some of applicant's findings Breast cancer. Breast cancer stem cells, which have been identified by various phenotypic markers including Epithelial Specific Antigen/Epithelial Cell Adhesion Molecule (ESA/EpCAM), CD44, exclusion of Hoechst Dye (Side population (SP)), aldehyde dehydrogenase positivity (ALDH), and the absence of the cell surface antigen CD24 and lineage specific markers, can form tumors in animals with as little as 200 cells, followed by growth and differentiation that recapitulates the heterogeneity of the original tumor. Several developmental pathways, including Wnt, Notch and Hedgehog, are known to regulate the self-renewal of these stem cells. Alterations in each of these pathways can generate breast cancer in animal models and have been implicated in human breast carcinogenesis. However, pharmacological approaches to manipulate these pathways have been complicated by the multifunctional and divergent nature of the related networks, as evidenced by early results from Notch pathway inhibition, where abnormalities in normal maturation and differentiation were seen. Triple-negative breast cancer (ER, PR and Her2 negative) (TNBC) is a particularly aggressive subtype, with a higher risk of recurrence and mortality, higher predisposition for organ metastases as well as a lack of targeted therapeutic options against hormone and HER2 receptors. TNBC is biologically distinct as evidenced by stereotypic "basal" gene expression patterns, and most cases of breast cancers involving BRCA-1 mutations also fall within this subset. TNBC classification closely approximates the basal subtype of breast cancer defined by gene expression patterns similar to that of stem cells of the breast ductal epithelium. In one 190-patient study of basal cases defined by triple (ER, PR and HER2)-negativity as well as expression of cytokeratin 5/6, EGFR and vimentin, it was found that nuclear accumulation of beta-catenin, a classical readout of Wnt pathway activation, was enriched in the basal cases. Moreover, these cases that demonstrate increased beta-catenin levels, had a worse prognosis and were more frequent in African-American patients. Other studies have similarly shown that nuclear localization of beta-catenin is generally more common in triple negative patients.

The triple negative breast cancer cell line MDA-MB-231 exhibits low expression of the Wnt-regulated cell surface marker CD24, yet relatively high expression of another Wnt regulated target gene CD44. This phenotype $CD44^{hi}$, $CD24^{lo}$ has been associated with a subpopulation of cells that behave like a breast cancer stem/tumor initiating cell population (51). Interestingly, antagonizing the CBP/catenin interaction in MDA-MB-231 cells with ICG-001 significantly increased the expression of cell surface CD24 at 24h, while decreasing CD44 expression. Essentially, using ICG-001, we can force catenin to utilize the coactivator p300 thereby decreasing the expression of the Wnt/CBP/catenin target gene CD44 and concomitantly increasing the expression of the Wnt/p300/catenin target gene CD24 (a similar situation to the EphB2 conundrum discussed above) (Ring, A. et al. Poster presentation ASCO 2011). Furthermore, using ChIP (Identification of unknown target genes of human transcription factors using chromatin immunoprecipitation. Weinmann A S, Farnham P J. *Methods*. 2002 Jan; 26(1):37-47.), applicant demonstrated that ICG-001, by selectively blocking the CBP/catenin interaction, increased recruitment of p300 to the CD24 promoter. Blocking the CBP/catenin interaction with ICG-001 also dramatically decreases the side population (SP) and ALDH activity, both of which have been more generally correlated with stem/progenitor cell populations. Beyond reduction of survivin message level, there is a gene expression profile consistent with the occurrence of a mesenchymal to epithelial (MET) transition (i.e., decreased expression of twist, vimentin and S100A4 and an increase in E-cadherin expression). Recently, there have been a number of papers, which have correlated epithelial to mesenchymal transition (EMT) with a CSC phenotype (52). EMT is a normal physiologic process that is important in development and in adults, for example in wound healing, but pathophysiologically is associated with tumor metastasis and organ fibrosis (see later discussion on fibrosis). Specific CBP/catenin antagonists can reverse this aberrant EMT in vivo (EMT also plays a critical role in the skin in hair loss etc. J Dermatol Sci. 2011 Jan; 61(1):7-13. Epub 2010 Dec. 5; epithelial-mesenchymal transition (EMT) plays important roles not only in the morphogenesis but also in wound repair, tissue fibrosis and cancer progression. Recently, regulatory mechanism of this process has been elaborately elucidated. EMT can be a new therapeutic target for treating skin ulcer, fibrosing alopecia, and malignant cutaneous cancers, including squamous cell carcinoma and melanoma).

Interestingly, applicant has also demonstrated that antagonizing the interaction between CBP and catenin with ICG-001 causes the re-expression of the ER alpha receptor and subsequent sensitization to the anti-estrogen Tamoxifien. These results suggest that this strategy could be utilized clinically to eliminate via forced differentiation the breast cancer stem cell population and to induce the re-expression of estrogen receptor in triple negative breast cancers, thereby rendering them hormonally sensitive (Kahn, unpublished).

Chronic myelogenous leukemia (CML). Despite the stunning clinical success achieved to date in chronic phase CML patients treated with the BCR-ABL antagonist Gleevec/Imatinib (IM), responses in advanced phase patients are often short-lived, and patients invariably undergo disease progression. Furthermore, resistance to IM develops in 2% to 4% of patients annually and IM dose escalation is generally not sufficient to control the disease. Several mechanisms that contribute to tyrosine kinase inhibitor (TKI) resistance have been proposed including the insensitivity of quiescent CML stem cells to TKIs due to low expression of BCR-ABL and the emergence of drug resistant leukemic clones associated with increased nuclear catenin levels, a hallmark of increased Wnt/catenin transcription. Interestingly, many Wnt signaling related genes are upregulated in CML, in particular in association with disease progression (53). Epigenetic silencing of negative regulators of the Wnt signaling cascade is also frequently associated with leukemias, including CML. Recently, Applicant has demonstrated that the imatinib resistant (IR) CML population exhibits characteristics consistent with a quiescent leukemia stem cell population and that the specific small molecule inhibitor ICG-001, by inhibiting the interaction between CBP and catenin, both $\beta$ and $\gamma$ (9), induces the differentiation of the IR cells both in vitro and in vivo. Specifically, using a highly immunocompromised (NOD/SCID/IL2r$\gamma^{-/-}$) mouse model of engrafted human CML, applicant demonstrated that by specifically inhibiting the interaction between CBP and catenin with the small molecule ICG-001, drug resistant leukemia stem cells can be eliminated. Importantly, this can be done without deleterious effects to normal endogenous hematopoiesis (i.e., not damaging the normal hematopoietic stem cells (HSC)). The mice treated with one course (28 days from day 13-41 after leukemia engraftment) of CBP/catenin antagonist plus bcr-abl antagonist are essentially cured of leukemia and live as long (approximately 2 years) as their littermates that were never engrafted with leukemia.

According to specific aspects of the current invention, specific CBP/catenin antagonism can eliminate CSCs via forced differentiation without deleterious effects on the normal endogenous stem cell populations.

Fibrosis. Idiopathic pulmonary fibrosis (IPF)/usual interstitial pneumonia (UIP), the most common of the idiopathic interstitial pneumonias, is a devastating, progressive disorder characterized by excessive fibroblast proliferation and extracellular matrix remodeling leading to lung destruction. There is currently no effective therapy for this uniformly fatal disease. An emerging paradigm proposes a central role for alveolar epithelial cell injury and dysregulated repair in the pathogenesis of IPF. Injury to the epithelium is thought to initiate a cascade of fibroblast activation and matrix deposition, which in predisposed hosts fails to resolve as it would in the course of normal wound repair. Epithelial cells undergo excessive apoptosis, whereas fibroblasts are less amenable to apoptosis and manifest increased survival. The well-characterized model of bleomycin-induced lung injury has been extensively used to investigate potential pathways involved in the pathogenesis of pulmonary fibrosis and to explore therapeutic approaches. Despite some limitations with regard to recapitulation of human disease, a number of pathways that are up-regulated in IPF (e.g., TGF-$\beta$ and Wnt/$\beta$-catenin) are also up-regulated following bleomycin. Utilizing transgenic BAT-gal mice, applicant demonstrated that aberrant activation of Wnt signaling in the lungs is induced after insult. Intranasal administration of bleomycin caused marked lacZ expression in the airway and alveolar epithelium of BAT-gal transgenic mice, which was significantly reduced by the specific inhibitor of Wnt/beta-catenin/CBP-driven transcription, ICG-001. Bleomycin treatment also dramatically increased expression of a number of genes specifically associated with fibrosis, ECM deposition, and EMT (e.g., S100A4, MMP-7, CTGF, collagen types I and III, fibronectin, and TGF-$\beta$1) several of which are known Wnt/beta-catenin target genes. Treatment with ICG-001 reduced the expression of these genes essentially to the level of control. Recent evidence suggests a significant role for EMT in fibrosis following administration of bleomycin treatment. ICG-001 significantly decreased the expression of S100A4/FSP-1 both in the bleomycin-induced fibrosis model in vivo in the mouse and in fibroblasts from IPF patients in vitro. S100A4/FSP-1 has been suggested to be a hallmark of EMT that may represent a common pathway in diseases marked by airway remodeling. According to particular aspects, the reduction in S100A4/FSP-1 expression via CBP/beta-catenin antagonism to be associated with MET. Furthermore, applicant demonstrated in vitro using rat type II lung epithelial cells that ICG-001 prevents the TGF-$\beta$1-induced up-regulation of $\alpha$-SMA and type I collagen, genes that are typically increased in EMT. Importantly, regardless of the mechanism of activation and translocation of catenin to the nucleus (i.e. 1 Wnt or TGF-beta etc.), ICG-001 can selectively antagonize the aberrant transcriptional CBP/catenin activity associated with EMT. In vivo ICG-001 pretreatment significantly reduced the severity of pulmonary fibrosis. In marked contrast, although administration of dexamethasone (1 mg/kg per day) for the same 10-d period significantly reduced the inflammatory cell infiltrate, interstitial and alveolar fibrosis were unaffected, consistent with prior reports of failure of corticosteroids to ameliorate pulmonary fibrosis in either animal models or patients with lung fibroproliferative disorders. Even more importantly, ICG-001 could reverse established fibrosis in the mouse model (54).

Alzheimer's disease. Alzheimer's disease (AD) is the most common form of dementia in the elderly. AD patients demonstrate a gradual and hierarchical decline in cognition, learning and memory. These symptoms have been correlated with the accumulation of extracellular neuritic plaques composed of fibrillar β-amyloid (Aβ) peptide, intracellular neurofibrillary tangles containing hyperphosphorylated tau and neurodegeneration. Although significant effort has been devoted to link these seemingly independent phenomena with the progression of AD, it is possible that these are distinct manifestations of a common underlying defect in neuronal homeostasis and plasticity. Presenilin-1 (PS-1), mutation of which are associated with early onset familial Alzheimer's disease (FAD), has been shown to interact with members of the armadillo family of proteins including beta-catenin, providing a potential link between Wnt signaling and AD pathology.

Figures 7A, 7B:
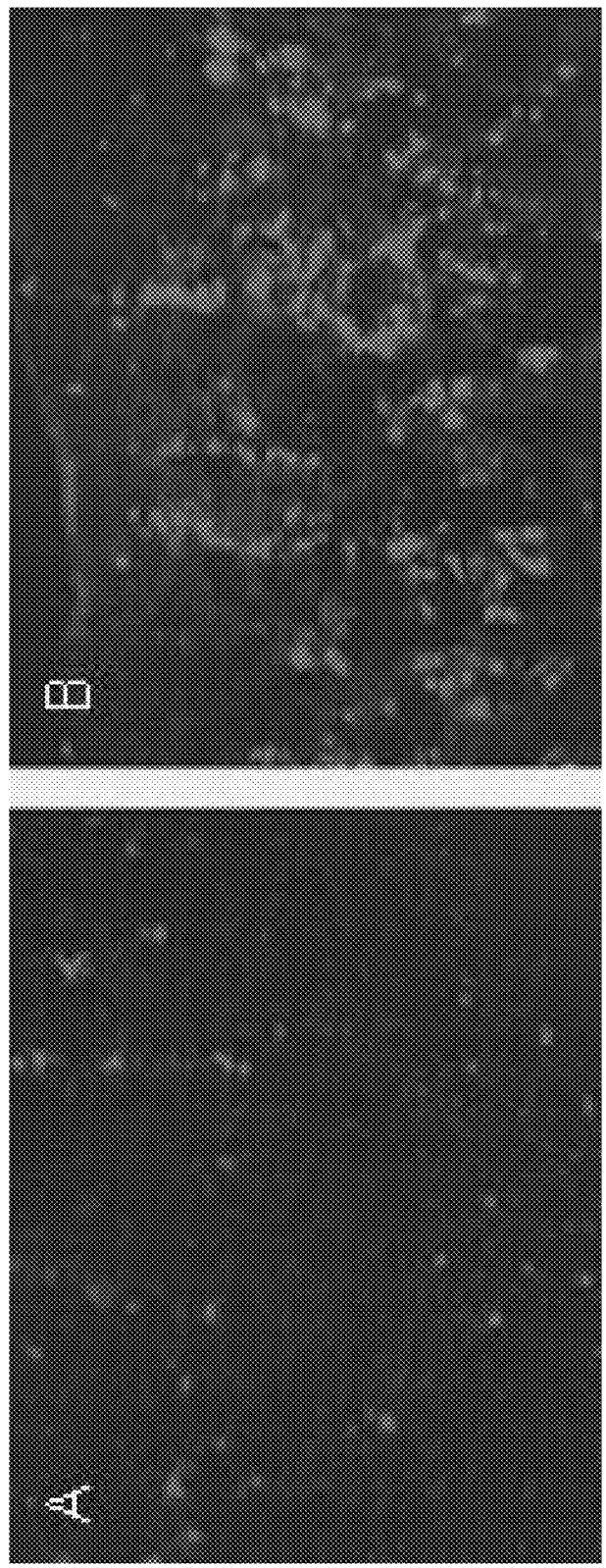
FIG. 7 shows Aβ Deposition in a Mouse Model of Alzheimer's Disease. Applicant utilized a penta-transgenic mouse model of AD, which normally develops massive cerebral deposition of Aβ starting at 6 weeks of age. These mice were treated with either (A) ICG-001 (50 mg/kg/day) or (B) saline for 2 months. There was a significant (A) decrease in Aβ staining in the parietal lobe of the ICG-001 treated group compared with (B) the intense Aβ staining in the saline control-treated group.

However, the effects of PS-1 mutations on the stability of beta-catenin, TCF/beta-catenin signaling, and thereby its potential role in AD remain controversial. Applicant has shown that introduction of a FAD mutant PS-1 (L286V) into PC-12 cells causes increased TCF/beta-catenin signaling, leading to the inhibition of neurite outgrowth. Treatment of these mutant cells with ICG-001, by specifically inhibiting CBP/beta-catenin-mediated transcription, rescues the defects in neuronal differentiation and neurite outgrowth in these cells. Importantly, the expression of critical markers of neuronal development (i.e., GAP43) is dramatically increased in the mutant cells treated with ICG-001 during NGF-induced differentiation compared with untreated cells. Interestingly, EpB2 expression, as it is in colorectal cancer cells, is again increased by antagonizing the interaction between CBP and catenin with ICG-001. In the CNS, EpB2 expression is associated with axonal guidance (16). Furthermore, a recent study demonstrated decreased EpB2 expression is found to decrease with AD disease progression contributing to glutaminergic synaptic deficits (similar situation to colon cancer described above). In a mouse model of AD, increasing the expression of EpB2 had a beneficial effect on memory consolidation (55). In initial in vivo studies, applicant treated penta-transgenic mice that over express mutant APP (695) (Swedish (K670N, M671L), Florida (I716V) and London (V717I)) and PS-1 (M146L and L286V) mutations with ICG-001 for 2 months (months 2-4). These mice normally develop massive cerebral deposition of Aβ starting at 6 weeks of age. In the ICG-001 treated group (3 mice at 50 mg/kg/day) there was a significant decrease in amyloid plaque formation compared to saline treated control as judged by immunohistochemistry (FIG. 7).

The efficacy of antagonizing the CBP/catenin interaction in these highly divergent disease models, and others that we have not discussed (including post-myocardial infarction, multiple sclerosis, etc.) is extremely exciting. However, it begs the question of how is it possible that one compound can possibly have beneficial therapeutic effects in such highly divergent tissues/organs and disease models. Equally important, CBP/catenin antagonists have proven extremely safe in preclinical evaluation in multiple species and in particular have not had any apparent deleterious effects on the normal endogenous stem cell populations.

Symmetric Versus Asymmetric Division in Somatic and Cancer Stem Cells

Based in part upon the results described above, it occurred to applicant that the differential effects of CBP/catenin antagonists on cancer stem cells versus normal somatic stem cells (i.e., forced differentiation and elimination versus differentiation enhanced repair without apparent depletion) were apparently cell intrinsic and not due to the selective targeting by CBP/catenin antagonists of CSC versus normal somatic stem cells. According to particular aspects, applicant therefore hypothesized that CBP/catenin antagonists take advantage of the intrinsic propensity of cancer stem cells to increase their number of symmetric divisions at the expense of asymmetric divisions due to various mutations (e.g., p53, PTEN), whereas normal endogenous stem cells preferentially divide asymmetrically with one daughter cell remaining in the niche and the other going on to a transient amplifying cell required for generating the new tissue involved in repair processes. Interestingly, the choice of whether the symmetric divisions are renewing (i.e., maintain the same level of potency) or whether they are differentiative symmetric divisions (i.e., both cells go on to a less potent state) seems to be correlated with CSC versus non-CSC stem cell populations respectively.

Figure 8:
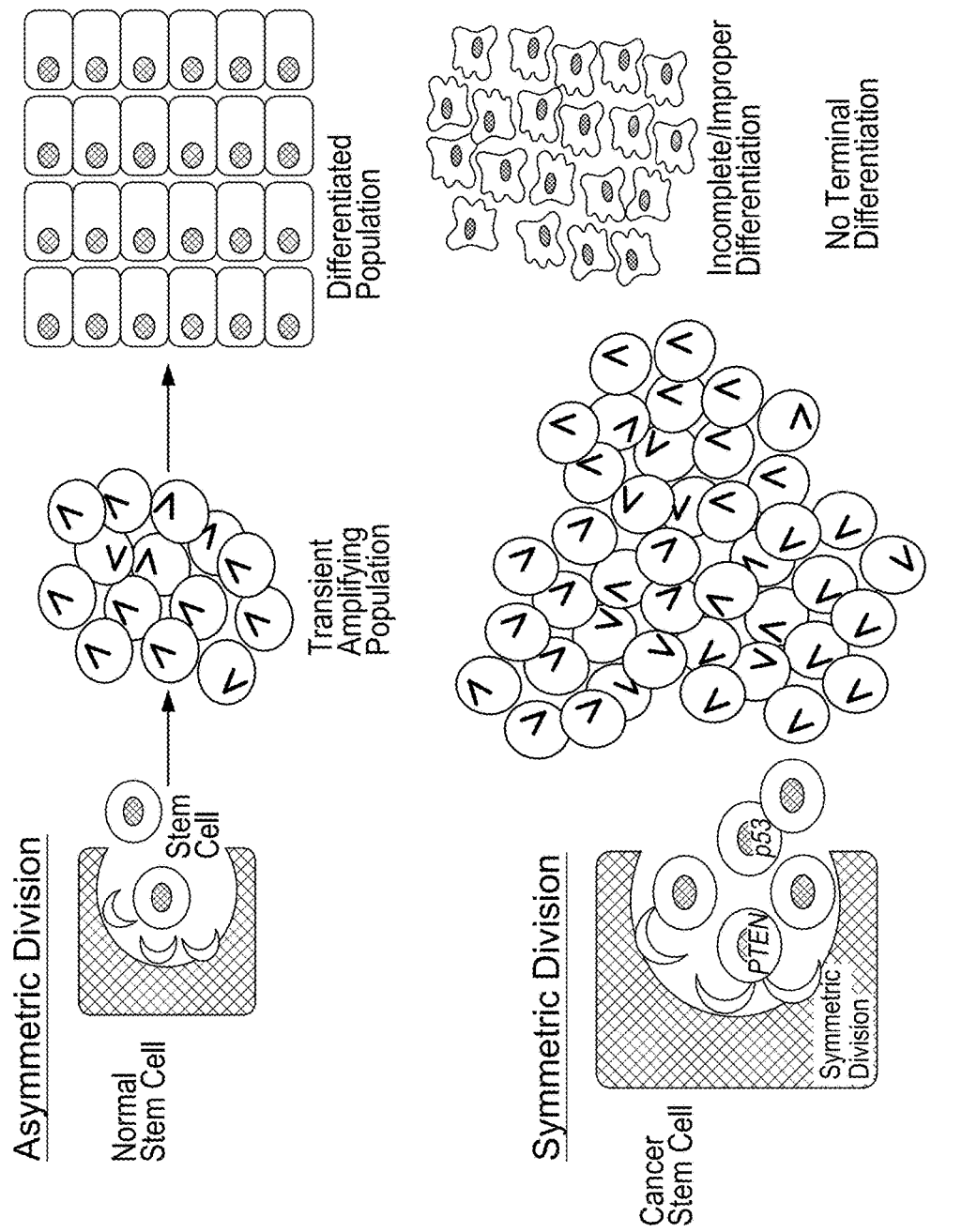
FIG. 8 shows a model depicting the intrinsic difference between normal somatic stem cells and cancer stem cells in regards to symmetric versus asymmetric division.

According to particular aspects, CBP/catenin antagonists (e.g., ICG-001 and other CBP/beta-catenin antagonists as disclosed herein) enforce a differentiative symmetric division on the tumor stem cell population thereby eventually depleting the tumor stem cells from their niche. In sharp contrast, according to particular aspects, in the case of normal somatic stem cells, CBP/catenin antagonists allow for asymmetric divisions and in cases where quiescent somatic stem cells need to be activated to increase repair, CBP/catenin antagonists can enhance or accelerate this process (FIG. 8, top half). This hypothesis is not easily tested using engrafted leukemic stem cells and applicant therefore turned to an exemplary neurogenesis model that has been utilized previously to study symmetric versus asymmetric cell division.

Taking advantage of the ready uptake and penetration through the placental barrier of applicant's small molecule Wnt modulators, applicant designed a series of experiments to investigate symmetric versus asymmetric divisions in the ventricular zone (VZ) of the brain during mouse embryonic development. Timed pregnant mice were topically treated for various time periods (1-3 days) with DMSO (vehicle control), the CBP/catenin antagonist ICG-001 or the p300/catenin antagonist IQ-1. Using a previously described protocol (56), the localization of Polarity Associated Protein 3 (Par3) and DNA was examined in mitotic cells in the VZ. Par3 distributes symmetrically in cells that divide symmetrically and asymmetrically in cells that divide asymmetrically, whereas the DNA distributes symmetrically between the 2 cells. Using fluorescence microscopy, the percentage of mitotic cells dividing symmetrically or asymmetrically could be quantified. For example, after treatment for 1 day during the neurogenic period of development (E13.5 to 14.5) with DMSO, applicant found that approximately 21% of the divisions in the VZ were asymmetric. Antagonizing the CBP/catenin interaction with ICG-001 had no apparent effect yielding similarly, approximately 21% asymmetric divisions. In sharp contrast, treatment with the p300/catenin antagonist IQ-1, thereby increasing the CBP/catenin interaction, significantly decreased the number of asymmetric divisions to approximately 9%. Importantly, this decrease in asymmetric divisions upon treatment with IQ-1 could be rescued back essentially to control levels (i.e. ~21%) by treatment with a 2-fold excess of ICG-001. Even further divergence in symmetric versus asymmetric divisions could be seen upon prolonged treatments. For example, treatment with IQ-1 (i.e., antagonizing p300/catenin interaction leading to increased usage of CBP) for 3 days (E13.5-16.5) decreased asymmetric divisions compared to control from 31% to 7%. Interestingly, it was found that the increased symmetric divisions induced by p300/catenin antagonism by IQ-1 in normal neural stem cells resulted in an increase in the number of symmetric differentiative divisions as judged by both an increase in the subventricular zone (SVZ) at the expense of the VZ and also by the number of neurogenic differentiative divisions as judged by the transgenic Tis21 reporter mice and the number of neurogenin2 (a marker of terminal mitosis) positive cells). This reporter mouse expresses EGFP, driven by the Tis21 promoter, in cells that have undergone neurogenic differentiative divisions.

This increase in symmetric differentiative divisions was at first surprising given that in vitro, IQ-1 increases the number of symmetric non-differentiative divisions both in mES cells and epicardial progenitors (24, 57). In retrospect, this is quite consistent with the difference previously observed in mouse knockout models (for example PTEN in the HSC population versus LSC) (58) and how they affect the normal stem cell population, i.e., premature exhaustion, presumably due to increased symmetric differentiative divisions and elimination of the stem cell population versus the transformed tumor stem cell population, which increases due to increased symmetric non-differentiative divisions.

Rationale for Divergence of Symmetric Renewing Versus Symmetric Differentiating Divisions in CSC Versus Normal Somatic Stem Cells The data described above clearly demonstrate that increased CBP/catenin transcription at the expense of p300/catenin transcription increases the number of symmetric divisions at the expense of asymmetric divisions (both in vitro and in vivo). However, the decision for the symmetric division to be differentiative or non-differentiative involves other additional inputs—both intrinsic and extrinsic—to the cell. Furthermore, in a normal somatic stem cell, it appears that attempts to force symmetric divisions in vivo often leads preferentially not to an increase in the number of renewing, non-differentiative divisions and hence an increase in the stem cell pool, but rather to enhanced symmetric differentiative divisions and thereby premature depletion of the somatic stem cell population. A potential rationale for this observation goes back to the "Immortal Strand Hypothesis) described more than 35 years ago by Cairns (59). Stated simply, stem cells when they undergo mitosis desire to retain the original uncopied strands of DNA and pass on the duplicated strands that contain multiple copy errors to the daughter cell that will continue on a path towards terminal differentiation. In this way, the total number of DNA mutations in the long lived stem cell populations in the niche, which are retained throughout the lifetime of the organism, are minimized. This would appear to be an inherent defense mechanism to protect the stem cell population, particularly in long lived organisms, and allow for long term fidelity of maintenance and repair of tissues and organ systems. In sharp contrast, transformed stem cells appear to have overcome this inherent safeguard, through combinations of mutations (e.g., p53, PTEN, KRAS etc.) either inherited or acquired, and preferentially undergo symmetric non-differentiative divisions, thereby increasing the stem cell pool with cells that carry DNA mutations, thereby overtime decreasing genomic stability and the fidelity of repair and maintenance.

However, this intrinsic protection mechanism against normal tissue stem cell symmetric renewing divisions is by no means fool proof and may be subverted by multiple factors e.g. genetic mutations, inherited and acquired, various insults (radiation, infection, dietary xenobiotics, etc.), chronic inflammation etc., thereby with aging leading to the observed increase in the number of stem cells in many somatic stem cell populations. More recently, it has also become clear that the decision process/point for renewal versus differentiation (i.e., maintain a level of potency or decrease a level of potency) is also reversible; induced pluripotent stem (iPS) cells demonstrating this most clearly, as well as much earlier work on transformation/immortalization of cells. This plasticity needs to be factored in to the hypotheses regarding the origins of cancer stem cells; that is, are CSCs derived from mutations to the normal somatic stem cell itself; or are mutations occurring in a more differentiated (transient amplifying) progenitor that reprograms the progenitor to a more "stem-like" status? These are not mutually exclusive and in terms of therapeutic strategies to target CSCs, essentially only a semantic argument.

Symmetry Versus Asymmetry and Aging

According to particular aspects of the present invention, as we age, both the fidelity and the efficiency of our bodies homeostatic and repair processes decrease. Although, in principle this could be due to a decline in the tissue stem cell populations required to drive homeostasis and repair, according to particular aspects, rather than a decline in the tissue stem cell populations (HSC, skin/hair, etc.), there is an increase in the number of somatic stem cells. However, according to further aspects, the "effectiveness" of these stem cells to serve as a regenerative pool during homeostasis and repair decreases with age. Interestingly, several mouse models of premature aging and decreased effectiveness of repair after injury (i.e., increased fibrosis) have demonstrated an increase in Wnt signaling (60-62).

Figure 9:
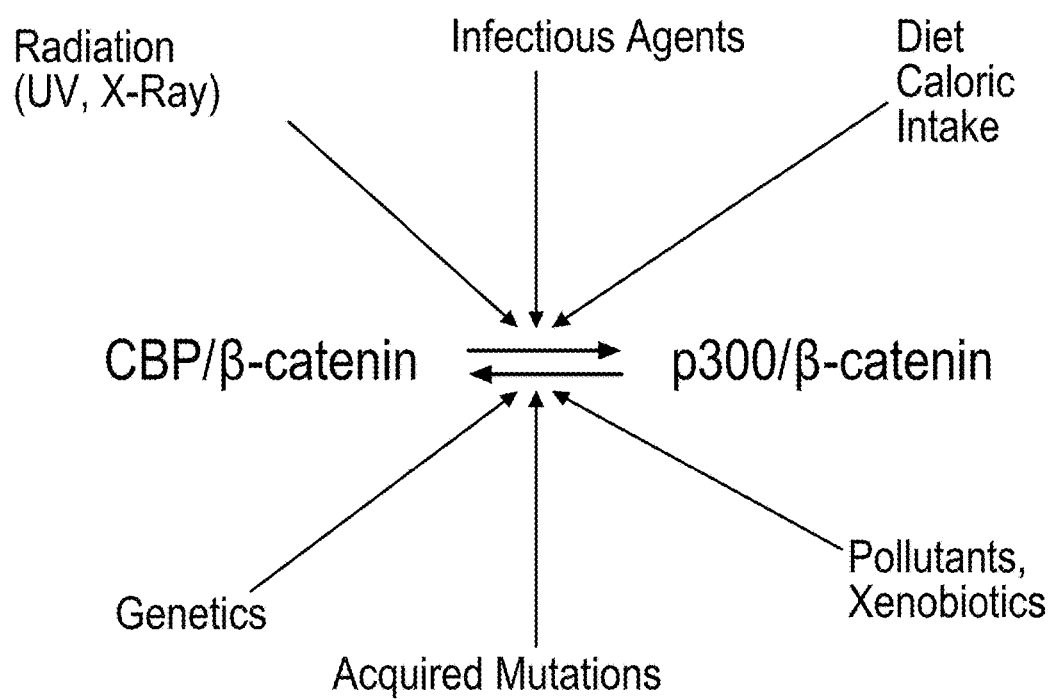
FIG. 9 shows a critical equilibrium. Potential insults that can affect the critical equilibrium between catenin and CBP or p300 usage during the aging process.

According to particular aspects, applicant interprets this increase in the stem cell pool with decreased efficacy in homeostatic processes as arising from an increase in the number of symmetric renewing divisions at the expense of asymmetric divisions in the stem cell population (e.g., somatic stem cell populations). According to further aspects, this arises from an increase in the CBP/catenin interaction/transcription at the expense of the p300/catenin interaction/transcription with aging. This also fits with epidemiologic data which demonstrates that the risk of developing cancer, fibrosis or neurodegeneration increases significantly with age after age 50. According to particular aspects, this increase in stem cell symmetric versus asymmetric divisions with age could be engendered and/or influenced by a variety of factors including genetics, various insults (infection, xenobiotics, pollutants, etc.), diet/caloric intake/metabolism, radiation (UV, X-Ray), which in combination could bias the equilibrium between CBP/catenin and p300/catenin driven transcription leading to an increase in CBP/catenin driven processes and an increase in symmetric versus asymmetric divisions in the effected somatic stem cell populations (FIG. 9).

According to particular aspects, therefore, selective small molecule CBP/catenins (e.g., CBP/beta-catenin) antagonists have substantial utility to correct this biasing, thereby providing a more optimal (youthful) balance in asymmetric versus symmetric divisions; that is, providing for increasing the number of asymmetric renewing divisions at the expense of symmetric divisions in the stem cell population (e.g., somatic stem cells), wherein a method for treating aging or a disease/condition of aging or at least one symptom thereof is afforded.

According to particular aspects, small molecule CBP/catenins (e.g., CBP/beta-catenin) antagonists have substantial utility to ameliorate the aging process, and/or manifestations thereof.

According to particular aspects, small molecule CBP/beta-catenin antagonists have substantial utility to provide prophylaxis against common diseases and conditions of aging (e.g. cancer, fibrosis, neurodegeneration, hair loss, skin/tissue degeneration/degradation, etc.).

The ultimate decision for a cell to retain potency or initiate differentiation is dependent upon numerous inputs including the activation of different growth factors, cytokines, and hormones and the subsequent activation of different signal transduction complexes and kinase cascades, nutrient levels, oxygen levels, genetic mutations, adhesion to substratum, etc. In the end these multiple pathways must be integrated and funneled down into a simple decision point, i.e., a 0/1 binary decision. According to particular aspects, the equilibrium between CBP-mediated and p300-mediated catenin transcription plays a central role in integrating these signals.

According to particular aspects, cancer, rather than being many etiologically different diseases (i.e., breast cancer is different from colon cancer, is different from leukemia, etc.), represents tissue-specific stem cell aberrations, associated with many combinations of different mutations (some of which may be tissue specific) (e.g., bcr/abl, K-Ras, Her2, etc.) that can lead to aberrant regulation of the underlying equilibrium between catenin/CBP and catenin/p300, i.e., between proliferation and maintenance of potency and the initiation of differentiation or alternatively between symmetric versus asymmetric division.

Although we know how to pharmacologically manipulate the balance of differential catenin coactivator usage (i.e., catenin/CBP versus catenin/p300) in stem/progenitor cell populations, we have only begun to understand how a cell reads the enormously complex array of information from its environment (e.g., oxygen levels, nutrient levels, light/dark, i.e., circadian cycles, growth factors, adhesion molecules, cell/cell contacts, etc.) to arrive at the eventual 0/1 binary decision.

Figure 10:
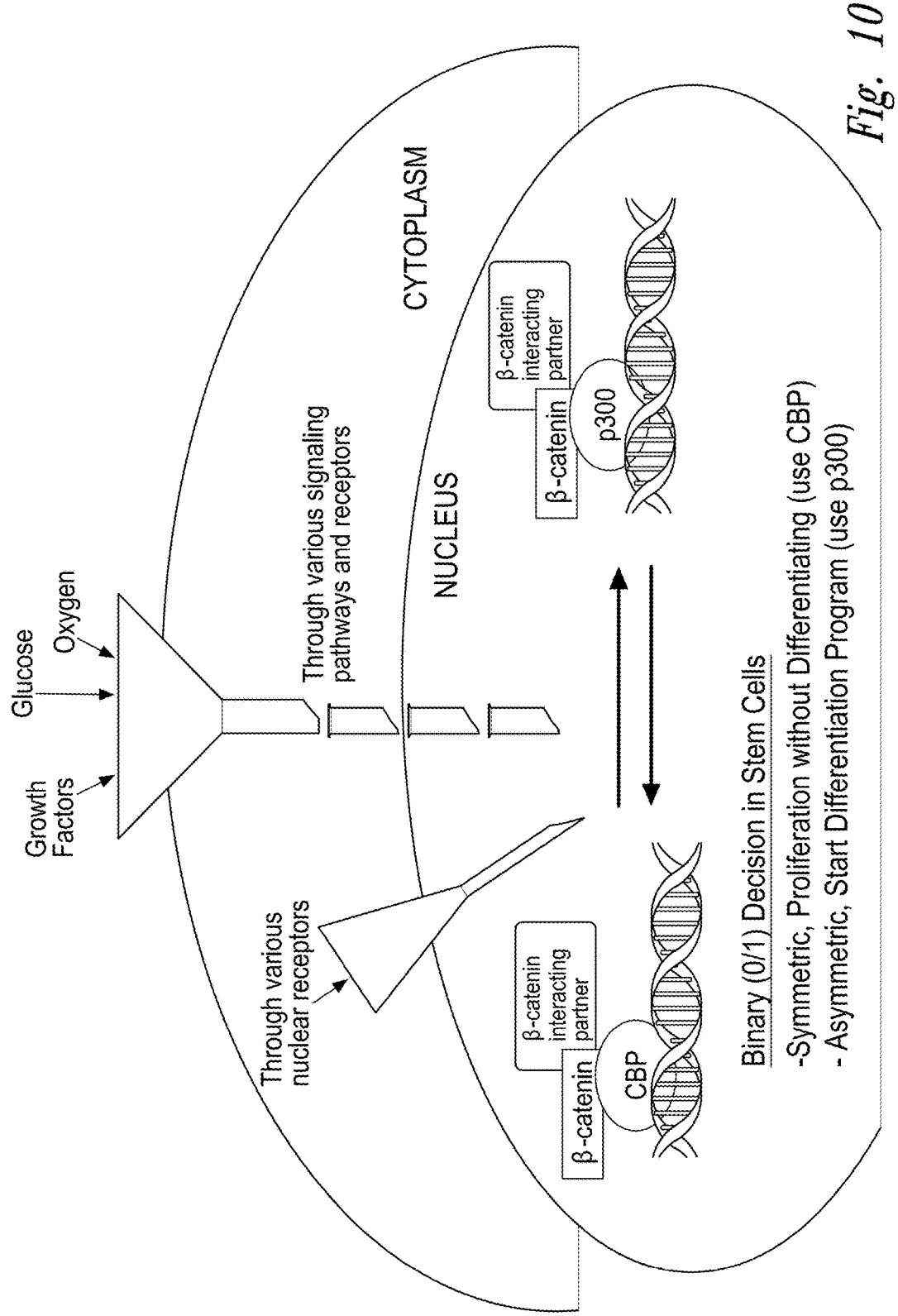
FIG. 10 shows Funnel to Binary Decision in Stem Cells. All inputs that a stem cell receives—regardless of the signaling pathways or receptors that are utilized—are ultimately 'funneled down' to the critical binary decision of using either CBP or p300 as the coactivator for catenin.

According to particular aspects, FIG. 10 depicts Applicant's model for the "funneling down" of information through various kinase cascades that play a major role in determining the binary decision to symmetrically or asymmetrically divide via controlling the balance between the CBP/catenin interaction and the p300/catenin interaction. The rapid and reversible (via phosphatases) ability of kinase cascades to modulate protein/protein interactions offers a very versatile and facile mechanism to modulate this critical binary switch. Interestingly, within the first 111 amino acid residues of CBP and p300 there are 20 serine and threonine residues. This coupled with additional points for posttranslational modification (e.g., lysine acetylation) and recruitment of differential epigenetic modifiers provides ample opportunities for the fine tuning required to regulate critical expression cassettes associated with symmetric versus asymmetric division and self-renewal or differentiation.

These studies, in conjunction with preclinical models to evaluate the role of this critical switch in a range of devastating diseases (e.g., AD, Parkinson's, MS, pulmonary hypertension, etc.) and to pharmacologically intervene with small molecule CBP/catenin antagonists, as well as with more generic health problems such as metabolic syndrome and aging provide new methods of treatment.

References for this sectION (Incorporated by Reference Herein for their Relevant Teachings)

1. Nemeth M J, Mak K K, Yang Y, Bodine D M. beta-Catenin expression in the bone marrow microenvironment is required for long-term maintenance of primitive hematopoietic cells. *Stem Cells.* 27, 1109-1119 (2009).
2. Malhotra S, Kincade P W. Wnt-related molecules and signaling pathway equilibrium in hematopoiesis, Cell Stem Cell. 4, 27-36 (2009).
3. Monga S P. Role of Wnt/beta-catenin signaling in liver metabolism and cancer. *Int J. Biochem Cell Biol.* (2009) Sep. 9 [Epub ahead of print]
4. Inestrosa N C, Arenas E. Emerging roles of Wnts in the adult nervous system. *Nat. Rev. Neurosci.* 11, 77-86 (2010).
5. de Lau W, Barker N, Clevers H. WNT signaling in the normal intestine and colorectal cancer. *Front Biosci.* 12, 471-491 (2007).
6. Kohn A D, Moon R T. Wnt and calcium signaling: beta-catenin-independent pathways. *Cell Calcium.* 38, 439-446 (2005).
7. Logan C Y, Nusse R. The Wnt signaling pathway in development and disease. *Ann Rev Cell Dev Biol.* 20, 781-810 (2004).
8. Angers S, Moon R T. Proximal events in Wnt signal transduction. *Nat. Rev. Mol. Cell. Biol.* 10, 468-477 (2009).
9. Kim Y M, Ma H, Oehler V G et al. The gamma catenin/CBP complex maintains survivin transcription in β-catenin deficient/depleted cancer cells. *Curr Cancer Drug Targets.* 11, 213-225 (2011).
10. Kung A L, Rebel V I, Bronson R Y et al. Gene dose-dependent control of hematopoiesis and hematologic tumor suppression by CBP. *Genes. Dev.* 14, 272-277 (2000).
11. Yamauchi T, Oike Y, Kamon H et al. Increased insulin sensitivity despite lipodystrophy in Crebbp heterozygous mice. *Nat. Genet.* 30, 221-226 (2002).
12. Roth J F, Shikama N, Henzen C et al. Differential role of p300 and CBP acetyltransferase during myogenesis: p300 acts upstream of MyoD and Myf5. *EMBO J.* 22, 5186-5196 (2003).
13. Foley P, Bunyan D, Stratton J, Dillon M, Lynch S A. Further case of Rubinstein Taybi syndrome due to a deletion in EP300. *Am. J. Med. Genet A.* 149A, 997-1000 (2009).
14. Tanaka Y, Naruse I, Maekawa T et al. Abnormal skeletal patterning in embryos lacking a single Cbp allele: a partial similarity with Rubinstein-Taybi syndrome. *Proc. Natl. Acad. Sci. U.S.A* 94, 10215-10220 (1997).
15. Yao T P, Oh S P, Fuchs M et al. Gene dosage-dependent embryonic development and proliferation defects in mice lacking the transcriptional integrator p300. *Cell.* 93, 361-372 (1998).
16. Teo J L, Ma H, Nguyen C, Lam C, Kahn M. Specific inhibition of CBP/beta-catenin interaction rescues defects in neuronal dif J. L. Teo, H. Ma, C. Nguyen, C. Lam, M. Kahn. Specific inhibition of CBP/beta-catenin interaction rescues defects in neuronal differentiation caused by a presenilin-1 mutation. *Proc. Natl. Acad. Sci. U.S.A.* 102, 12171-12176 (2005). This reference contains the first description of the differential coactivator usage model 17. Ma H, Nguyen C, Lee K S, Kahn M. Differential roles for the coactivators CBP and p300 on TCF/beta-catenin-mediated survivin gene expression. *Oncogene*. 24, 3619-3631 (2005).

18. Kawasaki H, Eckner R, Yao T P et al. Distinct roles of the co-activators p300 and CBP in retinoic-acid-induced F9-cell differentiation. *Nature*. 393, 284-289 (1998). First description of the differential effects in CBP or p300 knockdown on differentiation.

19. Roth J F, Shikama N, Henzen C et al. Differential role of p300 and CBP acetyltransferase during myogenesis: p300 acts upstream of MyoD and Myf5. *EMBO J.* 22, 5186-5196 (2003).

20. Rebel V I, Kung A L, Tanner E A, Yang H, Bronson R T, Livingston D M. Distinct roles for CREB-binding protein and p300 in hematopoietic stem cell self-renewal. *Proc. Natl. Acad. Sci. USA*. 99, 14789-14794 (2002).

21. Ugai H, Uchida K, Kawasaki H, Yokoyama K K. The coactivators p300 and CBP have different functions during the differentiation of F9 cells. *J. Mol. Med.* 77, 481-494 (1999).

22. McMillan M, Kahn M. Wnt Signaling, a Chemogenomic Safari. *Drug Discovery Today*, 10, 1467-1474 (2005).

23. Emami K H, Nguyen C, Ma H et al. A small molecule inhibitor of beta-catenin/CREB-binding protein transcription [corrected], *Proc. Natl. Acad. Sci. U.S.A.* 101, 12682-12687 (2004). Discovery and characterization of the small molecule CBP/catenin antagonist ICG-001.

24. Miyabayashi T, Teo J L, Yamamoto M, McMillan M, Nguyen C, Kahn M. Wnt/beta-catenin/CBP signaling maintains long-term murine embryonic stem cell pluripotency. *Proc. Natl. Acad. Sci. U.S.A.* 104, 5668-5673 (2007). Discovery and characterization of the small molecule p300/catenin antagonist IQ-1.

25. Bedford D C, Lawryn K H, Tomofusa F, Brindle P K. Target gene context influences the transcriptional requirement for the KAT3 family of CBP and p300 histone acetyltransferases. *Epigenetics*. 5, 9-15 (2010).

26. Sato N, Meijer L, Skaltsounis L, Greengard P, Brivanlou A H. Maintenance of pluripotency in human and mouse embryonic stem cells through activation of Wnt signaling by a pharmacological GSK-3-specific inhibitor. *Nat. Med.* 10, 55-63 (2004).

27. Kelly K F, Ng D Y, Jayakumaran G, Wood G A, Koide H, Doble B W. β-catenin enhances Oct-4 activity and reinforces pluripotency through a TCF-independent mechanism. *Cell Stem Cell.* 8, 214-227 (2011).

28. Otero J J, Fu W, Kan L, Cuadra A E, Kessler J A. Beta-catenin signaling is required for neural differentiation of embryonic stem cells. *Development* 131, 3545-3557 (2004).

29. Zechner D, Fujita Y, Hulsken J et al. Beta-Catenin signals regulate cell growth and the balance between progenitor cell expansion and differentiation in the nervous system. *Dev. Biol.* 258, 406-418 (2003).

30. Kim W Y, Wang X, Wu Y. et al. GSK-3 is a master regulator of neural progenitor homeostasis. *Nat Neurosci.* 12, 1390-1397 (2009).

31. McKinnon T, Ma H, Hasegawa K, Kahn M. Trophectoderm differentiation in mouse preimplantation embryos involves Wnt signaling and a switch to the transcriptional coactivator p300. Presented at: The ISSCR 7th Annual Meeting. Barcelona, Spain, 8-11 Jul. 2009.

32. Hasegawa K, Teo J L, Suemori H, Nakatsuji N, Pera M, Kahn M. Development of a novel xeno-free human embryonic stem cell culture system using small molecules. Presented at: The ISSCR 7th Annual Meeting. Barcelona, Spain, 8-11 Jul. 2009.

33. Marson A, Foreman R, Chevalier B et al. Wnt signaling promotes reprogramming of somatic cells to pluripotency. *Cell Stem Cell.* 3, 132-135 (2008).

34. Batlle E, Henderson J T, Beghtel H et al. Beta-catenin and TCF mediate cell positioning in the intestinal epithelium by controlling the expression of EphB/ephrinB. *Cell.* 111, 251-263 (2002).

35. Kumar S R, Scehnet J S, Ley E J et al. Preferential induction of EphB4 over EphB2 and its implication in colorectal cancer progression. Cancer Res. 69, 3736-3745 (2009). Erratum in: *Cancer Res.* 69, 4554 (2009).

36. Creyghton M P, Roël G, Eichhorn P J, et al. PR72, a novel regulator of Wnt signaling required for Naked cuticle function. *Genes Dev.* 19,376-386 (2005).

37. Zeng W, Wharton K A, Jr., Mack J A, et al. Naked cuticle encodes an inducible antagonist of Wnt signalling. *Nature* 403, 789-795 (2000).

38. Hirota M, Watanabe K, Hamada S et al. Smad2 functions as a co-activator of canonical Wnt/beta-catenin signaling pathway independent of Smad4 through histone acetyltransferase activity of p300. *Cell Signal.* 20, 1632-1641 (2008).

39. Kwon I K, Wang R, Thangaraju M et al. PKG inhibits TCF signaling in colon cancer cells by blocking beta-catenin expression and activating FOXO4. *Oncogene.* 29, 3423-3434 (2010).

40. Beildeck M E, Islam M, Shah S, Welsh J, Byers S W. Control of TCF-4 expression by VDR and vitamin D in the mouse mammary gland and colorectal cancer cell lines. *PLoS One.* 4, e7872 (2009).

41. Lindvall C, Bu W, Williams B O, Li Y. Wnt signaling, stem cells, and the cellular origin of breast cancer. *Stem Cell Rev* 3, 157-168 (2007).

42. Nagahata T, Shimada T, Harada A, et al. Amplification, up-regulation and over expression of DVL-1, the human counterpart of the *Drosophila* disheveled gene, in primary breast cancers. *Cancer Sci* 94, 515-518 (2003).

43. Ugolini F, Adélaïde J, Charafe-Jauffret E et al. Differential expression assay of chromosome arm 8p genes identifies Frizzled-related (FRP1/FRZB) and Fibroblast Growth Factor Receptor 1 (FGFR1) as candidate breast cancer genes. *Oncogene* 18, 1903-1910 (1999).

44. Roh M S, Hong S H, Jeong J S et al. Gene expression profiling of breast cancers with emphasis of β-catenin regulation. *J Korean Med Sci* 19, 275-282 (2004).

45. Mai M, Qian C, Yokomizo A, Smith D I, Liu W. Cloning of the human homolog of conductin (AXIN2), a gene mapping to chromosome 17q23-24. *Genomics* 55, 341-344 (1999).

46. Jeannet G, Scheller M, Scarpellino L et al. Long-term, multilineage hematopoiesis occurs in the combined absence of beta-catenin and gamma-catenin. *Blood.* 111, 142-149 (2008).

47. Szeto W, Jiang W, Tice D A et al. Overexpression of the retinoic acid-responsive gene Stra6 in human cancers and its synergistic induction by Wnt-1 and retinoic acid. *Cancer Res.* 61, 4197-4205 (2001).

48. LaBarge M A. The difficulty of targeting cancer stem cell niches. *Clin Cancer Res* 16, 3121-3129 (2010).

49. Merchant A, Watsui W. Targeting Hedgehog—a cancer stem cell pathway. *Clin Cancer Res.* 16, 3130-3140 (2010).

50. Pannuti A, Foreman K, Rizzo P, et al. Targeting Notch to target cancer stem cells. *Clin Cancer Res* 16, 3142-3152 (2010).

51. Al-Hajj M, Becker M W, Wicha M, Weissman I, Clarke M F. Therapeutic implications of cancer stem cells. *Curr Opin Genet Dev.* 14(1):43-47 (2004).
52. Mani S A, Guo W, Liao M J et al. The epithelial-mesenchymal transition generates cells with properties of stem cells. *Cell.* 133, 704-715 (2008).
53. Radich J P, Dai H, Mao M et al., Gene expression changes associated with progression and response in chronic myeloid leukemia. *Proc Natl Acad Sci USA.* 103, 2794-2799 (2006).
54. Henderson W R Jr, Chi E Y, Ye X et al. Inhibition of Wnt/beta-catenin/CREB binding protein (CBP) signaling reverses pulmonary fibrosis. *Proc Natl Acad Sci USA.* 107, 14309-14314 (2010).
55. Cissé M, Halabisky B, Harris J et al. Reversing EphB2 depletion rescues cognitive functions in Alzheimer model. *Nature.* 469, 47-52 (2011).
56. Bultje R S, Castaneda-Castellanos D R, Jan L Y, Jan Y N, Kriegstein A R, Shi S H. Mammalian Par3 regulates progenitor cell asymmetric division via notch signaling in the developing neocortex. *Neuron.* 63, 189-202 (2009).
57. Schenke-Layland K, Nsair A, Van Handel B et al. Recapitulation of the embryonic cardiovascular progenitor cell niche. *Biomaterials.* 2, 2748-2756 (2011).
58. Yilmaz O H, Valdez R, Theisen B K et al. Pten dependence distinguishes haematopoietic stem cells from leukaemia-initiating cells. *Nature.* 441, 475-482 (2006).
59. Cairns J. Mutation, selection and Cancer Nature 255, 197-200 (1975). Cairns J. Cancer and the immortal strand hypothesis. *Genetics.* 174, 1069-1072 (2006).
60. Hernandez L, Roux K J, Wong E S et al. Functional coupling between the extracellular matrix and nuclear lamina by Wnt signaling in progeria. *Dev Cell.* 19, 413-425 (2010).
61. Liu H, Fergusson M M, Castilho R M et al. Augmented Wnt signaling in a mammalian model of accelerated aging. *Science.* 317, 803-806 (2007).
62. Brack A S, Conboy M J, Roy S et al. Increased Wnt signaling during aging alters muscle stem cell fate and increases fibrosis. *Science.* 317, 807-810 (2007).

II. Treating Hair Loss; e.g., Promoting Hair Growth and/or Regrowth and/or Preventing or Retarding Hair Loss (and Loss of Hair Pigmentation)

Particular aspects of the present invention provide compositions comprising CBP/catenin (e.g., CBP/β-catenin) antagonists for use in promoting hair growth and/or regrowth and/or preventing or retarding hair loss (e.g., in aging subjects) and loss of hair pigmentation).

According to particular aspects, treating hair loss; e.g., promoting hair growth and/or regrowth and/or preventing or retarding hair loss (and loss of hair pigmentation), comprises administering (e.g., topically or otherwise) to a subject in need thereof an amount of a CBP/catenin (e.g., CBP/β-catenin) antagonist sufficient for increasing the number of symmetric renewing divisions at the expense of symmetric divisions in the relevant stem cell population (e.g., follicle stem cells), wherein a method for treating hair loss (e.g., preventing hair loss and/or promoting hair growth; e.g., in aging subjects) (and loss of hair pigmentation) is afforded.

Skin is the largest organ in the body. It protects animals from pathogens and damages from external environment. It contains nerve endings that react to heat and cold, touch and pressure, and a variety of environmental changes. It regulates body temperature, it helps to control body fluid; it is an important storage center for lipid and water; it also critical for the synthesis of molecules such as vitamin D. Beyond all the above mentioned physiological functions, skin and hair are important in self image and self-esteem.

Hair cycle. The hair cycle, as briefly reviewed in Thompson & Sisk (*Cell Cycle* 5:17, 1913-1917, 2006; incorporated by reference in its entirety), is divided into periods of follicle growth (anagen), followed by regression (catagen) and rest (telogen). During the regression phase, the lower half of the follicle is completely destroyed by apoptosis. Following the rest phase, hair follicle growth is reinitiated as follicle stem cells are induced to proliferate, and their progeny migrate and differentiate into the cell types that comprise the hair bulb. The most widely accepted model for hair follicle regeneration, the bulge activation hypothesis, specifies that regression of the lower part of the follicle brings the mesenchymal cells of the dermal papilla (DP) into proximity with the stem cell niche (bulge), allowing a diffusible signal from the DP to reach the quiescent stem cells. A number of signaling pathways have been implicated in follicle regeneration, including Sonic hedgehog, Wnts and TGF-β family members.

Wnt signaling. Wnt signaling, as widely appreciated in the art, has been implicated in hair follicle cycling (likely through a stem cell mediated process). The Hairless (Hr, formerly hr) gene mutation is particularly useful for analyzing the hair cycle, and in these mice, while initial hair growth is normal, once the hair is shed and follicles regress, the follicles fail to regenerate and hair loss becomes permanent. Thompson & Sisk (Id) summarize that the Hairless protein (HR) (nuclear receptor corepressor) regulates gene expression that controls Wnt signaling during the hair cycle, and in particular HR represses expression of Wise, an inhibitor of Wnt signaling, and likely plays a role in controlling the timing of Wnt signaling required for hair cycling—thus supporting a model in which HR regulates fair follicle regeneration by promoting Wnt signaling. Consistent with this model, Beaudoin et al (*PNAS* 102:14653-14658, 2005; incorporated by reference in its entirety) show that transgenic expression of HR in progenitor keratinocytes rescues follicle regeneration in Hr$^{-/-}$ mice, and that expression of Wise is repressed by HR in these cells, coincident with the timing of follicle regeneration—thereby linking HR and Wnt function in a model wherein HR regulates the precise timing of Wnt signaling required for hair follicle regeneration. Additionally, Lyubimova et al (*The Journal of Clinical Investigation* 120:446-456, 2010; incorporated by reference in its entirety) have shown that N-WASP deficiency in mouse skin leads to severe alopecia, and further showed a link between N-WASP and Wnt signaling, proposing that N-WASP acts as a positive regulator of β-catenin-dependent transcription, modulating differentiation of hair follicle progenitor cells.

Precise mechanism unknown. The precise mechanisms, however, by which hair growth is reinitiated are not fully understood, and are likely to involve the integration of multiple signaling pathways. For example, Botchkareva et al. (*Journal of Investigative Dermatology* doi:10.1038/sj.jid.5700537, 2006; incorporated by reference in its entirety) provide evidence that survivin is expressed in the proliferating keratinocytes of the hair matrix and outer root sheath of human anagen hair follicles and its expression is decreased with the progression of catagen phase, that expression of survivin in anagen hair follicles may be controlled by Wnt/13-catenin signaling, and that the dual functions of survivin (promoting proliferation and preventing apoptosis) may be involved in the control of the delicate proliferation-apoptosis balance controlling HF cyclic behavior. Botchkareva et al., showed, in an in vitro microdissected hair follicle model, that the β-catenin antagonist ICG-001 decreased survivin expression and also significantly reduced hair fiber elongation in a dose-dependent matter.

As appreciated in the art therefore, Wnt/β-catenin signaling appears to be required for hair growth and hair follicle recycling, and inhibition of Wnt/β-catenin signaling has been shown to inhibit hair growth and hair follicle recycling.

Particular aspects of the present invention, surprisingly, provide a method for stimulating hair growth and/or regrowth and/or preventing hair loss, comprising administering to a subject in need thereof an amount of a CBP/catenin (e.g., CBP/β-catenin) antagonist sufficient for stimulating hair growth and/or regrowth and/or preventing hair loss. In certain embodiments, the CBP/β-catenin antagonist is present in an amount sufficient to modulate or increase the expression of an adenosine receptor in dermal cells (e.g., dermal papilla cells). In certain aspects, the adenosine receptor is at least one selected from A1, A2A, and A2B (e.g., A1 and/or A2).

In particular embodiments of the methods, the CBP/catenin (e.g., CBP/β-catenin) antagonist is present in an amount sufficient to modulate or increase the expression of sulfonylurea receptor 2B in dermal papilla cells.

In particular embodiments of the methods, the CBP/catenin (e.g., CBP/β-catenin) antagonist is at least one selected from the group of compounds encompassed by Table 1 or otherwise disclosed herein. In certain aspects, the CBP/catenin (e.g., CBP/β-catenin) antagonist is at least one selected from the group of compounds encompassed by Table 1 or otherwise disclosed herein. In particular embodiments, the CBP/catenin (e.g., CBP/β-catenin) antagonist comprises an active alkyl and/or fatty acid ester derivative thereof. In particular embodiments, the CBP/catenin (e.g., CBP/β-catenin) antagonist comprises ICG-001 or an active alkyl and/or fatty acid ester derivative thereof.

In certain aspects of the methods, administration of the CBP/catenin (e.g., CBP/β-catenin) antagonist comprises topical administration.

Particular aspects of the methods comprise co-administration of or adjunct treatment with at least one other hair growth stimulating agent, or hair loss preventing agent. In certain embodiments, the at least one other hair growth stimulating agent is selected from the group consisting of minoxidil, finasteride, dutasteride, bimatoprost and antiandrogen receptor blockers including fluridil.

Particular embodiments of the methods comprise co-administering of or adjunctive treating with at least one anti-inflammatory agent. In certain embodiments, the at least one anti-inflammatory agent is selected from the group consisting of: short-acting $β_2$-agonists, long-acting $β_2$-agonists, anticholinergics, corticosteroids, systemic corticosteroids, mast cell stabilizers, leukotriene modifiers, methylxanthines, $β_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, glucocorticoid steroids, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof.

Additional aspects provide a method for increasing the expression of an adenosine receptor in dermal cells (e.g., dermal papilla cells), comprising administering to a subject in need thereof an amount of a CBP/catenin (e.g., CBP/β-catenin) antagonist sufficient for increasing the expression of an adenosine receptor in dermal cells (e.g., dermal papilla cells). In certain aspects, the adenosine receptor is at least one selected from A1, A2A, and A2B. In particular embodiments, the CBP/β-catenin antagonist is present in an amount sufficient to modulate or increase the expression of sulfonylurea receptor 2B in dermal papilla cells.

According to particular aspects, CBP/catenin (e.g., CBP/β-catenin) antagonists, essentially Wnt/catenin modulators/orchestrators by increasing p300/catenin transcription thereby promoting skin/hair-follicle stem cell differentiation (e.g., stimulating asymmetric versus symmetric stem cell divisions), display a broad range of beneficial effects, such as accelerating skin healing, delaying skin aging, and surprisingly promoting hair growth and/or regrowth and/or preventing hair loss or loss of pigmentation.

According to particular aspects, the CBP/catenin (e.g., CBP/β-catenin) antagonists function (e.g., to increase repair skin and/or stimulate hair growth) by regulating human endogenous stem cells and/or surrounding cell function, and are extremely safe at effective dose levels—an important consideration, since many skin/hair conditions may require long-term administration.

The presently disclosed stimulation of hair growth and/or regrowth is, in fact, surprising because of the art-recognized requirement for Wnt signaling (β-catenin mediated signaling) for hair follicle cycling and hair growth as summarized herein above, which indicates that CBP/β-catenin antagonists, which have been implicated in "modulating" hair growth, would in fact modulate hair growth by inhibiting hair growth by inhibiting hair follicle cycling and hair growth. The presently claimed method of stimulating hair growth and/or regrowth (and/or preventing pigmentation loss) is, therefore, unexpected, given the widespread, art-recognized dogma to the contrary.

Applicant unexpectedly discovered the presently claimed activity in the course of treating a leukaemia mouse model with a CBP/catenin (e.g., CBP/β-catenin) antagonist (ICG-001) (see working Example 1 below), wherein it was observed that within two weeks of shaving the mice (for insertion of minipumps), the animals receiving ICG-001 had regrown their hair, whereas the controls (because of irradiation and chemotherapy) had not. This led the present applicant to consider additional possible actions of CBP/β-catenin antagonists relevant for hair growth.

In particular, as disclosed herein in working Example 4, applicant conducted gene expression array experiments that demonstrated that treatment of cells in culture with a CBP/catenin antagonist (e.g., ICG-001) dramatically (~10×) increased the expression of adenosine receptors (e.g., colonic epithelium Adenosine receptor A2B (ADORA2B)).

Additionally, applicant was aware (see Li et al., *Journal of Investigative Dermatology* 117:1594-1600, 2001; incorporated herein by reference in its entirety), that significant inhibition in increase in intracellular calcium level by minoxidil or adenosine was observed as the result of pre-treatment with 8-cyclopentyl-1,3-dipropylxanthine, an antagonist for adenosine A1 receptor, but not by 3,7-dimethyl-1-propargyl-xanthine, an antagonist for adenosine A2 receptor. Additionally, however, Li et al. show (Id) that in dermal papilla cells (DPC), both Adenosine-mediated increase in intracellular Ca (mostly A1 related), and Adenosine-mediated VEGF production (both A1 and A2 related) are important for minoxidil-induced hair growth. Therefore, DPCs have multiple adenosine-dependent pathways, and in this respect, applicant reasoned that upregulated A2 would reasonably be expected to help hair growth. Applicants, therefore, without being bound by mechanism, conceived that CBP/catenin (e.g., CBP/β-catenin) antagonist may stimulate hair growth by modulating Adenosine receptor expression in, for example, DPC. Furthermore, applicant reasoned that VEGF is a Wnt regulated target as well and is also known by applicant to be increased by CBP/catenin (e.g., CBP/β-catenin) antagonists.

According to particular aspects, CBP/β-catenin antagonists having utility for hair growth and/or regrowth and/or prevention of alleviation of hair loss are those CBP/catenin antagonists described and disclosed in the patents and patent applications of TABLE 1 herein below.

Hair Growth Stimulation; Combination Therapies

As discussed above, Minoxidil, the active ingredient in Rogaine, activity is mediated via the adenosine receptor in dermal papilla cells. Several adenosine receptors are expressed in dermal papilla cells (A1, A2A and A2B (Li M., et al., *J. Invest. Dermatol.* 117, 1594-1600, 2001).

In gene expression array experiments, Applicants demonstrated herein that treatment of cells in culture with a CBP/catenin (e.g., CBP/β-catenin) antagonist (e.g., ICG-001) dramatically (~10×) increases the expression of adenosine receptors, e.g., in colonic epithelium Adenosine Receptor A2B (ADORA2B).

According to particular embodiments, therefore, administration of a CBP/catenin (e.g., CBP/β-catenin) antagonist with another hair stimulating agent (e.g., Minoxidil) provides a strong additive or synergistic effect in hair growth and/or regrowth when treating the scalp, e.g., topically with a CBP/catenin (e.g., CBP/β-catenin) antagonist to, for example, increase the expression of adenosine receptors and/or modulating the sulfonylurea receptor 2B believed to be the molecular target through which minoxidil works.

Methods of Treatment

In general, for purposes of this application, the term "treating" refers to, and includes, reversing, alleviating, inhibiting the progress of, or preventing a disease, disorder or condition, or one or more symptoms thereof; and "treatment" and "therapeutically" refer to the act of treating, as defined herein.

A "therapeutically effective amount" is any amount of any of the compounds utilized in the course of practicing the invention provided herein that is sufficient to reverse, alleviate, inhibit the progress of, or prevent a disease, disorder or condition, or one or more symptoms thereof.

Cosmetic and/or Therapeutic Application and Administration

In particular exemplary embodiments, the CBP/catenin (e.g., CBP/β-catenin) antagonists of the present invention may function as a cosmetic and/or therapeutic composition alone or in combination with another cosmetic and/or therapeutic agent such that the therapeutic composition stimulates hair growth and/or regrowth and/or prevents hair loss. The compositions of the present invention include compositions that are able to be administered to a subject in need thereof. As used herein, "subject," may refer to any living creature, preferably an animal, more preferably a mammal, and even more preferably a human.

In certain embodiments, the composition formulation may also comprise at least one additional agent selected from the group consisting of: carriers, adjuvants, emulsifying agents, suspending agents, sweeteners, flavorings, perfumes, and binding agents.

Generally, as used herein, "pharmaceutically acceptable carrier" and "carrier" generally refer to a non-toxic, inert solid, semi-solid or liquid filler, diluent, encapsulating material or formulation auxiliary of any type (e.g., including creams and lotions, emulsions, jellies, depot formulations). Some non-limiting examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable carriers described herein, for example, vehicles, adjuvants, excipients, or diluents, are well-known to those who are skilled in the art. Typically, the pharmaceutically acceptable carrier is chemically inert to the therapeutic agents and has no detrimental side effects or toxicity under the conditions of use. The pharmaceutically acceptable carriers can include polymers and polymer matrices, nanoparticles, microbubbles, and the like.

In addition to the therapeutic CBP/catenin (e.g., CBP/β-catenin) antagonists of the present invention, the therapeutic composition may further comprise inert diluents such as additional solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Administrative Routes

Most suitable means of administration for a particular subject will depend on the nature and severity of the disease or condition being treated or the nature of the therapy being used, as well as the nature of the therapeutic composition or additional therapeutic agent. In certain embodiments, oral or topical administration is preferred.

Preferably, topical administration is used. In certain aspects, subcutaneous administration, systemic, IV, or p.o., etc., is used.

Formulations suitable for oral administration may be provided as discrete units, such as tablets, capsules, cachets, syrups, elixirs, chewing gum, "lollipop" formulations, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

As shown in the Examples herein, CBP/catenin (e.g., CBP/β-catenin) antagonists have been tested in mouse models and demonstrated accelerated skin healing after injury and promotion of hair growth.

III. Treating Skin Related Diseases or Conditions, Including for Cosmetic Purposes Particular aspects of the present invention provide compositions comprising CBP/beta-catenin antagonists for use in treating skin related diseases or conditions, including for cosmetic purposes (e.g., in aging subjects). Skin related diseases include any disorders that occur in skin structure, including but not limited to wounds, acne, sun damage, certain skin diseases, for which there is currently no cure (for example latent viral infection of epidermal or mucosal tissues (e.g., HSV, HPV)), ulcers (for example, diabetic), burns, atopic dermatitis, psoriasis, and the effects of aging (e.g., wrinkles, hyperpigmentation, dryness, redness, cracking, rosacea, firmness, elasticity, thickness, appearance). The cosmetic usage includes improvement and preventive function occur in both skin and hair structure. Adjunctive and combination therapy embodiments are encompassed.

According to particular aspects, treating skin related diseases or conditions comprises administering (e.g., topically or otherwise) to a subject in need thereof an amount of a CBP/catenin (e.g., CBP/$\beta$-catenin) antagonist sufficient for increasing the number of symmetric renewing divisions at the expense of symmetric divisions in the relevant stem cell population (e.g., skin stem cells), wherein a method for treating skin related diseases or conditions is afforded.

Skin is the largest organ in the body. It protects animals from pathogens and damages from external environment. It contains nerve endings that react to heat and cold, touch and pressure, and a variety of environmental changes. It regulates body temperature, it helps to control body fluid; it is an important storage center for lipid and water; it also critical for the synthesis of molecules such as vitamin D. Beyond all the above mentioned physiological functions, skin and hair are important in self image and self-esteem.

Skin care (including, wound, ulcer and burn care, and treatment of acne, atopic dermatitis, psoriasis, alopecia, and the effects of aging) is desirable in order to improve health and appearance of the outer epidermis, as well as underlying dermal and other tissues. Wounds, ulcers, and burns, either injury induced (such as cuts, abrasions (either from injury or treatments such as laser mediated dermabrasion), blisters, etc.), or surgically induced (such as surgical incisions, astomies, etc.) require localized treatment to remedy the affected area and prevent further dermal damage.

Currently, most of the medications for wounds, ulcers, burns, and skin diseases focus on relief of the symptoms; few of them target the cause of the problem and therefore do not speed the healing process that requires initially asymmetric division of the skin stem cells. Similar situations exist for both skin improvement and hair growth. Novel therapeutic methods and compositions for skin care and healing wounds, ulcers, burns, and skin diseases are, therefore, needed.

As disclosed herein, CBP/catenin (e.g., CBP/$\beta$-catenin) antagonists can be used to promote skin stem cell differentiation, and display a broad range of beneficial effects, such as accelerating skin healing and delaying skin aging.

CBP/catenin (e.g., CBP/$\beta$-catenin) antagonists function by regulating human endogenous stem cells and/or surrounding cell function. Based on animal toxicity studies, and as recognized in the art, these compounds are extremely safe at effective dose levels. Since many skin/hair conditions may require long-term administration, a large safety margin will be very favorable to physicians and patients alike. According to particular aspects, CBP/catenin (e.g., CBP/$\beta$-catenin) antagonists provide for treatment of certain skin diseases, for which there is currently no cure, including but not limited to latent viral infection (e.g., HSV, HPV), ulcers (diabetic others), burns, atopic dermatitis, psoriasis, actinic keratosis, alopecia, etc.

Particular aspects provide a method for treating a condition or disease of the skin or at least one symptom thereof, comprising administering to a subject in need thereof an amount of a CBP/catenin (e.g., CBP/$\beta$-catenin) antagonist sufficient for treating a condition or disease of the skin or at least one symptom thereof. In certain aspects, the condition or disease of the skin, comprises treating at least one condition or disease selected from the group consisting of wounds, scarring, acne, sun damage, treatment of latent viral infection (e.g., to HSV, HPV), ulcers including diabetic ulcers, burns, atopic dermatitis, psoriasis, and effects of aging including wrinkles, hyperpigmentation, redness, rosacea, dryness, cracking, loss of firmness, loss of elasticity, thinning, and loss of vibrance.

In particular embodiments of the methods, the CBP/catenin (e.g., CBP/$\beta$-catenin) antagonist is at least one selected from the group of compounds and salts thereof encompassed by Table 1 or otherwise disclosed herein. In certain aspects, the CBP/$\beta$-catenin antagonist comprises an alkyl and/or fatty acid ester derivative thereof as disclosed herein. In certain embodiments, the CBP/$\beta$-catenin antagonist comprises ICG-001 or an active alkyl and/or fatty acid ester derivative thereof as disclosed herein.

Preferably, administration of the CBP/catenin (e.g., CBP/$\beta$-catenin) antagonist comprises topical administration.

Certain aspects of methods comprise co-administration of or adjunct treatment with at least one other therapeutic agent (e.g., such as simultaneously or adjunctively treating the subject with an anti-inflammatory agent). In certain aspects, the anti-inflammatory agent comprises a steroid or glucocorticoid steroid. In particular embodiments, the at least one anti-inflammatory agent is selected from the group consisting of: short-acting $\beta_2$-agonists, long-acting $\beta_2$-agonists, anticholinergics, corticosteroids, systemic corticosteroids, mast cell stabilizers, leukotriene modifiers, methylxanthines, $\beta_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, glucocorticoid steroids, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof.

Antiviral (HSV) combinations may include a nucleoside analog (e.g., acyclovir or HSV docosanol (active ingredient in Abreva)).

In certain aspects, the one additional therapeutic agent is selected from the group consisting of anti-microbial agents, antifungal agents, and antibiotic agents. In particular embodiments, the at least one additional therapeutic agent is selected from the group consisting of: ciclosporin, hyaluronic acid, carmellose, macrogol(s), dextran and hyprolose, sodium and calcium, sodium and povidone, hypromellose, carbomer, amikacin, gentamicin, kanamycin, neomycin, netilmicin, streptomycin, tobramycin, paromomycin, geldanamycin, herimycin, loracarbef, ertapenem, imipenem/cilastatin, meropenem, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, peperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, tinidazole, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, teronazole, terbinafine, amorolfine, naftifine, butenafine, anidulafungin, caspofungin, micafungin, ciclopirox, flucytosine, griseofulvin, Gentian violet, haloprogin, tolnaftate, undecylenic acid, and combinations thereof.

Yet additional aspects, provide a method for cosmetically treating a condition of the skin or at least one symptom thereof, comprising administering to a subject in need thereof an amount of a CBP/catenin (e.g., CBP/β-catenin) antagonist sufficient for cosmetically treating a condition of the skin or at least one symptom thereof. In certain aspects, the condition of the skin, comprises treating at least one condition or disease selected from the group consisting of wrinkles, hyperpigmentation, redness, rosacea, dryness, cracking, loss of firmness, loss of elasticity, thinning, and loss of vibrance. In particular aspects, the CBP/catenin (e.g., CBP/β-catenin) antagonist is at least one selected from the group of compounds and salts thereof encompassed by Table 1 or otherwise disclosed herein. In certain embodiments, the CBP/catenin (e.g., CBP/β-catenin) antagonist comprises an alkyl and/or fatty acid ester derivative thereof as disclosed herein. In particular aspects, the CBP/catenin (e.g., CBP/β-catenin) antagonist comprises ICG-001 or an active alkyl and/or fatty acid ester derivative thereof as disclosed herein. Preferably, administration of the CBP/catenin (e.g., CBP/β-catenin) antagonist comprises topical administration.

Particular aspects provide compositions and methods to enhance skin care (including, wound, ulcer and burn care, and treatment of acne, atopic dermatitis, actinic keratosism, psoriasis, and the effects of aging), to treat dermatological disorders and for cosmetic applications, which is desirable in order to improve health and appearance of the outer epidermis, as well as underlying dermal and other tissues. Skin related diseases include any disorders that occur in skin structure, including but not limited to wounds, acne, sun damage, certain skin diseases, for which there is currently no cure (for example viral infection (HSV, HPV)), ulcers (for example, diabetic), burns, atopic dermatitis, psoriasis, and the effects of aging (e.g., wrinkles, hyperpigmentation, dryness, redness, cracking, rosacea, firmness, elasticity, thickness, appearance).

As recognized in the art, Wnt signaling is required during wound healing. For example, Fathke et al (*BMC Cell Biology* 7:4 doi 10.1186/1471-2121-7-4) show that Wnt signaling induces epithelial differentiation during cutaneous wound healing. Likewise, for example, Gudjonsson et al (The Journal of Investigative Dermatology 130:1849-1859, 2010) show that canonical Wnt signaling is reduced in lesional psoriatic skin.

According to particular aspects, CBP/catenin (e.g., CBP/β-catenin) antagonists promote skin/hair-follicle stem cell differentiation, thereby providing for a broad range of beneficial effects, such as accelerating skin healing, delaying skin aging.

According to particular aspects, the CBP/catenin (e.g., CBP/β-catenin) antagonists function (e.g., to enhance repair of skin) by regulating human endogenous stem cells and/or surrounding cell function, and are extremely safe at effective dose levels—an important consideration, since many skin/hair conditions may require long-term administration.

Applicants unexpectedly discovered the presently claimed activity in the course of treating a leukaemia mouse model with a CBP/catenin (e.g., CBP/β-catenin) antagonist (ICG-001) (see working Example 1 below), wherein it was observed that within two weeks of shaving the mice and inserting the minipumps, the wounds of the animals receiving ICG-001 had substantial improved, whereas the controls had not. This led the present Applicants to consider additional possible actions of CBP/catenin (e.g., CBP/β-catenin) antagonists relevant for wound care.

According to particular aspects, CBP/catenin (e.g., CBP/β-catenin) antagonists having utility for treatment of dermatological disorders and cosmetic applications as disclosed herein are those CBP/catenin antagonists described and disclosed in the patents and patent applications of TABLE 1 below.

Particular aspects provide formulations for topical application of CBP/catenin (e.g., CBP/β-catenin) antagonists, such as those of TABLE 1.

Methods of Treatment

The term "treating" refers to, and includes, reversing, alleviating, inhibiting the progress of, or preventing a disease, disorder or condition, or one or more symptoms thereof; and "treatment" and "therapeutically" refer to the act of treating, as defined herein.

A "therapeutically effective amount" is any amount of any of the compounds utilized in the course of practicing the invention provided herein that is sufficient to reverse, alleviate, inhibit the progress of, or prevent a disease, disorder or condition, or one or more symptoms thereof.

Cosmetic and/or Therapeutic Application and Administration

In particular exemplary embodiments, the CBP/β-catenin antagonists of the present invention may function as a cosmetic and/or therapeutic composition alone or in combination with another cosmetic and/or therapeutic agent such that the therapeutic composition prevents or alleviates at least one symptom of a wound-related disease or condition, or to increase proper wound healing. The therapeutic compositions of the present invention include compositions that are able to be administered to a subject in need thereof. As used herein, "subject," may refer to any living creature, preferably an animal, more preferably a mammal, and even more preferably a human.

In certain embodiments, the composition formulation may also comprise at least one additional agent selected from the group consisting of: carriers, adjuvants, emulsifying agents, suspending agents, sweeteners, flavorings, perfumes, and binding agents.

As used herein, "pharmaceutically acceptable carrier" and "carrier" generally refer to a non-toxic, inert solid, semi-solid or liquid filler, diluent, encapsulating material or formulation auxiliary of any type (e.g., including creams and lotions, emulsions, jellies, depot formulations). Some non-limiting examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable carriers described herein, for example, vehicles, adjuvants, excipients, or diluents, are well-known to those who are skilled in the art. Typically, the pharmaceutically acceptable carrier is chemically inert to the therapeutic agents and has no detrimental side effects or toxicity under the conditions of use. The pharmaceutically acceptable carriers can include polymers and polymer matrices, nanoparticles, microbubbles, and the like.

In addition to the therapeutic CBP/catenin (e.g., CBP/β-catenin) antagonists of the present invention, the therapeutic composition may further comprise inert diluents such as additional solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Administrative Routes

Most suitable means of administration for a particular subject will depend on the nature and severity of the disease or condition being treated or the nature of the therapy being used, as well as the nature of the therapeutic composition or additional therapeutic agent. In certain embodiments, oral or topical administration is preferred.

Preferably, topical administration is used.

Formulations suitable for oral administration may be provided as discrete units, such as tablets, capsules, cachets, syrups, elixirs, chewing gum, "lollipop" formulations, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

As shown in the Examples herein, CBP/catenin (e.g., CBP/β-catenin) antagonists have been tested in mouse models and demonstrated accelerated skin healing after injury and promotion of hair growth.

IV. Exemplary CBP/Catenin (e.g., CBP/β-catenin) Antagonists Having Utility in the Herein Disclosed Methods In particular embodiments of the herein described methods (treating of aging, age-related conditions or diseases, hair growth or preventing hair loss, and treating skin conditions), the CBP/catenin (e.g., CBP/β-catenin) antagonist is at least one selected from the group of compounds and salts thereof encompassed by Table 1 or otherwise disclosed herein. In certain aspects, the CBP/catenin (e.g., CBP/β-catenin) antagonist comprises an alkyl and/or fatty acid ester derivative thereof as disclosed herein. In certain embodiments, the CBP/catenin (e.g., CBP/β-catenin) antagonist comprises ICG-001 or an active alkyl and/or fatty acid ester derivative thereof as disclosed herein.

Preferably, administration of the CBP/catenin (e.g., CBP/β-catenin) antagonist comprises topical and/or oral and/or IV and/or intramuscular, etc., administration.

Certain aspects of methods comprise co-administration of or adjunct treatment with at least one other therapeutic agent (e.g., such as simultaneously or adjunctively treating the subject with an anti-inflammatory agent). In certain aspects, the anti-inflammatory agent comprises a steroid or glucocorticoid steroid. In particular embodiments, the at least one anti-inflammatory agent is selected from the group consisting of: short-acting $\beta_2$-agonists, long-acting $\beta_2$-agonists, anticholinergics, corticosteroids, systemic corticosteroids, mast cell stabilizers, leukotriene modifiers, methylxanthines, $\beta_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, glucocorticoid steroids, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof.

In certain aspects, the one additional therapeutic agent is selected from the group consisting of anti-microbial agents, antifungal agents, and antibiotic agents. In particular embodiments, the at least one additional therapeutic agent is selected from the group consisting of: ciclosporin, hyaluronic acid, carmellose, macrogol(s), dextran and hyprolose, sodium and calcium, sodium and povidone, hypromellose, carbomer, amikacin, gentamicin, kanamycin, neomycin, netilmicin, streptomycin, tobramycin, paromomycin, geldanamycin, herimycin, loracarbef, ertapenem, imipenem/cilastatin, meropenem, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, peperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, tinidazole, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, teronazole, terbinafine, amorolfine, naftifine, butenafine, anidulafungin, caspofungin, micafungin, ciclopirox, flucytosine, griseofulvin, Gentian violet, haloprogin, tolnaftate, undecylenic acid, and combinations thereof.

Yet additional aspects, provide a method for cosmetically treating a condition of the skin or at least one symptom thereof, comprising administering to a subject in need thereof an amount of a CBP/catenin (e.g., CBP/β-catenin) antagonist sufficient for cosmetically treating a condition of the skin or at least one symptom thereof. In certain aspects, the condition of the skin, comprises treating at least one condition or disease selected from the group consisting of wrinkles, hyperpigmentation, redness, rosacea, dryness, cracking, loss of firmness, loss of elasticity, thinning, and loss of vibrance. In particular aspects, CBP/catenin (e.g., CBP/β-catenin) antagonist is at least one selected from the group of compounds and salts thereof encompassed by Table 1 or otherwise disclosed herein. In certain embodiments, the CBP/catenin (e.g., CBP/β-catenin) antagonist comprises an alkyl and/or fatty acid ester derivative thereof as disclosed herein. In particular aspects, the CBP/catenin (e.g., CBP/β-catenin) antagonist comprises ICG-001 or an active alkyl and/or fatty acid ester derivative thereof as disclosed herein. Preferably, administration of the CBP/catenin (e.g., CBP/β-catenin) antagonist comprises topical administration.

Particular aspects provide compositions and methods for treating aging.

Particular aspects provide compositions and methods for treating the effects of aging (e.g., wrinkles, hyperpigmentation, dryness, redness, cracking, rosacea, firmness, elasticity, thickness, appearance).

As recognized in the art, Wnt signaling is required during wound healing. For example, Fathke et al (*BMC Cell Biology* 7:4 doi 10.1186/1471-2121-7-4) show that Wnt signaling induces epithelial differentiation during cutaneous wound healing. Likewise, for example, Gudjonsson et al (The Journal of Investigative Dermatology 130:1849-1859, 2010) show that canonical Wnt signaling is reduced in lesional psoriatic skin.

According to particular aspects, CBP/catenin (e.g., CBP/β-catenin) antagonists promote skin/hair-follicle stem cell differentiation, thereby providing for a broad range of beneficial effects, such as accelerating skin healing, delaying skin aging.

According to particular aspects, the CBP/catenin (e.g., CBP/β-catenin) antagonists function (e.g., to enhance repair of skin) by regulating human endogenous stem cells and/or surrounding cell function, and are extremely safe at effective dose levels—an important consideration, since many skin/hair conditions may require long-term administration.

Applicants unexpectedly discovered the presently claimed activity in the course of treating a leukaemia mouse model with a CBP/catenin (e.g., CBP/β-catenin) antagonist (ICG-001) (see working Example 1 below), wherein it was observed that within two weeks of shaving the mice and inserting the minipumps, the wounds of the animals receiving ICG-001 had substantial improved, whereas the controls had not. This led the present Applicants to consider additional possible actions of CBP/catenin (e.g., CBP/β-catenin) antagonists relevant for wound care.

According to particular aspects, CBP/catenin (e.g., CBP/β-catenin) antagonists having utility for treatment of dermatological disorders and cosmetic applications as disclosed herein are those CBP/catenin (e.g., CBP/β-catenin) antagonists described and disclosed in the patents and patent applications of TABLE 1 below.

Particular aspects provide formulations for topical application of CBP/catenin (e.g., CBP/β-catenin) antagonists, such as those of TABLE 1.

TABLE 1

Exemplary CBP/β-catenin antagonists having utility for the treatment of aging and related dermatological disorders and cosmetic applications, having utility for and hair growth and/or regrowth and/or prevention of alleviation of hair loss, stimulating adenosing receptor expression, and for the treatment of dermatological disorders and cosmetic applications as disclosed herein. All compound genera, species and conformations thereof, and syntheses thereof, of the patent applications and patents of this Table are incorporated by reference herein in their entireties, as exemplary compounds having utility for the presently claimed methods.

| Application/Pat. No. | Publication date | Compound class | Compound genus |
|---|---|---|---|
| US 2005/0250780 | 10 November 2005; MMX | Reverse turn mimetics; All genera and compounds and salts thereof disclosed and claimed therein | (structure with R1, R2, R3, R4) |
| US 2007/0021431 A1 | 25 January 2007; CWP | Reverse turn mimetics; All genera and compounds and salts thereof disclosed and claimed therein | (structure with R1, R2, W, G, E, D, B, A) |

TABLE 1-continued

Exemplary CBP/β-catenin antagonists having utility for the treatment of aging and related dermatological disorders and cosmetic applications, having utility for and hair growth and/or regrowth and/or prevention of alleviation of hair loss, stimulating adenosing receptor expression, and for the treatment of dermatological disorders and cosmetic applications as disclosed herein. All compound genera, species and conformations thereof, and syntheses thereof, of the patent applications and patents of this Table are incorporated by reference herein in their entireties, as exemplary compounds having utility for the presently claimed methods.

| Application/Pat. No. | Publication date | Compound class | Compound genus |
|---|---|---|---|
| US 2007/0021425 A1 | 25 January 2007; CWP | Reverse turn mimetics; All genera and compounds and salts thereof disclosed and claimed therein | (structure) |
| US 2010/0120758 A1 | 13 May 2010 | Reverse turn Reverse turn mimetics; All genera and compounds disclosed and claimed therein | (structure) |
| US 2010/0240662 A1 | 23 September 2010 | Reverse turn mimetics; All genera and compounds and salts thereof disclosed and claimed therein | (structure) |
| WO 2007/139346 A1 | 6 December 2007 | Reverse turn mimetics; All genera and compounds and salts thereof disclosed and claimed therein | (structure) |
| US 2004/0072831 A1 | 15 April 2004 | Reverse turn mimetics; All genera and compounds and salts thereof disclosed and claimed therein | (structure) |
| US 2007/0043052 | 22 February 2007 | Reverse turn mimetics; All genera and compounds and salts thereof disclosed and claimed therein | (structure) |
| US 2005/0059628 A1 | 17 March 2005 | Reverse turn mimetics; All genera and compounds and salts thereof disclosed and claimed therein | (structure) |

TABLE 1-continued

Exemplary CBP/β-catenin antagonists having utility for the treatment of aging and related dermatological disorders and cosmetic applications, having utility for and hair growth and/or regrowth and/or prevention of alleviation of hair loss, stimulating adenosing receptor expression, and for the treatment of dermatological disorders and cosmetic applications as disclosed herein. All compound genera, species and conformations thereof, and syntheses thereof, of the patent applications and patents of this Table are incorporated by reference herein in their entireties, as exemplary compounds having utility for the presently claimed methods.

| Application/Pat. No. | Publication date | Compound class | Compound genus |
| --- | --- | --- | --- |
| WO 2009/051399 A2 | 23 April 2009 | Reverse turn mimetics; All genera and compounds and salts thereof disclosed and claimed therein | (structure) |
| US 2006/0084655 A1 | 20 April 2006 | Reverse turn mimetics; All genera and compounds and salts thereof disclosed and claimed therein | (structure) |
| US 2008/0009500 A1 | 10 January 2008 | Reverse turn mimetics; All genera and compounds and salts thereof disclosed and claimed therein | (structure) |
| US 2010/0222303 | 2 September 2010 | Reverse turn mimetics; All genera and compounds and salts thereof disclosed and claimed therein | (structure) |
| U.S. Pat No. 6,413,963 | Issued 2 July 2002; MMX | Reverse turn mimetics; All genera and compounds and salts thereof disclosed and claimed therein | (structure) |
| U.S. Pat. No. 7,531,320 B2 | 12 May 2009 | Reverse turn mimetics; All genera and compounds and salts thereof disclosed and claimed therein | (structure) |
| U.S. Pat. No. 7,563,825 | 21 July 2009 | Reverse turn mimetics; All genera and compounds and salts thereof disclosed and claimed therein | (structure) |

TABLE 1-continued

Exemplary CBP/β-catenin antagonists having utility for the treatment of aging and related dermatological disorders and cosmetic applications, having utility for and hair growth and/or regrowth and/or prevention of alleviation of hair loss, stimulating adenosing receptor expression, and for the treatment of dermatological disorders and cosmetic applications as disclosed herein. All compound genera, species and conformations thereof, and syntheses thereof, of the patent applications and patents of this Table are incorporated by reference herein in their entireties, as exemplary compounds having utility for the presently claimed methods.

| Application/Pat. No. | Publication date | Compound class | Compound genus |
|---|---|---|---|
| WO 2010/128685 | 11 November 2010 | Reverse turn mimetics; All genera and compounds and salts thereof disclosed and claimed therein | 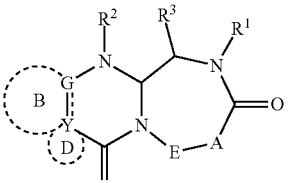 |
| WO 2010/044485 | 22 April 2010 | Reverse turn mimetics; All genera and compounds and salts thereof disclosed and claimed therein | 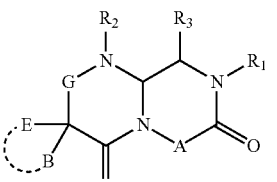 |

Exemplary Compound Genera (cont.)

US 2005/0250780. All compound genera, species and conformations thereof of US 2005/0250780, including the exemplary compounds of Tables 2-6 thereof, the claimed compounds, and including the disclosed respective syntheses, are incorporated herein by reference in their entirety as exemplary compounds for use in applicant's presently claimed methods.

Specific exemplary embodiments include a compound having the structure (I):

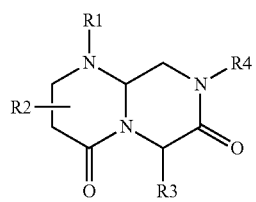

(I)

or a pharmaceutically acceptable salt or stereoisomer thereof,
wherein
R1 is —X—R5, where X is —C(=O)—, —C(=O)O—, —C(=O)NH— or —SO2-, and R5 is an amino acid side chain moiety or amino acid side chain derivative;
R2 is hydrogen or —Y—R6, where Y is a direct bond, —NH—, —NHC(=O)—, —NHC(=O)O—, —NHC(=O)NH— or —NHSO2-, and R6 is an amino acid side chain moiety or amino acid side chain derivative;
R3 is —Z—R7, where Z is a direct bond, —(CH2)mC(=O)NR8-, —(CH2)kNHC(=O) or —(CH2)kNHC(=O)NR8-, R7 and R8 are independently amino acid side chain moieties or amino acid side chain derivatives, m is an integer from 1 to 4 and k is 1 or 2;
R4 represents the remainder of the compound; and
wherein any two adjacent CH groups or adjacent NH and CH groups of the fused bicyclic compound optionally form a double bond.

Additional specific exemplary embodiments include those compounds of structure (I) wherein X is —C(C-0)0-, R2 is H, C1-C6alkyl, or C7-C11 arylalkyl; R3 is —(CH$_2$)$_{1-6}$—N(R')(R''), wherein R' and R'' are independently H or —C(NH)(NH2); R4 is C7-C11 arylalkyl; and R5 is C7-C11 arylalkyl, and wherein R4 and R5 are optionally and independently substituted with 1-3 halogen, 1-3 C1-C3 haloalkyl, or 1-3 C1-C3alkyl.

Further specific exemplary embodiments the compounds include those compounds of structure (I), wherein X is —C(C—O)NH—, R2 is H, C1-C6alkyl, or C7-C11 arylalkyl; R3 is

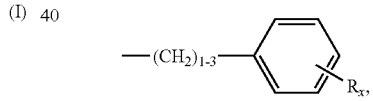

wherein Rx is H, OH or halo; R4 is C7-C11 arylalkyl; and R5 is C7-C11 arylalkyl, and wherein R2, R4 and R5 are optionally and independently substituted with 1-3 halogens, 1-3 C1-C3 haloalkyls, or 1-3 C1-C3alkyl.

US 2007/0021431. All compound genera, species and conformations thereof of US 2007/0021431, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having the structure (I):

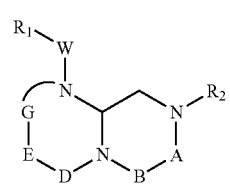

(I)I or a pharmaceutically acceptable salt or stereoisomer thereof, wherein A is —(CHR3)- or —(C=O)—, B is —(CHR4)-, —(C=O)—, D is —(CHR5)- or —(C=O)—, E is —(ZR6)-, —(C=O)—, G is —(XR7)$_n$—, —(CHR7)—(NR8)-, —(C=O)—(XR9)-, or —(C=O)—, W is —Y(C=O)—, —(C=O)NH—, —(SO2)- or nothing, Y is oxygen, sulfur or —NH—, X and Z is independently nitrogen or CH, n=0 or 1; and R1, R2, R3, R4, R5, R6, R7, R8 and R9 are the same or different and independently selected from an amino acid side chain moiety or derivative thereof, the remainder of the molecule, a linker and a solid support, and stereoisomers thereof, and as defined in US 2007/0021431.

US 2007/0021425. All compound genera, species and conformations thereof of US 2007/0021425, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having the structure following general formula (I):

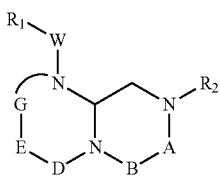

(I)

wherein A is —(CHR$_3$)— or —(C=O)—, B is —(CHR$_4$)— or —(C=O)—, D is —(CHR$_5$)— or —(C=O)—, E is —(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or is absent, Y is oxygen, sulfur, or —NH—, X and Z is independently nitrogen or CH, n=0 or 1; and R$_1$, R$_2$, R$_3$, R$_4$, R$_5$, R$_6$, R$_7$, R$_8$ and R$_9$ are the same or different and independently selected from an amino acid side chain moiety or derivative thereof, the remainder of the molecule, a linker and a solid support, and stereoisomers thereof, and as defined in US 2007/0021425.

In exemplary embodiments wherein A is —(CHR$_3$)—, B is —(C=O)—, D is —(CHR$_5$)—, E is —(C=O)—, and G is —(XR$_7$)$_n$—, the compounds of this invention have the following formula (II):

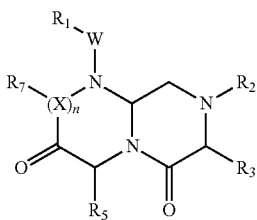

(II)

wherein W, X, Y and n are as defined above, and R$_1$, R$_2$, R$_3$, R$_5$ and R$_7$ are as defined in US 2007/0021425.

In exemplary embodiments wherein A is —(C=O)—, B is —(CHR$_4$)—, D is —(C=O)—, E is —(ZR$_6$)—, and G is —(C=O)—(XR$_9$)—, the compounds of this invention have the following formula (III):

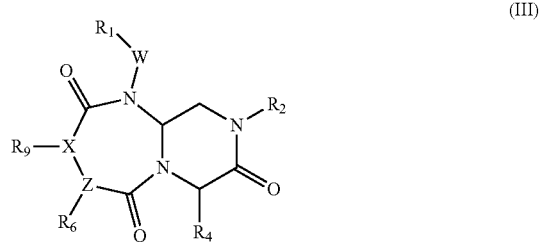

(III)

wherein W, X and Y are as defined above, Z is nitrogen or CH (with the proviso that when Z is CH, then X is nitrogen), and R$_1$, R$_2$, R$_4$, R$_6$ and R$_9$ are as defined in US 2007/0021425.

In exemplary embodiments wherein A is —(C=O)—, B is —(CHR$_4$)—, D is —(C=O)—, E is —(ZR$_6$)—, and G is (XR$_7$)$_n$—, the compounds of this invention have the following general formula (IV):

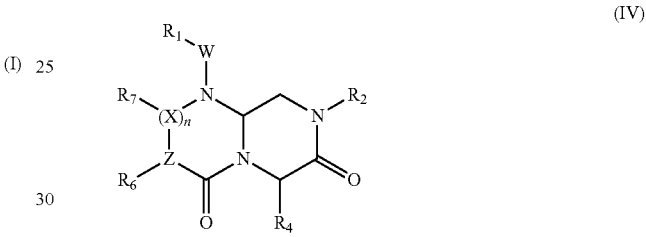

(IV)

wherein W, Y and n are as defined above, Z is nitrogen or CH (when Z is nitrogen, then n is zero, and when Z is CH, then X is nitrogen and n is not zero), and R$_1$, R$_2$, R$_4$, R$_6$ and R$_7$, are as defined in US 2007/0021425.

In certain embodiments, the compounds of this invention have the following general formula (VI):

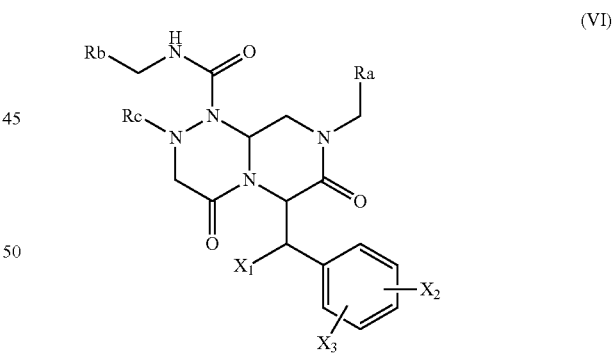

(VI)

wherein R$_a$ is a phenyl group; a substituted phenyl group having one or more substituents wherein the one or more substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-3}$alkoxy, nitro, carboxy, cyano, sulfuryl, and hydroxyl group; or a bicyclic aryl group having 8 to 11 ring members, which may have 1 to 3 heteroatoms selected from nitrogen, oxygen or sulfur; $R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy groups; $R_c$ is a saturated or unsaturated $C_{1-6}$alkyl, $C_{1-6}$alkoxy, perfluoro $C_{1-6}$alkyl group; and $X_1$, $X_2$, and $X_3$ may be the same or different and independently selected from hydrogen, hydroxyl, and halide.

The present invention is also related to prodrugs using the libraries containing one or more compounds of formula (I). A prodrug is typically designed to release the active drug in the body during or after absorption by enzymatic and/or chemical hydrolysis. The prodrug approach is an effective means of improving the oral bioavailability or i.v. administration of poorly water-soluble drugs by chemical derivatization to more water-soluble compounds. The most commonly used prodrug approach for increasing aqueous solubility of drugs containing a hydroxyl group is to produce esters containing an ionizable group; e.g., phosphate group, carboxylate group, alkylamino group (Fleisher et al., Advanced Drug *Delivery Reviews*, 115-130, 1996; Davis et al., *Cancer Res.*, 7247-7253, 2002, Golik et al., *Bioorg. Med. Chem. Lett.*, 1837-1842, 1996).

In certain embodiments, the prodrugs of the present invention have the following general formula (VII):

(VI)

wherein (VI) is general formula (VI) as described above; Y is oxygen, sulfur, or nitrogen of a group selected from $R_a$, $R_b$, $R_c$, $X_1$, $X_2$ and $X_3$;

$R_{10}$ is phosphate, hemisuccinate, phosphoryloxymethyloxycarbonyl, dimethylaminoacetate, amino acid, or a salt thereof; and wherein the prodrugs are capable of serving as a substrate for a phosphatase or a carboxylase and are thereby converted to compounds having general formula (VI).

US 2010/0120758. All compound genera, species and conformations thereof of US 2010/0120758, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having the structure (I):

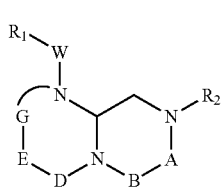
(I)

or a pharmaceutically acceptable salt or stereoisomer thereof, wherein A is —(CHR3)- or —(C=O)—, B is —(CHR4)-, —(C=O)—, D is —(CHR5)- or —(C=O)—, E is —(ZR6)-, —(C=O)—, G is —(XR7)n-, —(CHR7)-(NR8)-, —(C=O)—(XR9)-, or —(C=O)—, W is —Y(C=O)—, —(C=O)NH—, —(SO2)- or nothing, Y is oxygen, sulfur or —NH—, X and Z is independently nitrogen or CH, n=0 or 1; and R1, R2, R3, R4, R5, R6, R7, R8 and R9 are the same or different and independently selected from an amino acid side chain moiety or derivative thereof, the remainder of the molecule, a linker and a solid support, and stereoisomers thereof, and as defined in US 2010/0120758.

Specific exemplary embodiments include a compound of formula VI.

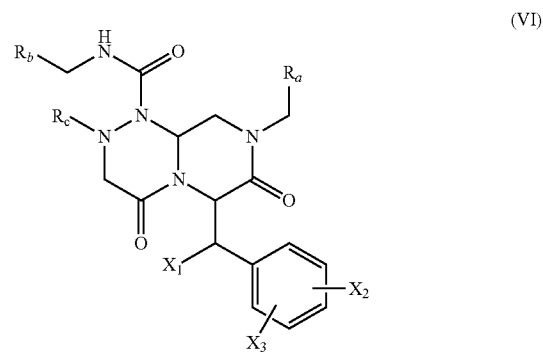
(VI)

as an isolated stereoisomer or a mixture of stereoisomers or as a pharmaceutically acceptable salt, wherein, Ra is a bicyclic aryl group having 8 to 11 ring members, which may have 1 to 3 heteroatoms selected from the group consisting of nitrogen, oxygen and sulfur;

Rb is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy groups;

Rc is a saturated or unsaturated C1-6alkyl, C1-6alkoxy, perfluoro C1-6alkyl group; and X1, X2, and X3 may be the same or different and independently selected from hydrogen, hydroxyl, and halide.

US 2010/0240662. All compound genera, species and conformations thereof of US 2010/0240662, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having the structure (I):

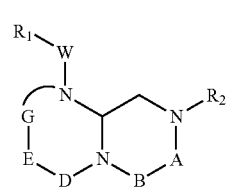
(I)

or a pharmaceutically acceptable salt or stereoisomer thereof, wherein A is —(CHR3)- or —(C=O)—, B is —(CHR4)-, —(C=O)—, D is —(CHR5)- or —(C=O)—, E is —(ZR6)-, —(C=O)—, G is —(XR7)$_n$—, —(CHR7)-(NR8)-, —(C=O)—(XR9)-, or —(C=O)—, W is —Y(C=O)—, —(C=O)NH—, —(SO2)- or nothing, Y is oxygen, sulfur or —NH—, X and Z is independently nitrogen or CH, n=0 or 1; and R1, R2, R3, R4, R5, R6, R7, R8 and R9 are the same or different and independently selected from an amino acid side chain moiety or derivative thereof, the remainder of the molecule, a linker and a solid support, and stereoisomers thereof, and as defined in US 2010/0240662.

In exemplary embodiments wherein A is —(CHR$_3$)— or —(C=O)—; B is —(CHR$_4$)— or —(C=O)—; D is —(CHR$_5$)— or —(C=O)—; E is —ZR$_6$— or —(C=O)—, wherein Z is CH or N; G is —XR$_7$— or —(C=O)—, wherein X is CH or N; W is —(C=O)NH—, —(C=O)S—, —S(O)$_2$— or nothing; and each of R$_1$, R$_2$, R$_3$, R$_4$, R$_5$, R$_6$ and R$_7$ is the same or different and independently an amino acid side chain moiety or an amino acid side chain derivative, the compounds of this invention have the following formula (IA):

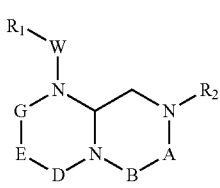

(IA)

Specific examples of R$_1$, R$_2$, R$_3$, R$_4$, R$_5$, R$_6$ and R$_7$ are as defined in US 2010/0240662.

WO 2007/139346. All compound genera, species and conformations thereof of US 2010/0240662, including the exemplary compounds of Tables 1-2 thereof, the claimed compounds, and including the disclosed respective syntheses, are incorporated herein by reference in their entirety as exemplary compounds for use in applicant's presently claimed methods.

Specific exemplary embodiments include a compound having formula (I):

[19]

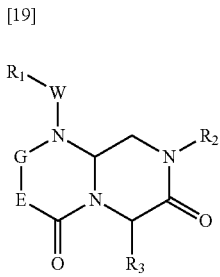

(I)

wherein:
E is —(ZR$_4$)— or —(C=O)—; G is nothing, —(XR$_5$)—, or —(C=O)—; W is —Y(C=O)—, —(C=O)NH—, —(SO$_2$)— or nothing; Y is oxygen or sulfur; X or Z is independently nitrogen or CH; R$_1$, R$_2$, R$_3$, R$_4$, and R$_5$ are the same or different and independently selected from the group consisting of: an amino acid side chain moiety; C$_{1-12}$alkyl or substituted C$_{1-12}$alkyl having one or more substituents independently selected from amino, guanidino, C$_{1-4}$alkylguanidino, diC$_{1-4}$alkylguanidino, amidino, C$_{1-4}$alkylamidino, diC$_{1-4}$alkylamidino, C$_{1-5}$alkylamino, diC$_{1-5}$alkylamino, sulfide, carboxyl, hydroxyl;
C$_{1-6}$alkoxy;
C$_{6-12}$aryl or substituted C$_{6-12}$aryl having one or more substituents independently selected from amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxyl, cyano, sulfuryl and hydroxyl;
monocyclic aryl-alkyl having 5 to 7 ring members, which may have 1 to 2 heteroatoms selected from nitrogen, oxygen or sulfur, or substituted monocyclic aryl-alkyl having one or more substituents independently selected from amino, amidino, guanidino, hydrazino, C$_{1-4}$alkylamino, C$_{1-4}$dialkylamino, halogen, perfluoro C$_{1-4}$alkyl, C1-6alkyl, C$_{1-3}$alkoxy, nitro, carboxy, cyano, sulfuryl and hydroxyl;
bicyclic aryl-alkyl having 8 to 10 ring members, which may have 1 to 2 heteroatoms selected from nitrogen, oxygen or sulfur, or substituted bicyclic aryl-alkyl having one or more substituents independently selected from halogen, C$_{1-6}$alkyl, C$_{1-6}$alkoxy, cyano, hydroxyl; tricyclic aryl-alkyl having 5 to 14 ring members, which may have 1 to 2 heteroatoms selected from nitrogen, oxygen or sulfur, or substituted bicyclic aryl-alkyl having one or more substituents independently selected from halogen, C$_{1-6}$alkyl, C$_{1-6}$alkoxy, cyano, hydroxyl; arylC$_{1-4}$alkyl or substituted arylC$_{1-4}$alkyl having one or more substituents independently selected from amino, amidino, guanidino, hydrazino, C$_{1-4}$alkylamino, C$_{1-4}$dialkylamino, C$_{3-6}$cycloalkyl, halogen, perfluoroC$_{1-4}$alkyl, C$_{1-6}$alkyl, C$_{1-3}$alkoxy, nitro, carboxyl, cyano, sulfuryl, hydroxyl, amide, C$_{1-6}$alkyloxyC$_{1-6}$acyl and morphorlinylC$_{1-6}$alkyl;
cycloalkylalkyl or substituted cycloalkylalkyl having one or more substituents independently selected from amino, amidino, guanidino, hydrazino, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxyl, cyano, sulfuryl and hydroxyl; and cycloalkyl or substituted cycloalkyl having one or more substituents independently selected from amino, amidino, guanidino, hydrazino, C$_{1-4}$alkylamino, C$_{1-4}$dialkylamino, halogen, perfluoroC$_{1-4}$alkyl, C$_{1-4}$alkyl, C$_{1-3}$alkoxy, nitro, carboxyl, cyano, sulfuryl and hydroxyl.

In certain embodiments, R$_1$, R$_2$, R$_3$, R$_4$, and R$_5$ are the same or different and independently selected from the group consisting of:
C$_{i-12}$alkyl or substituted C$^{\wedge}{}_{12}$alkyl having one or more substituents independently selected from amino, guanidino, C$_{1-4}$alkylguanidino, diC$_{1-4}$alkylguanidino, amidino, C1-4alkylamidino, diC1-4alkylamidino, C$_{1-5}$alkylamino, diC$_{1-5}$alkylamino, sulfide, carboxyl, hydroxyl;
C$_{1-6}$alkoxy; cycloalkylC$_{1-3}$alkyl; cycloalkyl;
phenyl or substituted phenyl having one or more substituents independently selected from amino, amidino, guanidino, hydrazino, C$_{1-4}$alkylamino, C$_{1-4}$dialkylamino, halogen, perfluoroC$_{1-4}$alkyl, C$_{1-6}$alkyl, C$_{1-3}$alkoxy, nitro, carboxyl, cyano, sulfuryl, hydroxyl;
phenylC$_{2-4}$alkyl or phenylC$_{2-4}$alkyl having one or more substituents independently selected from amino, amidino, guanidino, hydrazino, C$_{1-4}$alkylamino, C$_{1-4}$dialkylamino, halogen, perfluoroC$_{1-4}$alkyl, C$_{1-6}$alkyl, C$_{1-3}$alkoxy, nitro, carboxyl, cyano, sulfuryl, sulfide, hydroxyl; naphthyl or substituted naphthyl having one or more substituents independently selected from amino, amidino, guanidino, hydrazino, C$_{1-4}$alkylamino, C$_{1-4}$dialkylamino, halogen, perfluoroC$_{1-4}$alkyl, C$_{1-6}$alkyl, C$_{1-3}$alkoxy, nitro, carboxyl, cyano, sulfuryl, hydroxyl; naphthylC$_{1-4}$alkyl or naphthylC$_{1-4}$alkyl having one or more substituents independently selected from amino, amidino, guanidino, hydrazino, $C_{1-4}$alkylamino, $C_{1-4}$dialkylamino, halogen, perfluoro$C_{1-4}$alkyl, $C_{1-6}$alkyl, $C_{1-3}$alkoxy, nitro, carboxyl, cyano, sulfuryl, hydroxyl; benzyl or substituted benzyl having one or more substituents independently selected from amino, amidino, guanidino, hydrazino, $C_{1-4}$alkylamino, $C_{1-4}$diaalkylamino, halogen, perfluoro $C_{1-4}$alkyl, trifluoro$C_{1-4}$alkyl; $C_{1-6}$alkyl, $C_{1-3}$alkoxy, nitro, carboxyl, cyano, sulfuryl and hydroxyl; bisphenylmethyl or substituted bisphenylmethyl having one or more substituents independently selected from amino, amidino, guanidino, hydrazino, $C_{1-4}$alkylamino, $C_{1-4}$ dialkylamino, halogen, perfluoro $C_{1-4}$alkyl, $C_{1-6}$alkyl, $C_{1-3}$alkoxy, nitro, carboxyl, cyano, sulfuryl and hydroxyl;

benzylphenyl amide, or substituted benzylphenyl amide having one or more substituents independently selected from amino, amidino, guanidino, hydrazino, $C_{1-4}$alkylamino, $C_{1-4}$dialkylamino, halogen, perfluoro $C_{1-4}$alkyl, $C_{1-6}$alkyl, $C_{1-3}$alkoxy, nitro, carboxyl, cyano, sulfuryl and hydroxyl;

pyridyl or substituted pyridyl having one or more substituents independently selected from amino, amidino, guanidino, hydrazino, $C_{1-4}$alkylamino, $C_{1-4}$dialkylamino, halogen, perfluoro $C_{1-4}$alkyl, $C_{1-6}$alkyl, $C_{1-3}$alkoxy, nitro, carboxyl, cyano, sulfuryl and hydroxyl;

[50] pyridyl$C_{1-4}$alkyl, or substituted pyridyl$C_{1-4}$alkyl having one or more substituents independently selected from amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxyl, cyano, sulfuryl and hydroxyl;

pyrimidyl$C_{1-4}$alkyl, or substituted pyrimidyl$C_{1-4}$alkyl having one or more substituents independently selected from amino, amidino, guanidino, hydrazino, $C_{1-4}$alkylamino, $C_{1-4}$dialkylamino, halogen, perfluoro $C_{1-4}$alkyl, $C_{1-6}$alkyl, $C_{1-3}$alkoxy, nitro, carboxyl, cyano, sulfuryl and hydroxyl;

triazin-2-yl$C_{1-4}$alkyl, or substituted triazin-2-yl$C_{1-4}$alkyl having one or more substituents independently selected from amino, amidino, guanidino, hydrazino, $C_{1-4}$alkylamino, $C_{1-4}$dialkylamino, halogen, perfluoro $C_{1-4}$alkyl, $C_{1-6}$alkyl, $C_{1-3}$alkoxy, nitro, carboxy, cyano, sulfuryl and hydroxyl;

imidazolyl$C_{1-4}$alkyl or substituted imidazolyl$C_{1-4}$alkyl having one or more substituents independently selected from amino, amidino, guanidino, hydrazino, $C_{1-4}$alkylamino, $C_{1-4}$dialkylamino, halogen, perfluoro $C_{1-4}$alkyl, $C_{1-6}$alkyl, $C_{1-3}$alkoxy, nitro, carboxy, cyano, sulfuryl and hydroxyl;

benzothiazolin$C_{1-4}$alkyl or substituted benzothiazolin$C_{1-4}$alkyl having one or more substituents independently selected from amino, amidino, guanidino, hydrazino, $C_{1-4}$alkylamino, $C_{1-4}$dialkylamino, halogen, perfluoro $C_{1-4}$alkyl, $C_{1-6}$alkyl, $C_{1-3}$alkoxy, nitro, carboxy, cyano, sulfuryl and hydroxyl;

phenoxazin$C_{1-4}$alkyl; benzyl p-tolyl ether; phenoxybenzyl; N-amidinopiperazinyl-N—$C_{1-4}$alkyl; quinoline$C_{1-4}$alkyl; N-amidinopiperazinyl; N-amidinopiperidinyl$C_{1-4}$alkyl; 4-aminocyclohexyl$C_{1-2}$alkyl; and 4-aminocyclohexyl.

In certain embodiments, E is —($ZR_4$)— and G is —($XR_5$)—, wherein Z is CH and X is nitrogen, and the compound has the following general formula (II):

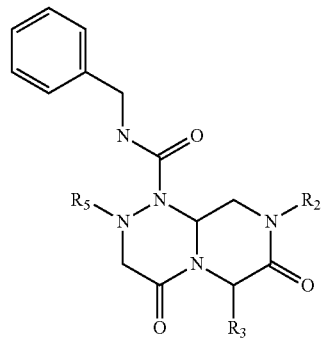

wherein $R_2$, $R_3$, and $R_5$ are as defined as in formula (I).

In certain embodiments, the compound has the following general formula (III):

[68]

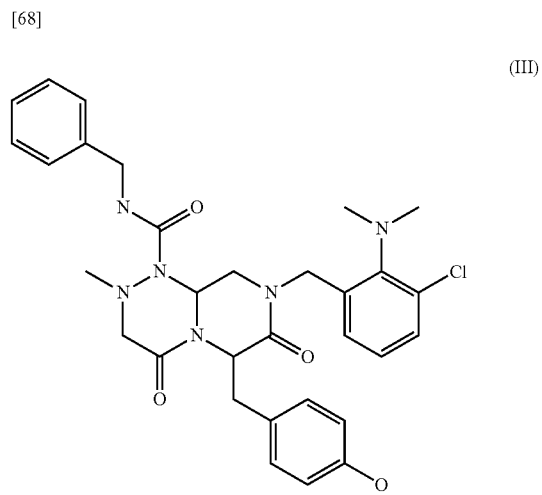

In certain embodiments, E is —($ZR_4$)— and G is nothing, wherein Z is nitrogen, and the compound has the following general formula (IV):

[70]

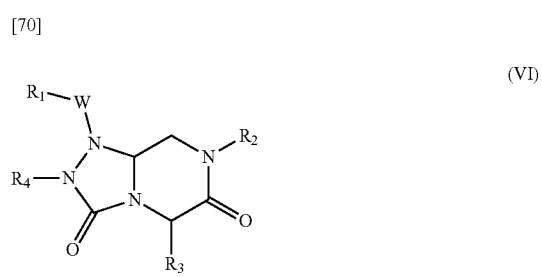

wherein $R_1$, $R_2$, $R_3$, $R_4$, and W are as defined in formula (I).

In certain embodiments, E is —($ZR_4$)— and G is —($XR_5$)—, wherein Z and X are independently CH, and the compound has a stricture of Formula (V):

[73]

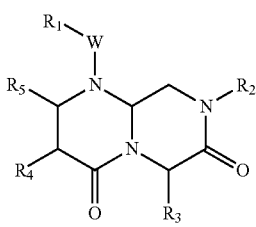

(V)

wherein $R_1$, $R_2$, $R_3$, $R_4$, $R_5$, and W are as defined in formula (I).

In certain embodiments, the compound has the following general formula (VI):

[76]

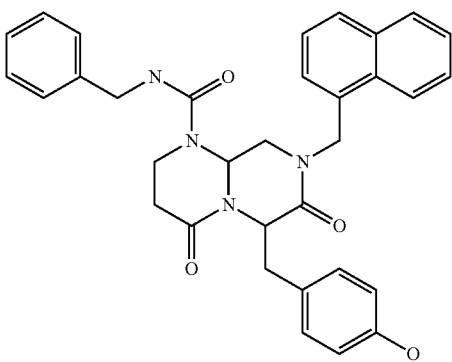

(VI)

US 2004/0072831. All compound genera, species and conformations thereof of US 2004/0072831, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having formula (I):

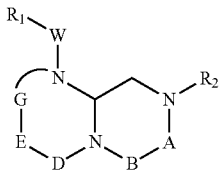

(I)

wherein: A is —(CHR$_3$)— or —(C=O)—, B is —(CHR$_4$)— or —(C=O)—, D is —(CHR$_5$)— or —(C=O)—, E is —(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or is absent, Y is oxygen or sulfur, X and Z is independently nitrogen or CH, n=0 or 1; and $R_1$, $R_2$, $R_3$, $R_4$, $R_5$, $R_6$, $R_7$, $R_8$ and $R_9$ are the same or different and independently selected from an amino acid side chain moiety or derivative thereof, the remainder of the molecule, a linker and a solid support, and stereoisomers thereof, and as defined in US 2004/0072831.

In embodiments wherein A is —(CHR$_3$)—, B is —(C=O)—, D is —(CHR$_5$)—, E is —(C=O)—, and G is —(XR$_7$)$_n$—, the compounds of this invention have the following formula (II):

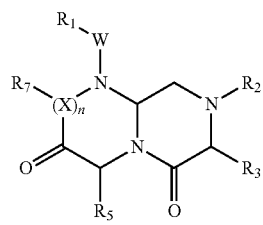

(II)

wherein W, X, Y and n are as defined above, and $R_1$, $R_2$, $R_3$, $R_5$ and $R_7$ are as defined in US 2004/0072831.

In embodiments wherein A is —(C=O)—, B is —(CHR$_4$)—, D is —(C=O)—, E is —(ZR$_6$)—, and G is —(C=O)—(XR$_9$)—, the compounds of this invention have the following formula (III):

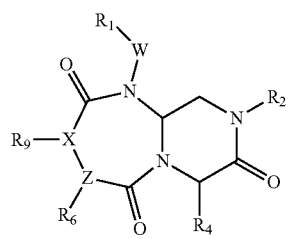

(III)

wherein W, X and Y are as defined above, Z is nitrogen or CH (with the proviso that when Z is CH, then X is nitrogen), and $R_1$, $R_2$, $R_4$, $R_6$ and $R_9$ are as defined in US 2004/0072831.

In embodiments wherein A is —(C=O)—, B is —(CHR$_4$)—, D is —(C=O)—, E is —(ZR$_6$)—, and G is (XR$_7$)$_n$—, the compounds of this invention have the following general formula (IV):

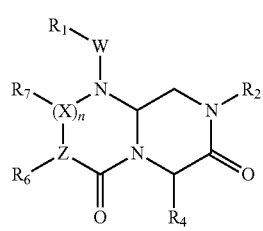

(IV)

wherein W, Y and n are as defined above, Z is nitrogen or CH (when Z is nitrogen, then n is zero, and when Z is CH, then X is nitrogen and n is not zero), and $R_1$, $R_2$, $R_4$, $R_6$ and $R_7$ are as defined in US 2004/0072831.

In certain embodiments, wherein $R_1$, $R_2$, $R_3$, $R_4$, $R_5$, $R_6$, $R_7$, $R_8$ and $R_9$ are independently selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, Phenyl, substituted phenyl(where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidazonyl, C$_{1-4}$alkylamino, Cli$_4$dialkylamino, halogen, perfluoro C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl, (where the substituents are independently selected from one or more of amino amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy or nitro, carboxy, cyano, sulfuryl or hydroxyl), triazin-2-yl-C$_{1-4}$alkyl, substituted triazin-2-yl-C$_{1-4}$alkyl (where the triazine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazoC$_{1-4}$alkyl, substituted imidazol C$_{1-4}$alkyl (where the imidazole substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazolinylC$_{1-4}$alkyl, N-amidinopiperazinyl-N—C$_{0-4}$alkyl, hydroxyC$_{2-5}$alkyl, C$_{1-5}$alkylaminoC$_{2-5}$alkyl, hydroxyC$_{2-5}$alkyl, C$_{1-5}$alkylaminoC$_{2-5}$alkyl, C$_{1-5}$dialkylaminoC$_{2-5}$alkyl, N-amidinopiperidinylC$_{1-4}$ alkyl and 4-aminocyclohexylC$_{0-2}$alkyl.

US 2007/0043052. All compound genera, species and conformations thereof of US 2007/0043052, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having formula (I):

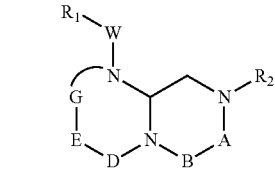

(I)

wherein: A is —(CHR$_3$)— or —(C═O)—, B is —(CHR$_4$)— or —(C═O)—, D is —(CHR$_5$)— or —(C═O)—, E is —(ZR$_6$)— or —(C═O)—, G is —(XR$_7$)$_n$—, —(CHR$_7$)—(NR$_8$)—, —(C═O)—(XR$_9$)—, or —(C═O)—, W is —Y(C═O)—, —(C═O)NH—, —(SO$_2$)— or is absent, Y is oxygen or sulfur, X and Z is independently nitrogen or CH, n=0 or 1; and R$_1$, R$_2$, R$_3$, R$_4$, R$_5$, R$_6$, R$_7$, R$_8$ and R$_9$ are the same or different and independently selected from an amino acid side chain moiety or derivative thereof, the remainder of the molecule, a linker and a solid support, and stereoisomers thereof, and as defined in US 2007/0043052.

In embodiments wherein A is —CHR$_3$)—, B is —(C═O)—, D is —(CHR$_5$)— E is —(C═O)—, and G is —XR$_7$)$_n$—, the compounds of this invention have the following formula (II):

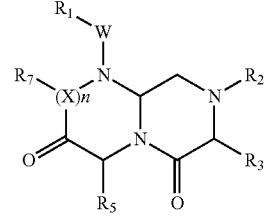

(II)

wherein W, X, Y and n are as defined above, and R$_1$, R$_2$, R$_3$, R$_5$ and R$_7$ are as defined in US 2007/0043052.

In embodiments wherein A is —(C═O)—, B is —(CHR$_4$)—, D is —(C═O)—, E is —(ZR$_6$)—, and G is —(C═O)—(XR$_9$)—, the compounds of this invention have the following formula (III):

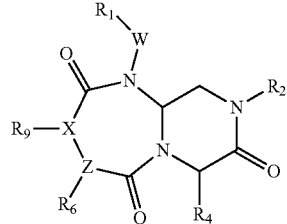

(III)

wherein W, X and Y are as defined above, Z is nitrogen or CH (with the proviso that when Z is CH, then X is nitrogen), and R$_1$, R$_2$, R$_4$, R$_6$ and R$_9$ are as defined in US 2007/0043052.

In embodiments wherein A is —(C═O)—, B is —(CHR$_4$)—, D is —(C═O)—, E is —(ZR$_6$)—, and G is (XR$_7$)$_n$—, the compounds of this invention have the following general formula (IV):

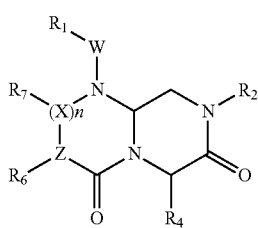

(IV)

wherein W, Y and n are as defined above, Z is nitrogen or CH (when Z is nitrogen, then n is zero, and when Z is CH, then X is nitrogen and n is not zero), and $R_1$, $R_2$, $R_4$, $R_6$ and $R_7$, are as defined in US 2007/0043052.

In certain embodiments, the compounds of this invention have the following general formula (VI):

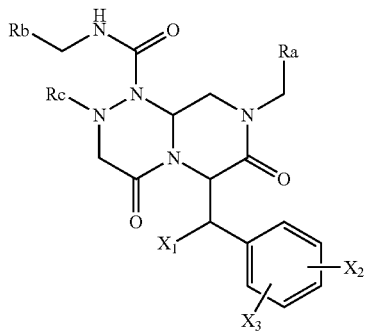

(VI)

wherein $R_a$ is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group having 8 to 11 ring members, which may have 1 to 3 heteroatoms selected from nitrogen, oxygen or sulfur; $R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy groups; $R_c$ is a saturated or unsaturated $C_{1-6}$alkyl, $C_{1-6}$alkoxy, perfluoro $C_{1-6}$alkyl group; and $X_1$, $X_2$, and $X_3$ may be the same or different and independently selected from hydrogen, hydroxyl, and halide.

In certain embodiments, prodrugs have the following general formula (VII):

 (VI)

wherein (VI) is general formula (VI) as described above; Y is oxygen, sulfur, or nitrogen of a group selected from $R_a$, $R_b$, $R_c$, $X_1$, $X_2$ and $X_3$;

$R_{10}$ is phosphate, hemisuccinate, hemimalate, phosphoryloxymethyloxycarbonyl, dimethylaminoacetate, dimethylaminoalkylcarbamates, hydroxyalkyls, amino acid, glycosyl, substituted or unsubstituted piperidine oxycarbonyl, or a salt thereof; and wherein the prodrugs are capable of serving as a substrate for a phosphatase or a carboxylase and are thereby converted to compounds having general formula (VI).

In some embodiments, $R_{10}$ of the general formula (VII) is not an amino acid group or a phospho-amino acid group. US 2005/0059628. All compound genera, species and conformations thereof of US 2005/0059628, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having formula (I):

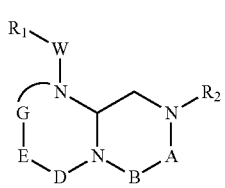

(I)

wherein: A is —(CHR$_3$)— or —(C=O)—, B is —(CHR$_4$)— or —(C=O)—, D is —(CHR$_5$)— or —(C=O)—, E is —(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or is absent, Y is oxygen or sulfur, X and Z is independently nitrogen or CH, n=0 or 1; and $R_1$, $R_2$, $R_3$, $R_4$, $R_5$, $R_6$, $R_7$, $R_8$ and $R_9$ are the same or different and independently selected from an amino acid side chain moiety or derivative thereof, the remainder of the molecule, a linker and a solid support, and stereoisomers thereof, and as defined in US 2005/0059628.

In certain embodiments, $R_1$, $R_2$, $R_3$, $R_4$, $R_5$, $R_6$, $R_7$, $R_8$ and $R_9$ of formula (I) are independently selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino-$C_{2-5}$alkyl, amidino$C_{2-5}$alkyl, $C_{1-4}$alkylamidino$C_{2-5}$alkyl, di$C_{1-4}$alkylamidino$C_{2-5}$alkyl, $C_{1-3}$alkoxy, phenyl, substituted phenyl(where the substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl, substituted pyridyl, (where the substituents are independently selected from one or more of amino amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl$C_{1-4}$alkyl, substituted pyridyl$C_{1-4}$ alkyl (where the pyridine substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyrimidyl$C_{1-4}$alkyl, substituted pyrimidyl$C_{1-4}$alkyl (where the pyrimidine substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazo$C_{1-4}$alkyl, substituted imidazol $C_{1-4}$alkyl (where the imidazole substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazolinyl$C_{1-4}$alkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$ alkyl and 4-aminocyclohexyl$C_{0-2}$alkyl.

In certain embodiments, A is —(CHR$_3$)—, B is —(C=O)—, D is —(CHR$_5$)—, E is —(C=O)—, G is —(XR$_7$)$_n$—, and the compound has the following general formula (II):

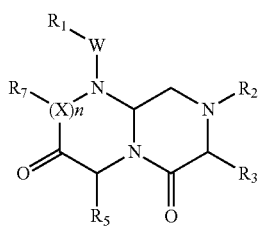

(II)

wherein $R_1$, $R_2$, $R_3$, $R_5$, $R_7$, W, X and n are as defined as in formula (I).

In certain embodiments, A is —(C=O)—, B is —(CHR$_4$)—, D is —(C=O)—, E is —(ZR$_6$)—, G is —(C=O)—(XR$_9$)—, and the compound has the following general formula (III):

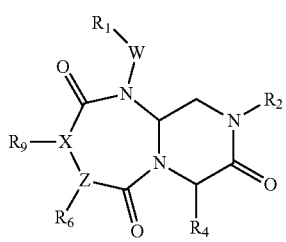

(III)

wherein $R_1$, $R_2$, $R_4$, $R_6$, $R_9$, W and X are as defined in formula (I), Z is nitrogen or CH (when Z is CH, then X is nitrogen).

In certain embodiments, A is —(C=O)—, B is —(CHR$_4$)—, D is —(C=O)—, E is —(ZR$_6$)—, G is —(XR$_7$)$_n$—, and the compound has the following general formula (IV):

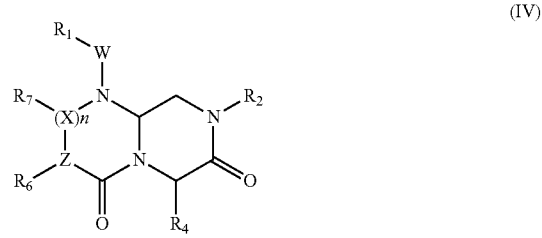

(IV)

wherein $R_1$, $R_2$, $R_4$, $R_6$, $R_7$, W, X and n are as defined in formula (I), and Z is nitrogen or CH, with the proviso that when Z is nitrogen, then n is zero, and when Z is CH, then X is nitrogen and n is not zero.

In certain embodiments, the compound has the following general formula (VI):

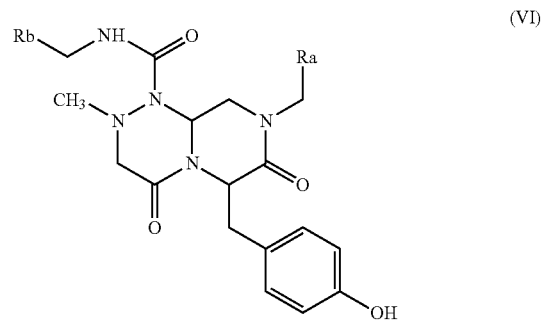

(VI)

wherein, $R_a$ is a bicyclic aryl group having 8 to 11 ring members, which may have 1 to 3 heteroatoms selected from nitrogen, oxygen or sulfur, and $R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy group. Optionally, $R_a$ is naphthyl, quinolinyl or isoquinolinyl group, and $R_b$ is phenyl, pyridyl or piperidyl, all of which may be substituted with one or more substituents selected from a group consisting of halide, hydroxy, cyano, lower alkyl, and lower alkoxy group. In certain embodiments, $R_a$ is naphthyl, and $R_b$ is phenyl, which may be substituted with one or more substituents selected from a group consisting of halide, hydroxy, cyano, lower alkyl, and lower alkoxy group.

In certain embodiments, the compound is selected from COMPOUNDS 1, 3, 4, and 5 as defined in US 2005/0059628.

WO 2009/051399. All compound genera, species and conformations thereof of WO 2009/051399, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having formula (I):

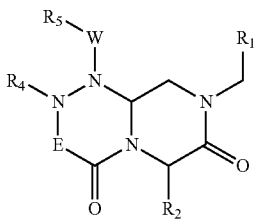

(I)

wherein E is —ZR3— or —(C=O)—, wherein Z is CH or N; W is —(C=O)—, —(C=O)NH—, —(C=O)O—, —(C=O)S—, —S(O)z— or a bond; and each of $R_1, R_2, R_3, R_4$ and $R_5$ is the same or different and independently an amino acid side chain moiety or an amino acid side chain derivative. The reverse turn mimetic compound may be present as an isolated stereoisomer or a mixture of stereoisomers or as a pharmaceutically acceptable salt thereof. In certain embodiments, $R_1$ of compounds of Formula (I) is indazolyl or substituted indazolyl. Specific examples of $R_1, R_2, R_3, R_4$ and $R_5$ are as defined in WO 2009/051399.

In embodiments wherein E is CHR3, the compounds of this invention have the following Formula (II):

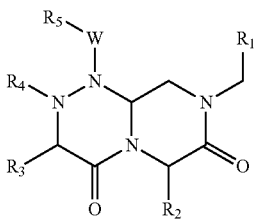

(II)

wherein W is as defined above, and $R_1, R_2, R_3, R_4$ and $R_5$ are as defined in WO 2009/051399.

In certain embodiments, the compounds of this invention have the following general Formula (III):

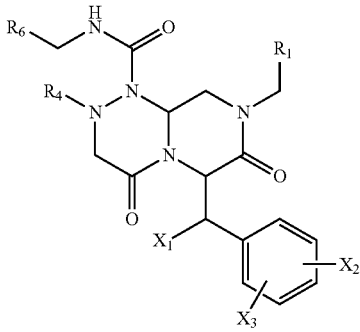

(III)

wherein $R_1, R_4, R_6, X_1, X_2$ and $X_3$ are as defined in WO 2009/051399.

In certain embodiments, the prodrugs of the present invention have the following general Formula (IV):

(III)-R7

(IV)

wherein (III) is Formula (III) as described above; one of $R_1, R_4, R_6, X_1, X_2$ and $X_3$ is linked to $R_7$ via Y; Y is an oxygen, sulfur, or nitrogen in $R_1$, $R_4$ or $R_6$ or an oxygen in $X_1, X_2$, or $X_3$; and $R_7$ is hydroxyalkyl, glycosyl, phosphoryloxymethyloxycarbonyl, substituted or unsubstituted piperidine carbonyloxy, or a salt thereof; or Y—$R_7$ is an amino acid residue, a combination of amino acid residues, phosphate, hemimalate, hemisuccinate, dimethylaminoalkylcarbamate, dimethylaminoacetate, or a salt thereof; and when not linked to $R_7$: $R_1, R_4, R_6, X_1, X_2$ and $X_3$ are defined in WO 2009/051399.

US 2006/0084655. All compound genera, species and conformations thereof of US 2006/0084655, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having formula (I):

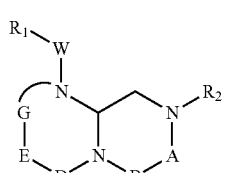

(I)

wherein: A is —(CHR3)— or —(C=O)—, B is —(CHR4)— or —(C=O)—, D is —(CHR5)— or —(C=O)—, E is —(ZR6)— or —(C=O)—, G is —(XR7)n—, —(CHR7)—(NR8)—, —(C=O)—(XR9)—, or —(C=O)—, W is —Y(C=O)—, —(C=O)NH—, —(SO2)— or is absent, Y is oxygen, sulfur, or —NH—, X and Z is independently nitrogen or CH, n=0 or 1; and $R_1, R_2, R_3, R_4, R_5, R_6, R_7, R_8$ and $R_9$ are the same or different and independently selected from an amino acid side chain moiety or derivative thereof, the remainder of the molecule, a linker and a solid support, and stereoisomers thereof, and as defined in US 2006/0084655.

In an embodiment wherein A is —(CHR3)—, B is —(C=O)—, D is —(CHR5)—, E is —(C=O)—, and G is —(XR7)n—, the compounds of this invention have the following formula (II):

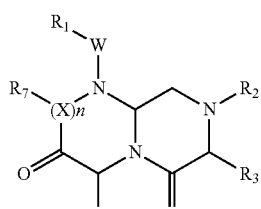

(II)

wherein W, X, Y and n are as defined above, and $R_1, R_2, R_3, R_5$ and $R_7$ are as defined in US 2006/0084655.

In an embodiment wherein A is —(C=O)—, B is —(CHR4)—, D is —(C=O)—, E is —(ZR6)—, and G is —(C=O)—(XR9)—, the compounds of this invention have the following formula (III):

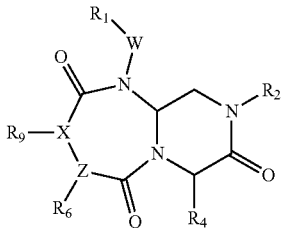

(III)

wherein W, X and Y are as defined above, Z is nitrogen or CH (with the proviso that when Z is CH, then X is nitrogen), and $R_1$, $R_2$, $R_4$, $R_6$ and $R_9$ are as defined in US 2006/0084655.

In an embodiment wherein A is —C(=O)—, B is —(CHR$_4$)—, D is —(C=O)—, E is —(ZR$_6$)—, and G is (XR$_7$)$_n$—, the compounds of this invention have the following general formula (IV):

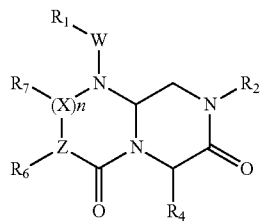

(IV)

wherein W, Y and n are as defined above, Z is nitrogen or CH (when Z is nitrogen, then n is zero, and when Z is CH, then X is nitrogen and n is not zero), and $R_1$, $R_2$, $R_4$, $R_6$ and $R_7$, are as defined in US 2006/0084655.

US 2008/0009500. All compound genera, species and conformations thereof of US 2008/0009500, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having formula (I):

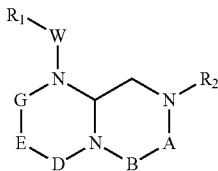

(I)

wherein A is —(C=O)—CHR3-, or —(C=O), B is N—R5- or —CHR6-, D is —(C=O)—(CHR7)- or —(C=O)—, E is —(ZR8)- or (C=O), G is —(XR9)n—, —(CHR10)-(NR6)-, —(C=O)—(XR12)-, -(or nothing)-, —(C=O)—, X—(C=O)—R13, X—(C=O)—NR13R14, X—(SO2)-R13, or X—(C=O)—OR13, W is —Y(C=O)—, —(C=O)NH—, —(SO2)-, —CHR14, (C=O)—(NR15)-, substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, or nothing, Y is oxygen or sulfur, X and Z is independently nitrogen or CH, n=0 or 1; and R1, R2, R3, R4, R5, R6, R7, R8, R9R10, R11, R12, R13, R14, and R15 are the same or different and independently selected from an amino acid side chain moiety or derivative thereof, the remainder of the molecule, a linker and a solid support, and stereoisomers, salts, and prodrugs thereof, and a pharmaceutically acceptable carrier.

In certain embodiment, R1, R2, R3, R4, R5, R6, R7, R8, R9, R10, R11, R12, R13, R14, are R15 are independently selected from the group consisting of aminoC2-5alkyl, guanidinoC2-5alkyl, C1-4alkylguanidino C2-5alkyl, diC1-4alkylguanidino-C2-5alkyl, amidinoC2-5alkyl, C1-4alkylamidino C2-5alkyl, diC1-4alkylamidino C2-5alkyl, C1-3alkoxy, phenyl, substituted phenyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), bis-phenyl methyl, substituted bisphenyl methyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyridyl, substituted pyridyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyridylC1-4alkyl, substituted pyridylC1-4alkyl (where the pyridine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyrimidylC1-4alkyl, substituted pyrimidylC1-4alkyl (where the pyrimidine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy or nitro, carboxy, cyano, sulfuryl or hydroxyl), triazin-2-yl-C1-4alkyl, substituted triazin-2-yl-C1-4alkyl (where the triazine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), imidazoC1-4alkyl, substituted imidazol C1-4alkyl (where the imidazole substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl, hydroxyl, or methyl), imidazolinylC1-4alkyl, N-amidinopiperazinyl-N—C0-4alkyl, hydroxyC2-5alkyl, C1-5alkylaminoC2-5alkyl, hydroxyC2-5alkyl, C1-5alkylaminoC2-5alkyl, C1-5 dialkylaminoC2-5alkyl, N-amidinopiperidinylC1-4alkyl and 4-aminocyclohexylC0-2alkyl.

In certain aspects, A is —(CHR3)-(C=O)—, B is —(NR4)-, D is (C=O)—, E is —(ZR6)-, G is —(C=O)—(XR9)-, and the compound has the following general formula (III):

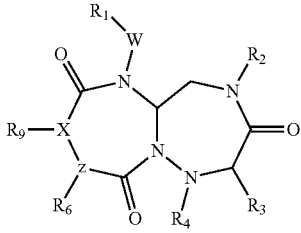

wherein Z is nitrogen or CH, and when Z is CH, X is nitrogen.

In certain aspects, A is —O—CHR3-, B is —NR4-, D is —(C=O)—, E is —(ZR6)-, Gi is (XR7)n—, the compound has the following formula (IV):

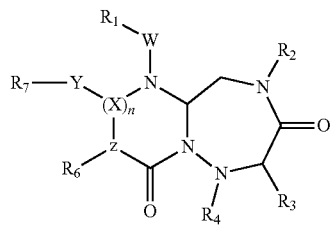

wherein R1, R2, R4, R6, R7, R8W, X and n are as defined above, Y is —C=O, —(C=O)—O—, —(C=O)—NR8, —SO2-, or nothing, and Z is nitrogen or CH (when Z is nitrogen, then n is zero, and when Z is CH, then X is nitrogen and n is not zero).

In certain embodiment, when A is —(C=O), B is —(CHR6)-, D is —(C=O)—, E is —(ZR8)-, and G is —(NH)— or —(CH2)-, and W is a substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, the compound has the following formula (V):

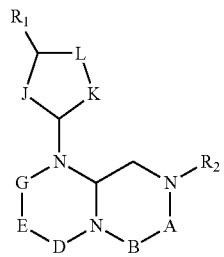

wherein K is nitrogen, oxygen, or sulfur, L is nitrogen, oxygen, —(CH)—, or —(CH2)-, J is nitrogen, oxygen, or sulfur, Z is nitrogen or CH, and R1, R2, R6, R8, and R13 are selected from an amino acid side chain moiety.

Particular embodiments provide a compound having the general formula (VI):

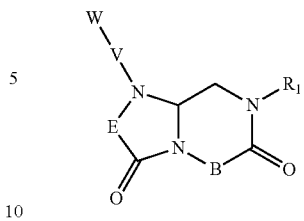

wherein B is —(CHR2)-, —(NR2)-, E is —(CHR3)-, V is —(XR4)- or nothing, W is —(C=O)—(XR5R6), —(SO2)-, substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, X is independently nitrogen, oxygen, or CH, and R1, R2, R3, R4, R5 and R6 are selected from an amino acid side chain moiety or derivative thereof, the remainder of the molecule, a linker and solid support, and stereoisomers, salts and prodrugs thereof. In certain aspects, R1, R2, R3, R4, R5, R6, R7, R8, R9, R10, R11, R12, R13, R14, are R15 are independently selected from the group consisting of aminoC2-5alkyl, guanidinoC2-5alkyl, C1-4alkylguanidino C2-5alkyl, diC1-4alkylguanidino-C2-5alkyl, amidino C2-5alkyl, C1-4alkylamidino C2-5alkyl, diC1-4alkylamidino C2-5alkyl, C1-3alkoxy, phenyl, substituted phenyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), naphthyl, substituted naphthyl (where the substituents are independently selected from one or more of amino, amidino, guanidine, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyridyl, substituted pyridyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyridylC1-4alkyl, substituted pyridylC1-4alkyl (where the pyridine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyrimidylC1-4alkyl, substituted pyrimidylC1-4alkyl (where the pyrimidine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy or nitro, carboxy, cyano, sulfuryl or hydroxyl), triazin-2-yl-C1-4alkyl, substituted triazin-2-yl-C1-4alkyl (where the triazine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), imidazoC1-4alkyl, substituted imidazol C1-4alkyl (where the imidazole substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl, hydroxyl, or methyl), imidazolinylC1-4alkyl, N-amidinopiperazinyl-N—C0-4alkyl, hydroxyC2-5alkyl, C1-5alkylaminoC2-5alkyl, hydroxyC2-5alkyl, C1-5alkylaminoC2-5alkyl, C1-5 dialkylaminoC2-5alkyl, N-amidinopiperidinylC1-4alkyl and 4-aminocyclohexylC0-2alkyl.

In certain aspects, wherein B is —(CH)—(CH3), E is —(CH)—(CH3), V is —(XR4)- or nothing, and W is substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, and X is independently nitrogen or CH, the compounds have the following general formula (VII):

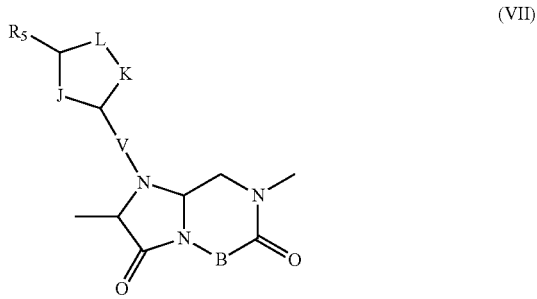

(VII)

wherein K is nitrogen, oxygen, or sulfur, L is nitrogen, oxygen, —(CH)—, or —(CH2)-, J is nitrogen, oxygen, or sulfur, and R5 is independently selected from the group consisting of aminoC2-5alkyl, guanidinoC2-5alkyl, C1-4alkylguanidinoC2-5alkyl, diC1-4alkylguanidino-C2-5alkyl, amidino C2-5alkyl, C1-4alkylamidino C2-5alkyl, diC1-4alkylamidino C2-5alkyl, C1-3alkoxy, Phenyl, substituted phenyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), bis-phenyl methyl, substituted bisphenyl methyl (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyridyl, substituted pyridyl, (where the substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyridylC1-4alkyl, substituted pyridylC1-4alkyl (where the pyridine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), pyrimidylC1-4alkyl, substituted pyrimidylC1-4alkyl (where the pyrimidine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy or nitro, carboxy, cyano, sulfuryl or hydroxyl), triazin-2-yl-C1-4alkyl, substituted triazin-2-yl-C1-4alkyl (where the triazine substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl or hydroxyl), imidazoC1-4alkyl, substituted imidazol C1-4alkyl (where the imidazole substituents are independently selected from one or more of amino, amidino, guanidino, hydrazino, amidrazonyl, C1-4alkylamino, C1-4dialkylamino, halogen, perfluoro C1-4alkyl, C1-4alkyl, C1-3alkoxy, nitro, carboxy, cyano, sulfuryl, hydroxyl, or methyl), imidazolinylC1-4alkyl, N-amidinopiperazinyl-N—C0-4alkyl, hydroxyC2-5alkyl, C1-5alkylaminoC2-5alkyl, hydroxyC2-5alkyl, C1-5alkylaminoC2-5alkyl, C1-5 dialkylaminoC2-5alkyl, N-amidinopiperidinylC1-4alkyl and 4-aminocyclohexylC0-2alkyl.

Additional compounds comprise one selected from the group consisting of Compounds 1-2217 in 2008/0009500. US 2010/0222303. All compound genera, species and conformations thereof of US 2010/0222303, including the exemplary compounds of Tables 3-5 thereof, the claimed compounds, and including the disclosed respective syntheses, are incorporated herein by reference in their entirety as exemplary compounds for use in applicant's presently claimed methods.

Specific exemplary embodiments include a compound having the structure:

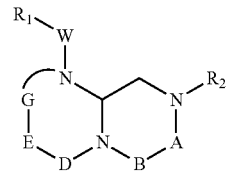

or a pharmaceutically acceptable salt or stereoisomer thereof,
wherein A is —(CHR3)— or —(C=O)—, B is —(CHR4)— or —(C=O)—, D is —(CHR5)— or —(C=O)—, E is —(ZR6)— or —(C=O)—, G is —(XR7)$_n$—, —(CHR7)—(NR8)—, —(C=O)—(XR9)—, or —(C=O)—, W is —Y(C=O)—, —(C=O)NH—, —(SO2)— or is absent, Y is oxygen, sulfur, or —NH—, X and Z is independently nitrogen or CH, n=0 or 1; and R1, R2, R3, R4, R5, R6, R7, R8 and R9 are the same or different and independently selected from an amino acid side chain moiety or derivative thereof, the remainder of the molecule, a linker and a solid support, and stereoisomers thereof, and as defined in US 2010/0222303.

In embodiments wherein A is —(CHR$_3$)— or —(C=O)—; B is —(CHR$_4$)— or —(C=O)—; D is —(CHR$_5$)— or —(C=O)—; E is —ZR$_6$— or —(C=O)—, wherein Z is CH or N; G is —XR$_7$— or —(C=O)—, wherein X is CH or N; W is —(C=O)NH—, —(C=O)O—, —(C=O)S—, —S(O)$_2$— or nothing; and each of R$_1$, R$_2$, R$_3$, R$_4$, R$_5$, R$_6$ and R$_7$ is the same or different and independently an amino acid side chain moiety or an amino acid side chain derivative, the compounds of this invention have the following formula (IA):

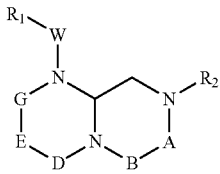
(IA)

wherein specific examples of R$_1$, R$_2$, R$_3$, R$_4$, R$_5$, R$_6$ and R$_7$ are as defined in US 2010/0222303.

In embodiments wherein A is —(CHR$_3$)—, B is —(C=O)—, D is —(CHR$_5$)—, E is —(C=O)—, and G is —(XR$_7$)$_n$—, the compounds of this invention have the following formula (II):

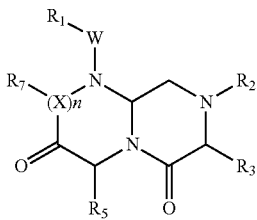
(II)

wherein W, X, Y and n are as defined above, and R$_1$, R$_2$, R$_3$, R$_5$ and R$_7$ are as defined in US 2010/0222303.

In embodiments wherein A is —(C=O)—, B is —(CHR$_4$)—, D is —(C=O)—, E is —(ZR$_6$)—, and G is —(C=O)—(XR$_9$)—, the compounds of this invention have the following formula (III):

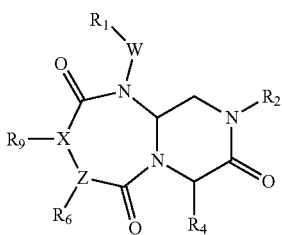
(III)

wherein W, X and Y are as defined above, Z is nitrogen or CH (with the proviso that when Z is CH, then X is nitrogen), and R$_1$, R$_2$, R$_4$, R$_6$ and R$_9$ are as defined in US 2010/0222303.

In embodiments wherein A is —(C=O)—, B is —(CHR$_4$)—, D is —(C=O)—, E is —(ZR$_6$)—, and G is (XR$_7$)$_n$—, the compounds of this invention have the following general formula (IV):

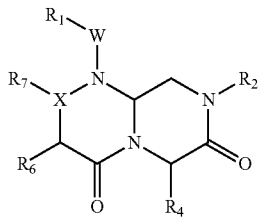
(IV)

wherein W, Y and n are as defined above, Z is nitrogen or CH (when Z is nitrogen, then n is zero, and when Z is CH, then X is nitrogen and n is not zero), and R$_1$, R$_2$, R$_4$, R$_6$ and R$_7$, are as defined in US 2010/0222303.

In embodiments wherein A is —(C=O)—, B is —(CHR$_4$)—, D is —(C=O)—, E is —CHR$_6$—, and G is —XR$_7$—, wherein X is CH or N, and the compound has a structure of Formula (IVA):

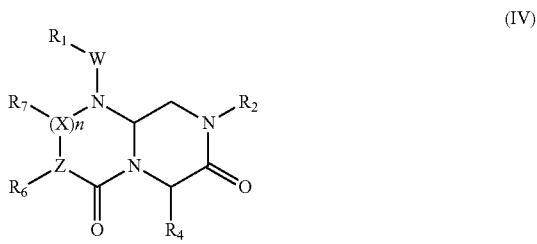
(IVA)

wherein R$_1$, R$_2$, R$_4$, R$_6$ and R$_7$ are as defined in US 2010/0222303.

In an embodiments of compounds of formula (IVA) wherein X is N, the compound has a structure of Formula (IVA$_1$):

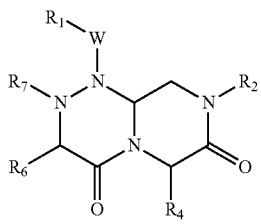
(IVA$_1$)

wherein R$_1$, R$_2$, R$_4$, R$_6$, R$_7$ are as defined in US 2010/0222303.

In certain embodiments, the compounds of this invention have the following general formula (VI):

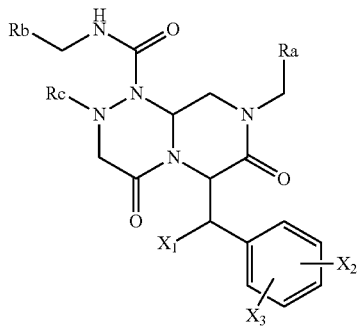

(VI)

wherein $R_a$, $R_b$, and $R_c$ are as defined in US 2010/0222303, and $X_1$, $X_2$, and $X_3$ may be the same or different and independently selected from hydrogen, hydroxyl, and halide.

U.S. Pat. No. 6,413,963. All compound genera, species and conformations thereof of U.S. Pat. No. 6,413,963, including the exemplary compounds of Tables 1-5 thereof, the claimed compounds, and including the disclosed respective syntheses, are incorporated herein by reference in their entireties as exemplary compounds for use in applicant's presently claimed methods.

Specific exemplary embodiments include a compound having formula (I):

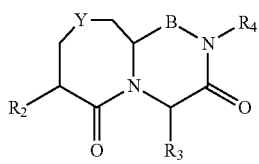

(I)

wherein Y is selected from —CH($R_5$)-A-N($R_1$)—, -A-N($R_1$)—CH(R')—, -A-N($R_1$)—C(=O)—, -A-C(=O)—N($R_1$)—, -A-CH($R_1$)—O—, and -A-CH($R_1$)—N(R')—; A is —(CHR')$_n$—; B is —(CHR")$_m$—; n=0, 1 or 2; m=1, 2 or 3; and any two adjacent CH groups or adjacent NH and CH groups on the bicyclic ring may optionally form a double bond; and wherein R', R", $R_1$, $R_2$, $R_3$, $R_4$ and $R_5$ are as defined in U.S. Pat. No. 6,413,963.

In embodiments wherein Y is —CH($R_5$)-A-N($R_1$)—, the compounds of this invention have the following structure (I'):

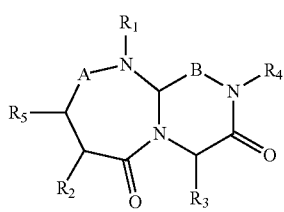

(I')

wherein A and B are as defined above, and $R_1$, $R_2$, $R_3$, $R_4$ and $R_5$ are as defined in U.S. Pat. No. 6,413,963.

In embodiments wherein Y is -A-N($R_1$)—CH(R')—, the compounds of this invention have the following structure (I"):

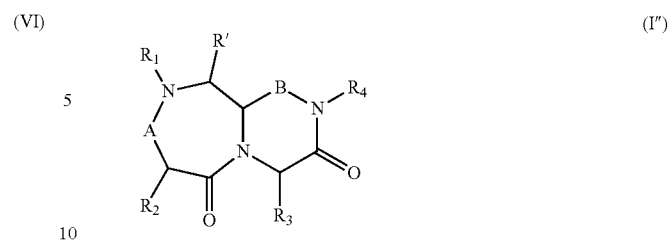

(I")

wherein A and B are as defined above, and R', $R_1$, $R_2$, $R_3$ and $R_4$ are as defined in U.S. Pat. No. 6,413,963.

In embodiments wherein Y is -A-N($R_1$)—C(=O)—, the compounds of this invention have the following structure (I'''):

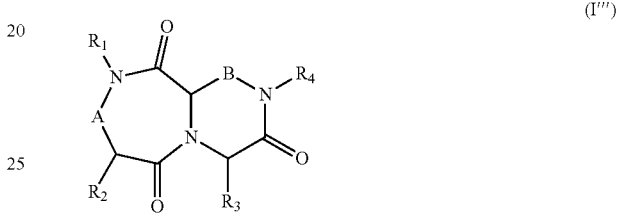

(I''')

wherein A and B are as defined above, and $R_1$, $R_2$, $R_3$ and $R_4$ are as defined in U.S. Pat. No. 6,413,963.

In embodiments wherein Y is -A-C(=O)—N($R_1$)—, the compounds of this invention have the following structure (I''''):

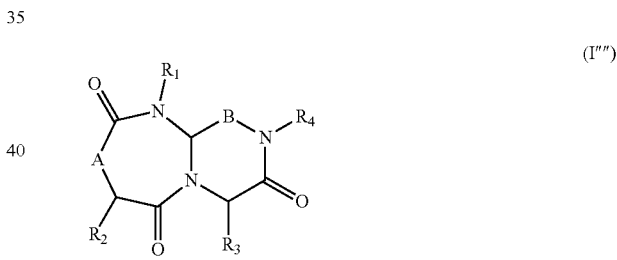

(I'''')

wherein A and B are as defined above, and $R_1$, $R_2$, $R_3$ and $R_4$ are as defined in U.S. Pat. No. 6,413,963.

In embodiments wherein Y is -A-CH($R_1$)—O—, the compounds of this invention have the following structure (I'''''):

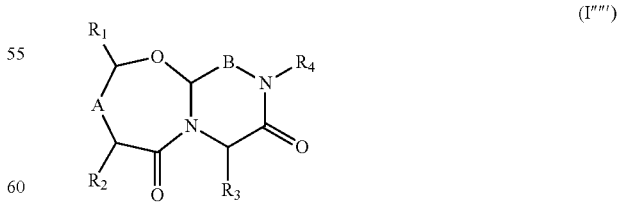

(I''''')

wherein A and B are as defined above, and $R_1$, $R_2$, $R_3$ and $R_4$ are as defined in U.S. Pat. No. 6,413,963.

In embodiments wherein Y is -A-CH($R_1$)—N(R')—, the compounds of this invention have the following structure (I''''''):

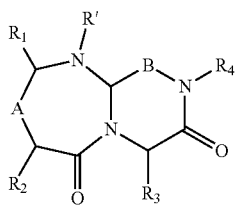

(I''')

wherein A and B are as defined above, and R', $R_1$, $R_2$, $R_3$ and $R_4$ are as defined in U.S. Pat. No. 6,413,963.

U.S. Pat. No. 7,531,320. All compound genera, species and conformations thereof of U.S. Pat. No. 7,531,320, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having formula (I):

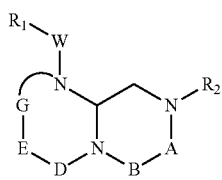

(I)

wherein A is —(CHR$_3$)— or —(C=O)—, B is —(CHR$_4$)— or —(C=O)—, D is —(CHR$_5$)— or —(C=O)—, E is —(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1; and $R_1$, $R_2$, $R_3$, $R_4$, $R_5$, $R_6$, $R_7$, $R_8$ and $R_9$ are the same or different and are each independently selected from an amino acid side chain moiety, a derivative of an amino acid side chain moiety, or the remainder of the molecule, and stereoisomers thereof.

In certain embodiments, $R_1$, $R_2$, $R_3$, $R_4$, $R_5$, $R_6$, $R_7$, $R_8$ and $R_9$ of formula (I) are independently selected from the group consisting of amino$C_{2-5}$ alkyl, guanidino$C_{2-5}$ alkyl, $C_{1-4}$ alkylguanidino$C_{2-5}$ alkyl, di$C_{1-4}$ alkylguanidino-$C_{2-5}$ alkyl, amidino$C_{2-5}$ alkyl, $C_{1-4}$ alkylamidino$C_{2-5}$ alkyl, di$C_{1-4}$ alkylamidino$C_{2-5}$ alkyl, $C_{1-3}$ alkoxy, phenyl, substituted phenyl (where the substituents are independently selected from one or more of amino, amidino, guanidino, hydrazino, amidazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), benzyl, substituted benzyl (where the substituents on the benzyl are independently selected from one or more of amino, amidino, guanidino, hydrazino, amidazonyl, $C_{1-4}$ alkylamino, $C_{1-4}$ dialkylamino, halogen, perfluoro $C_{1-4}$ alkyl, $C_{1-3}$ alkoxy, nitro, carboxy, cyano, sulfuryl or hydroxyl), naphthyl, substituted naphthyl (where the substituents are independently selected from one or more of amino, amidino, guanidino, hydrazino, amidazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), pyridyl, substituted pyridyl, (where the substituents are independently selected from one or more of amino amidino, guanidino, hydrazino, amidazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), pyridyl$C_{1-4}$ alkyl, substituted pyridyl$C_{1-4}$ alkyl (where the pyridine substituents are independently selected from one or more of amino, amidino, guanidino, hydrazino, amidazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), pyrimidyl$C_{1-4}$ alkyl, substituted pyrimidyl$C_{1-4}$ alkyl (where the pyrimidine substituents are independently selected from one or more of amino, amidino, guanidino, hydrazino, amidazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy or nitro, carboxy, cyano, sulfuryl or hydroxyl), triazin-2-yl-$C_{1-4}$ alkyl, substituted triazin-2-yl-$C_{1-4}$ alkyl (where the triazine substituents are independently selected from one or more of amino, amidino, guanidino, hydrazino, amidazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), imidazo$C_{1-4}$ alkyl, substituted imidazol $C_{1-4}$ alkyl (where the imidazole substituents are independently selected from one or more of amino, amidino, guanidino, hydrazino, amidazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), imidazolinyl$C_{1-4}$ alkyl, N-amidinopiperazinyl-N—$C_{0-4}$ alkyl, hydroxy$C_{2-5}$ alkyl, $C_{1-5}$ alkylamino$C_{2-5}$ alkyl, hydroxy$C_{2-5}$ alkyl, $C_{1-5}$ alkylamino$C_{2-5}$ alkyl, $C_{1-5}$ dialkylamino$C_{2-5}$ alkyl, N-amidinopiperidinyl$C_{1-4}$ alkyl and 4-aminocyclohexyl$C_{0-2}$alkyl.

In certain embodiments, A is —(CHR$_3$)—, B is —(C=O)—, D is —(CHR$_5$)—, E is —(C=O)—, G is —(XR$_7$)$_n$—, and the compound has the following general formula (II):

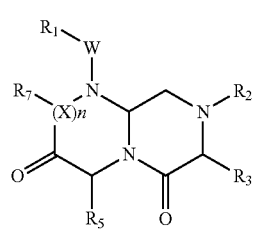

(II)

wherein $R_1$, $R_2$, $R_3$, $R_5$, $R_7$, W, X and n are as defined as in formula (I).

In certain embodiments, A is —(C=O)—, B is —(CHR$_4$)—, D is —(C=O)—, E is —(ZR$_6$)—, G is —(C=O)—(XR$_9$)—, and the compound has the following general formula (III):

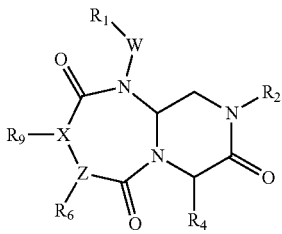

(III)

wherein $R_1$, $R_2$, $R_4$, $R_6$, $R_9$, W and X are as defined in formula (I), Z is nitrogen or CH (when Z is CH, then X is nitrogen).

In certain embodiments, A is —(C=O)—, B is —(CHR$_4$)—, D is —(C=O)—, E is —(ZR$_6$)—, G is (XR$_7$)$_n$—, and the compound has the following general formula (IV):

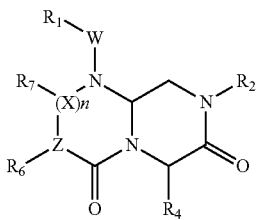

(IV)

wherein $R_1$, $R_2$, $R_4$, $R_6$, $R_7$, W, X and n are as defined in formula (I), and Z is nitrogen or CH, with the proviso that when Z is nitrogen, then n is zero, and when Z is CH, then X is nitrogen and n is not zero.

In certain embodiments, the compound has the following general formula (VI):

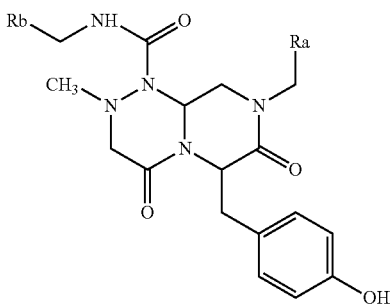

(VI)

wherein, $R_a$ is a bicyclic aryl group having 8 to 11 ring members, which may have 1 to 3 heteroatoms selected from nitrogen, oxygen or sulfur, and $R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy group. Optionally, $R_a$ is naphthyl, quinolinyl or isoquinolinyl group, and $R_b$ is phenyl, pyridyl or piperidyl, all of which may be substituted with one or more substituents selected from a group consisting of halide, hydroxy, cyano, lower alkyl, and lower alkoxy group. In certain embodiments, $R_a$ is naphthyl, and $R_b$ is phenyl, which may be substituted with one or more substituents selected from a group consisting of halide, hydroxy, cyano, lower alkyl, and lower alkoxy group.

In certain embodiments, the compound is selected from COMPOUNDS 1, 3, 4, and 5 as defined in U.S. Pat. No. 6,413,963.

U.S. Pat. No. 7,563,825. All compound genera, species and conformations thereof of U.S. Pat. No. 7,563,825, including the exemplary compounds of Tables 1-5 thereof, the claimed compounds, and including the disclosed respective syntheses, are incorporated herein by reference in their entirety as exemplary compounds for use in applicant's presently claimed methods.

Specific exemplary embodiments include a compound having formula (I):

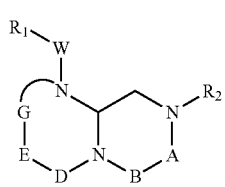

(I)

wherein A is —(C=O)—(CHR$_3$)—, B is —N—R$_4$—, D is —(CHR$_5$)— or —(C=O)—, E is —(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1; and $R_1$, $R_2$, $R_3$, $R_4$, $R_5$, $R_6$, $R_7$, $R_8$ and $R_9$, are the same or different and independently selected from an amino acid side chain moiety or derivative thereof, the remainder of the molecule, a linker and a solid support, and stereoisomers thereof. More specifically, $R_1$, $R_2$, $R_3$, $R_4$, $R_5$, $R_6$, $R_7$, $R_8$ and $R_9$, are independently selected from the group consisting of aminoC$_{2-5}$ alkyl, guanidineC$_{2-5}$ alkyl, C$_{1-4}$ alkylguanidinoC$_{2-5}$ alkyl, diC$_{1-4}$ alkylguanidino-C$_{2-5}$ alkyl, amidinoC$_{2-5}$ alkyl, C$_{1-4}$ alkylamidino C$_{2-5}$ alkyl, diC$_{1-4}$ alkylamidinoC$_{2-5}$ alkyl, C$_{1-3}$ alkoxy, Phenyl, substituted phenyl (where the substituents are independently selected from one or more of amino, amidino, guanidino, hydrazino, amidrazonyl, C$_{1-4}$ alkylamino, C$_{1-4}$ dialkylamino, halogen, perfluoro C$_{1-4}$ alkyl, C$_{1-4}$ alkyl, C$_{1-3}$ alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C$_{1-4}$ alkylamino, C$_{1-4}$ dialkylamino, halogen, perfluoro C$_{1-4}$ alkyl, C$_{1-4}$ alkyl, C$_{1-3}$ alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C$_{1-4}$ alkylamino, C$_{1-4}$ dialkylamino, halogen, perfluoro C$_{1-4}$ alkyl, C$_{1-4}$ alkyl, C$_{1-3}$ alkoxy, nitro, carboxy, cyano, sulfuryl or hydroxyl), bisphenyl methyl, substituted bis-phenyl methyl (where the substituents are independently selected from one or more of amino, amidino, guanidino, hydrazino, amidrazonyl, C$_{1-4}$ alkylamino, C$_{1-4}$ dialkylamino, halogen, perfluoro C$_{1-4}$ alkyl, C$_{1-4}$ alkyl, C$_{1-3}$ alkoxy, nitro, carboxy, cyano, sulfuryl or hydroxyl), pyridyl, substituted pyridyl, (where the substituents are independently selected from one or more of amino, amidino, guanidino, hydrazino, amidrazonyl, C$_{1-4}$ alkylamino, C$_{1-4}$ dialkylamino, halogen, perfluoro C$_{1-4}$ alkyl, C$_{1-4}$ alkyl, C$_{1-3}$ alkoxy, nitro, carboxy, cyano, sulfuryl or hydroxyl), pyridylC$_{1-4}$ alkyl, substituted pyridylC$_{1-4}$ alkyl (where the pyridine substituents are independently selected from one or more of amino, amidino, guanidino, hydrazino, amidrazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), pyrimidyl$C_{1-4}$ alkyl, substituted pyrimidyl$C_{1-4}$ alkyl (where the pyrimidine substituents are independently selected from one or more of amino, amidino, guanidino, hydrazino, amidrazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), triazin-2-yl-$C_{1-4}$ alkyl, substituted triazin-2-yl-$C_{1-4}$ alkyl (where the triazine substituents are independently selected from one or more of amino, amidino, guanidino, hydrazino, amidrazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), imidazo$C_{1-4}$ alkyl, substituted imidazol $C_{1-4}$ alkyl (where the imidazole substituents are independently selected from one or more of amino, amidino, guanidino, hydrazino, amidrazonyl, $C_{1-4}$ alkylamino, $C_{1-4}$ dialkylamino, halogen, perfluoro $C_{1-4}$ alkyl, $C_{1-4}$ alkyl, $C_{1-3}$ alkoxy, nitro, carboxy, cyano, sulfuryl or hydroxyl), imidazolinylCalkyl, N-amidinopiperazinyl-N—$C_{0-4}$ alkyl, hydroxy$C_{2-5}$ alkyl, $C_{1-5}$ alkylamino$C_{2-5}$ alkyl, hydroxy$C_{2-5}$ alkyl, $C_{1-5}$ alkylamino$C_{2-5}$ alkyl, $C_{1-5}$ dialkylamino$C_{2-5}$ alkyl, N-amidinopiperidinyl$C_{1-4}$ alkyl and 4-aminocyclohexyl$C_{0-2}$ alkyl. In one embodiment, $R_1, R_2, R_6$ of E, and $R_7$, $R_8$ and $R_9$ of G are the same or different and represent the remainder of the compound, and $R_3$ or A, $R_4$ of B or $R_5$ of D is selected from an amino acid side chain moiety or derivative thereof. As used herein, the term "remainder of the compound" means any moiety, agent, compound, support, molecule, linker, amino acid, peptide or protein covalently attached to the α-helix mimetic structure at $R_1, R_2, R_5$, $R_6, R_7, R_8$ and/or $R_9$ positions. This term also includes amino acid side chain moieties and derivatives thereof, as defined in U.S. Pat. No. 7,563,825.

In embodiments wherein A is —(C=O)—CHR$_3$—, B is —N—R$_4$, D is —(C=O)—, E is —(ZR$_6$)—, G is —(C=O)—(XR$_9$)—, the α-helix mimetic compounds for use in this invention have the following general formula (III):

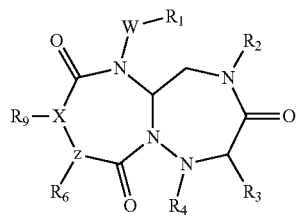

(III)

wherein $R_1, R_2, R_4, R_6, R_9$, W and X are as defined above, Z is nitrogen or CH (when Z is CH, then X is nitrogen). In a preferred embodiment, $R_1, R_2, R_6$, and $R_9$ represent the remainder of the compound, and $R_4$ is selected from an amino acid side chain moiety. In a more specific embodiment wherein A is —O—CHR$_3$—, B is —NR$_4$—, D is —(C=O)—, E is —(ZR$_6$)—, Gi is —(XR$_7$)$_n$—, the α-helix mimetic compounds for use in this invention have the following formula (IV):

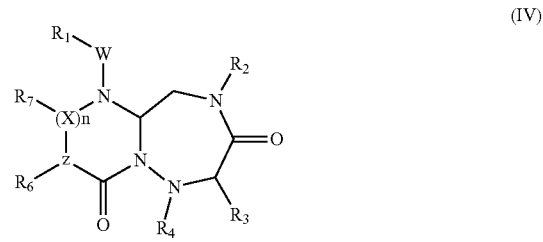

(IV)

wherein $R_1, R_2, R_4, R_6, R_7$, W, X and n are as defined above, and Z is nitrogen or CH (when Z is nitrogen, then n is zero, and when Z is CH, then X is nitrogen and n is not zero). In a preferred embodiment, $R_1, R_2, R_6$, and $R_7$ represent the remainder of the compound, and $R_4$ is selected from an amino acid side chain moiety. In this case, $R_6$ or $R_7$ may be selected from an amino acid side chain moiety when Z and X are CH, respectively.

WO 2010/128685. All compound genera, species and conformations thereof of WO 2010/128685, including the exemplary compounds of Tables thereof, the claimed compounds, and including the disclosed respective syntheses, are incorporated herein by reference in their entirety as exemplary compounds for use in applicant's presently claimed methods.

(1) A compound having the following general formula (I):

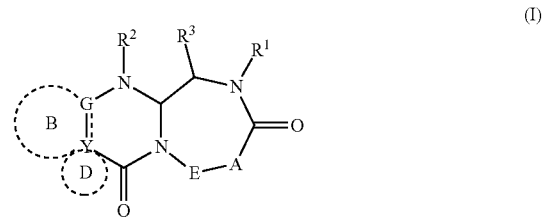

(I)

Wherein ----- is single bond or double bond;
A is —CHR$^7$—,
  wherein
  R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is bond, —CHR$^5$—, —O— or —NR$^8$—,
  wherein
  R$^5$ is hydrogen, optionally substituted alkyl, optionally substituted alkenyl, optionally substituted alkynyl, optionally substituted arylalkyl or optionally substituted heteroarylalkyl; and
  R$^8$ is hydrogen, optionally substituted alkyl, optionally substituted alkenyl or optionally substituted alkynyl;
B is void or optionally substituted monocyclic ring formed together with G and Y;
D is void or optionally substituted spiro ring formed together with Y;
with the proviso that
B and D are not both present;
when B is present, then G and Y are independently carbon atom or nitrogen atom, when D is present, then Y is carbon atom and G is —NR$^6$—, —O—, —CHR$^6$— or —C(R$^6$)$_2$—,
when both B and D are void, then G and Y are the same or different and each is —NR$^6$—, —O—, —CHR$^6$— or —C(R$^6$)$_2$—,
wherein
each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
when E is bond, then D is void, B is optionally substituted monocyclic ring, and G and Y are independently carbon atom or nitrogen atom;
R$^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
R$^2$ is —W$^{21}$—W$^{22}$—Rb—R$^{20}$,
wherein
W$^{21}$ is —(CO)— or —(SO$_2$)—,
W$^{22}$ is bond, —O—, —NH— or optionally substituted lower alkylene,
Rb is bond or optionally substituted alkylene, and
R$^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl;
R$^3$ is hydrogen, optionally substituted alkyl, optionally substituted alkenyl or optionally substituted alkynyl;
with the proviso that
when D is void, E is bond, B is benzene, and R$^2$ is —W$^{21}$—W$^{22}$—Rb—R$^{20}$, wherein W$^{21}$ is —(CO)—, W$^{22}$ is —NH—, and Rb is bond, then R$^{20}$ should not be optionally substituted phenyl;
or a pharmaceutically acceptable salt thereof.

(2) The compound according to (1) mentioned above, wherein, in the formula (I),
D is void, and
B is optionally substituted 3-, 4-, 5-, 6- or 7-membered saturated or unsaturated mono cyclic ring formed together with G and Y.

(3) The compound according to (1) mentioned above, wherein, in the formula (I),
D is void, and
B is optionally substituted 4-, 5-, 6- or 7 membered saturated or unsaturated heterocyclic ring formed together with G and Y and the hetero atom is selected from S, N and O and the number of hetero atoms is an integer of 1-3.

(4) The compound according to (1) mentioned above, wherein, in the formula (I),
D is void;
B is optionally substituted 5- or 6-membered saturated or unsaturated heterocyclic ring formed together with G and Y and the hetero atom is selected from S, N and O and the number of hetero atoms is an integer of 1-3.

(5) The compound according to (1) mentioned above, wherein, in the formula (I),
B is void;
D is optionally substituted spiro ring; and
G is —NR$^{6'}$—, —CHR$^6$—, —C(R$^6$)$_2$— or —O—,
wherein
each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
R$^{6'}$ is optionally substituted cyclic or noncyclic lower alkyl, optionally substituted_aryl, optionally substituted heteroaryl, optionally substituted arylalkyl or optionally substituted heteroarylalkyl.

(6) The compound according to (1) mentioned above, wherein, in the formula (I),
B is void;
D is optionally substituted C$_{3-8}$ cycloalkane; and
G is —NR$^{6'}$—, —CHR$^6$—, —C(R$^6$)$_2$— or —O—,
wherein
each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
R$^{6'}$ is optionally substituted cyclic or noncyclic lower alkyl, optionally substituted_aryl, optionally substituted heteroaryl, optionally substituted arylalkyl or optionally substituted heteroarylalkyl.

(7) The compound according to (1) mentioned above, wherein, in the formula (I), both B and D are void, and at least one of G and Y is —NR$^{6'}$—, —CHR$^6$—, —C(R$^6$)$_2$— or —O—,
wherein
each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
R$^{6'}$ is optionally substituted cyclic or noncyclic lower alkyl, optionally substituted aryl, optionally substituted heteroaryl, optionally substituted arylalkyl or optionally substituted heteroarylalkyl.

(8) The compound according to (1) mentioned above, wherein, in the formula (I), both B and D are void; and
G is —NR$^{6'}$—, —CHR$^{6'}$—, —C(R$^{6'}$)$_2$—, or —O—,
wherein
each R$^{6'}$ is independently optionally substituted cyclic or noncyclic lower alkyl, optionally substituted aryl, optionally substituted heteroaryl, optionally substituted arylalkyl or optionally substituted heteroarylalkyl.

(9) The compound according to (1) mentioned above, wherein, in the formula (I), both B and D are void;
G is —NR$^6$— or —O—,
wherein
R$^{6'}$ is optionally substituted lower alkyl, optionally substituted alkenyl or optionally substituted aryl; and
Y is —CHR$^6$— or —C(R$^6$)$_2$—,
wherein
each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl.

(10) The compound according to (1) mentioned above, wherein, in the formula (I), both B and D are void;

G is —NR$^{6'}$—, or —O—,
wherein
R$^{6'}$ is optionally substituted lower alkyl, or optionally substituted alkenyl; and
Y is —CHR$^6$— or —C(R$^6$)$_2$—,
wherein
R$^6$ is hydrogen, optionally substituted alkyl, optionally substituted alkenyl or optionally substituted alkynyl.

(11) The compound according to (1) mentioned above, wherein, in the formula (I),
E is —CHR$^5$—, —O—, or —NR$^8$—,
wherein
R$^5$ is hydrogen, optionally substituted lower alkyl, optionally substituted lower alkenyl or optionally substituted lower alkynyl, and
R$^8$ is hydrogen, lower alkyl, lower alkenyl or lower alkynyl.

(12) The compound according to (1) mentioned above, wherein, in the formula (I),
E is —CHR$^5$—, —O—, or —NR$^8$—,
wherein
R$^5$ is hydrogen or optionally substituted lower alkyl, and
R$^8$ is hydrogen, lower alkyl, lower alkenyl or lower alkynyl.

(13) The compound according to (1) mentioned above, wherein, in the formula (I),
E is —CHR$^5$—, —O—, or —NR$^8$—,
wherein
R$^5$ is hydrogen, or lower alkyl, and
R$^8$ is hydrogen, lower alkyl, lower alkenyl or lower alkynyl.

(14) The compound according to (1) mentioned above, wherein, in the formula (I),
E is —CHR$^5$—, —O—, or —NR$^8$—,
wherein
R$^5$ is hydrogen, lower alkyl, lower alkenyl or lower alkynyl, and
R$^8$ is hydrogen or alkyl.

(15) The compound according to (1) mentioned above, wherein, in the formula (I),
E is —CHR$^5$—, —O—, or —NR$^8$—,
wherein
R$^5$ is hydrogen or lower alkyl, and
R$^8$ is hydrogen or lower alkyl.

(16) The compound according to (1) mentioned above, wherein, in the formula (I),
E is —O—, or —NR$^8$—,
wherein
R$^8$ is hydrogen or lower alkyl.

(17) The compound according to (1) mentioned above, wherein, in the formula (I),
D is void, B is optionally substituted monocyclic ring and E is bond.

(18) The compound according to (1) mentioned above, wherein, in the formula (I),
R$^3$ is hydrogen or C$_{1-4}$ alkyl group.

(19) The compound according to (1) mentioned above, wherein, in the formula (I),
R$^3$ is hydrogen.

(20) The compound according to (1) mentioned above, wherein, in the formula (I),
D is void; and
B is selected from optionally substituted cyclopropane, optionally substituted cyclobutane, optionally substituted cyclopentane, optionally substituted cyclohexane, optionally substituted cycloheptane, optionally substituted pyrrolidine, optionally substituted pyrazole, optionally substituted cyclopropene, optionally substituted cyclobutene, optionally substituted cyclopentene, optionally substituted cyclohexene, optionally substituted cycloheptene, optionally substituted cyclopentadiene, optionally substituted dihydro-pyrrole, optionally substituted pyrrole, optionally substituted dihydro-pyrazole, optionally substituted imidazole, optionally substituted thiophene, optionally substituted thiazole, optionally substituted isothiazole, optionally substituted thiadiazole, optionally substituted furan, optionally substituted oxazole, optionally substituted isoxazole, optionally substituted oxadiazole, optionally substituted benzene, optionally substituted pyridine, optionally substituted pyridazine, optionally substituted pyrimidine, optionally substituted pyrazine and optionally substituted triazine formed together with G and Y.

(21) The compound according to any one of (1)-(4) and (11)-(20) mentioned above, wherein, in the formula (I),
B is present and is optionally substituted by one or more of the chemical moieties selected from the group consisting of —R$^9$, —OR$^9$, —COR$^9$, —COOR$^9$, —CONR$^9$R$^4$, —NR$^9$R$^4$, —SR$^9$, —SO$_2$R$^9$, —SO$_2$NR$^9$R$^4$, —SO$_3$R$^9$, —NHC(NHR$^9$)NR$^4$, and halogen,
wherein
R$^9$ and R$^4$ are independently selected from hydrogen atom, optionally substituted, cyclic or noncyclic alkyl, aryl, heteroaryl, arylalkyl and hetroarylalkyl.

(22) The compound according to (1) mentioned above, wherein, in the formula (I),
B is void; and
D is optionally substituted cycloalkane.

(23) The compound according to (22) mentioned above, wherein, in the formula (I),
B is void; and
D is optionally substituted C$_{3-8}$ cycloalkane.

(24) The compound according to (22) mentioned above, wherein, in the formula (I),
B is void;
D is optionally substituted C$_{3-6}$ cycloalkane.

(25) The compound according to (1) mentioned above, wherein, in the formula (I),
R$^1$ is —Ra—R$^{10}$,
wherein
Ra is optionally substituted lower alkylene and
R$^{10}$ is hydrogen, optionally substituted alkyl, optionally substituted cycloalkyl, optionally substituted aryl or optionally substituted heteroaryl.

(26) The compound according to (23) mentioned above, wherein, in the formula (I),
R$^1$ is —Ra—R$^{10}$,
wherein
Ra is optionally substituted lower alkylene and
R$^{10}$ is hydrogen, optionally substituted aryl or optionally substituted heteroaryl.

(27) The compound according to (25) mentioned above, wherein, in the formula (I),
R$^{10}$ is hydrogen, optionally substituted methyl, optionally substituted ethyl, optionally substituted propyl, optionally substituted isopropyl, optionally substituted isobutyl, optionally substituted cyclohexyl, optionally substituted benzhydryl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

The compound mentioned above, wherein, in the formula (I), $R^{10}$ is hydrogen, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(29) The compound according to (1) mentioned above, wherein, in the formula (I),
$R^2$ is —$W^{21}$—$W^{22}$—Rb—$R^{20}$;
wherein
$W^{21}$ is —(CO)— or —(SO$_2$)—,
$W^{22}$ is bond, —O—, —NH— or optionally substituted lower alkylene,
Rb is bond or optionally substituted lower alkylene, and
$R^{20}$ is optionally substituted alkyl, optionally substituted cycloalkyl, optionally substituted aryl or optionally substituted heteroaryl.

(30) The compound according to (29) mentioned above, wherein, in the formula (I),
$R^2$ is —$W^{21}$—$W^{22}$—Rb—$R^{20}$;
wherein
$W^{21}$ is —(CO)— or —(SO$_2$)—,
$W^{22}$ is —O— or —NH—,
Rb is bond or optionally substituted lower alkylene, and
$R^{20}$ is optionally substituted alkyl, optionally substituted cycloalkyl, optionally substituted aryl or optionally substituted heteroaryl.

(31) The compound according to (29) and (30) mentioned above, wherein, in the formula (I),
$R^{20}$ is optionally substituted methyl, optionally substituted ethyl, optionally substituted propyl, optionally substituted butyl, optionally substituted isopropyl, optionally substituted isobutyl, optionally substituted cyclohexyl, optionally substituted benzhydryl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl, optionally substituted benzodioxolyl or optionally substituted imidazopyridinyl.

(32) The compound according to (1) mentioned above, wherein, in the formula (I),
$R^7$ of A is -Rc-$R^{70}$,
wherein
Rc is bond or optionally substituted lower alkylene, and
$R^{70}$ is hydrogen, optionally substituted alkyl, optionally substituted aryl or optionally substituted heteroaryl.

(33) The compound according to (32) mentioned above, wherein, in the formula (I),
$R^7$ of A is -Rc-$R^{70}$
wherein
Rc is bond or optionally substituted lower alkylene, and
$R^{70}$ is hydrogen, optionally substituted aryl or optionally substituted heteroaryl.

(34) The compound according to (32) mentioned above, wherein, in the formula (I),
$R^{70}$ is hydrogen, optionally substituted methyl, optionally substituted ethyl, optionally substituted propyl, optionally substituted butyl, optionally substituted isopropyl, optionally substituted isobutyl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(35) The compound according to (33) mentioned above, wherein, in the formula (I), $R^{70}$ is hydrogen, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(36) The compound according to (1) mentioned above, wherein, in the formula (I), D is void;

B is optionally substituted 4-, 5-, 6- or 7 membered saturated or unsaturated heterocyclic ring formed together with G and Y and the hetero atom is selected from S, N and O and the number of hetero atoms is an integer of 1-3;

$R^1$ is —Ra—$R^{10}$,
  wherein
  Ra is optionally substituted lower alkylene and
  $R^{10}$ is Hydrogen, optionally substituted alkyl, optionally substituted cycloalkyl, optionally substituted aryl or optionally substituted heteroaryl;
$R^2$ is —$W^{21}$—$W^{22}$—Rb—$R^{20}$,
  wherein
  $W^{21}$ is —(CO)— or —($SO_2$)—,
  $W^{22}$ is bond, —O—, —NH— or optionally substituted lower alkylene,
  Rb is bond or optionally substituted lower alkylene, and
  $R^{20}$ is optionally substituted alkyl, optionally substituted cycloalkyl, optionally substituted aryl or optionally substituted heteroaryl; and
$R^7$ of A is -Rc-$R^{70}$,
  wherein
  Rc is bond or optionally substituted lower alkylene, and
  $R^{70}$ is hydrogen, optionally substituted alkyl, optionally substituted aryl or optionally substituted heteroaryl.

(37) The compound according to (1) mentioned above, wherein, in the formula (I), B is void;

D is optionally substituted $C_{3-8}$ cycloalkane;

G is —$NR^{6'}$—, —$CHR^{6'}$—, —$C(R^{6'})_2$—, or —O—,
  wherein
  each $R^{6'}$ is independently hydrogen, optionally substituted cyclic or noncyclic lower alkyl, optionally substituted aryl, optionally substituted heteroaryl, optionally substituted arylalkyl or optionally substituted heteroarylalkyl;
$R^1$ is —Ra—$R^{10}$,
  wherein
  Ra is optionally substituted lower alkylene and
  $R^{10}$ is Hydrogen, optionally substituted alkyl, optionally substituted cycloalkyl, optionally substituted aryl or optionally substituted heteroaryl;
$R^2$ is —$W^{21}$—$W^{22}$—Rb—$R^{20}$,
  wherein
  $W^{21}$ is —(CO)— or —($SO_2$)—,
  $W^{22}$ is bond, —O—, —NH— or optionally substituted lower alkylene,
  Rb is bond or optionally substituted lower alkylene, and
  $R^{20}$ is optionally substituted alkyl, optionally substituted cycloalkyl, optionally substituted aryl or optionally substituted heteroaryl; and
$R^7$ of A is -Rc-$R^{70}$,
  wherein
  Rc is bond or optionally substituted lower alkylene, and
  $R^{70}$ is hydrogen, optionally substituted alkyl, optionally substituted aryl or optionally substituted heteroaryl.

(38) The compound according to (1) mentioned above, wherein, in the formula (I), both B and D are void;

G is —$NR^{6'}$—, —$CHR^{6'}$—, —$C(R^{6'})_2$—, or —O—,
  wherein
  each $R^{6'}$ is independently hydrogen, optionally substituted cyclic or noncyclic lower alkyl, optionally substituted aryl, optionally substituted heteroaryl, optionally substituted arylalkyl or optionally substituted heteroarylalkyl;
$R^1$ is —Ra—$R^{10}$,
  wherein
  Ra is optionally substituted lower alkylene and
  $R^{10}$ is hydrogen, optionally substituted alkyl, optionally substituted cycloalkyl, optionally substituted aryl or optionally substituted heteroaryl;
$R^2$ is —$W^{21}$—$W^{22}$—Rb—$R^{20}$,
  wherein
  $W^{21}$ is —(CO)— or —($SO_2$)—,
  $W^{22}$ is bond, —O—, —NH— or optionally substituted lower alkylene,
  Rb is bond or optionally substituted lower alkylene, and
  $R^{20}$ is optionally substituted alkyl, optionally substituted cycloalkyl, optionally substituted aryl or optionally substituted heteroaryl; and
$R^7$ of A is -Rc-$R^{70}$, wherein
Rc is bond or optionally substituted lower alkylene, and
R$^{70}$ is hydrogen, optionally substituted alkyl, optionally substituted aryl or optionally substituted heteroaryl.

(39) The compound according to (1) mentioned above, wherein, in the formula (I),
E is —CHR$^5$—, —O—, or —NR$^8$—,
wherein
R$^5$ is hydrogen or optionally substituted lower alkyl, and
R$^8$ is hydrogen, lower alkyl, lower alkenyl or lower alkynyl;
R$^1$ is —Ra—R$^{10}$,
wherein
Ra is optionally substituted lower alkylene and
R$^{10}$ is hydrogen, optionally substituted alkyl, optionally substituted cycloalkyl, optionally substituted aryl or optionally substituted heteroaryl;
R$^2$ is —W$^{21}$—W$^{22}$—Rb—R20,
wherein
W$^{21}$ is —(CO)— or —(SO$_2$)—,
W$^{22}$ is bond, —O—, —NH— or optionally substituted lower alkylene,
Rb is bond or optionally substituted lower alkylene, and
R$^{20}$ is optionally substituted alkyl, optionally substituted cycloalkyl, optionally substituted aryl or optionally substituted heteroaryl; and
R$^7$ of A is -Rc-R$^{70}$,
wherein
Rc is bond or optionally substituted lower alkylene, and
R$^{70}$ is hydrogen, optionally substituted alkyl, optionally substituted aryl or optionally substituted heteroaryl.

(40) The compound according to (1) mentioned above, wherein, in the formula (I),
D is void and E is bond;
R$^1$ is —Ra—R$^{10}$,
wherein
Ra is optionally substituted lower alkylene and
R$^{10}$ is Hydrogen, optionally substituted alkyl, optionally substituted cycloalkyl, optionally substituted aryl or optionally substituted heteroaryl;
R$^2$ is —W$^{21}$—W$^{22}$—Rb—R$^{20}$,
wherein
W$^{21}$ is —(CO)— or —(SO$_2$)—,
W$^{22}$ is bond, —O—, —NH— or optionally substituted lower alkylene,
Rb is bond or optionally substituted lower alkylene, and
R$^{20}$ is optionally substituted alkyl, optionally substituted cycloalkyl, optionally substituted aryl or optionally substituted heteroaryl; and
R$^7$ of A is -Rc-R$^{70}$,
wherein
Rc is bond or optionally substituted lower alkylene, and
R$^{70}$ is Hydrogen, optionally substituted alkyl, optionally substituted aryl or optionally substituted heteroaryl.

(41) The compound according to (1) mentioned above, wherein, in the formula (I),
both B and D are void;
G is —NR$^{6'}$—, —CHR$^{6'}$—, —C(R$^{6'}$)$_2$—, or —O—,
wherein
each R$^{6'}$ is independently hydrogen, optionally substituted cyclic or noncyclic lower alkyl, optionally substituted aryl, optionally substituted heteroaryl, optionally substituted arylalkyl or optionally substituted heteroarylalkyl; and
E is —CHR$^5$—, —O—, or —NR$^8$—,
wherein
R$^5$ is hydrogen or optionally substituted lower alkyl, and
R$^8$ is hydrogen, lower alkyl, lower alkenyl or lower alkynyl.

(42) The compound according to (1) mentioned above, wherein, in the formula (I),
B is void;
D is optionally substituted C$_{3-8}$ cycloalkane;
G is —NR$^{6'}$—, —CHR$^{6'}$—, —C(R$^{6'}$)$_2$—, or —O—,
wherein
each R$^{6'}$ is independently hydrogen, optionally substituted cyclic or noncyclic lower alkyl, optionally substituted aryl, optionally substituted heteroaryl, optionally substituted arylalkyl or optionally substituted heteroarylalkyl;
E is —CHR$^5$—, —O—, or —NR$^8$—
wherein
R$^5$ is hydrogen or optionally substituted lower alkyl, and
R$^8$ is hydrogen, lower alkyl, lower alkenyl or lower alkynyl;
R$^1$ is —Ra—R$^{10}$,
wherein
Ra is optionally substituted lower alkylene and
R$^{10}$ is hydrogen, optionally substituted alkyl, optionally substituted cycloalkyl, optionally substituted aryl or optionally substituted heteroaryl;
R$^2$ is —W$^{21}$—W$^{22}$—Rb—R$^{20}$;
wherein
W$^{21}$ is —(CO)— or —(SO$_2$)—,
W$^{22}$ is bond, —O—, —NH— or optionally substituted lower alkylene,
Rb is bond or optionally substituted lower alkylene, and
R$^{20}$ is optionally substituted alkyl, optionally substituted cycloalkyl, optionally substituted aryl or optionally substituted heteroaryl; and
R$^7$ of A is -Rc-R$^{70}$,
wherein
Rc is bond or optionally substituted lower alkylene, and
R$^{70}$ is Hydrogen, optionally substituted alkyl, optionally substituted aryl or optionally substituted heteroaryl.

(43) The compound according to (1) mentioned above, wherein, in the formula (I), both B and D are void;
G is —NR$^{6'}$—, —CHR$^{6'}$—, —C(R$^{6'}$)$_2$—, or —O—,
wherein
each R$^{6'}$ is independently hydrogen, optionally substituted cyclic or noncyclic lower alkyl, optionally substituted aryl, optionally substituted heteroaryl, optionally substituted arylalkyl or optionally substituted heteroarylalkyl;
E is —CHR$^5$—, —O—, or —NR$^8$—,
wherein
R$^5$ is hydrogen or optionally substituted lower alkyl, and
R$^8$ is hydrogen, lower alkyl, lower alkenyl or lower alkynyl;
R$^1$ is —Ra—R$^{10}$,
wherein
Ra is optionally substituted lower alkylene and
R$^{10}$ is hydrogen, optionally substituted alkyl, optionally substituted cycloalkyl, optionally substituted aryl or optionally substituted heteroaryl.
R$^2$ is —W$^{21}$—W$^{22}$—Rb—R$^{20}$,
wherein
W$^{21}$ is —(CO)— or —(SO$_2$)—,
W$^{22}$ is bond, —O—, —NH— or optionally substituted lower alkylene,
Rb is bond or optionally substituted lower alkylene, and
R$^{20}$ is optionally substituted alkyl, optionally substituted cycloalkyl, optionally substituted aryl or optionally substituted heteroaryl.

R⁷ of A is -Rc-R⁷⁰,
wherein
Rc is bond or optionally substituted lower alkylene, and
R⁷⁰ is hydrogen, optionally substituted alkyl, optionally substituted aryl or optionally substituted heteroaryl.

In further embodiment of formula (I), such compounds comprise a formula (Ia)

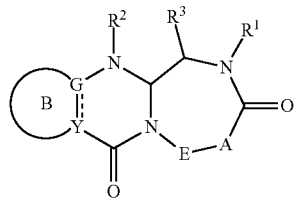

(Ia)

wherein
----- is single bond or double bond;
A is —CHR⁷—,
  wherein
  R⁷ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is —CHR⁵—, —O— or —NR⁸—,
  wherein
  R⁵ is hydrogen, optionally substituted alkyl, optionally substituted alkenyl, optionally substituted alkynyl, optionally substituted arylalkyl or optionally substituted heteroarylalkyl; and
  R⁸ is hydrogen, optionally substituted alkyl, optionally substituted alkenyl or optionally substituted alkynyl;
B is optionally substituted monocyclic ring formed together with G and Y;
G and Y are independently carbon atom or nitrogen atom;
R¹ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
R² is —W²¹—W²²—Rb—R²⁰,
  wherein
  W²¹ is —(CO)— or —(SO₂)—,
  W²² is bond, —O—, —NH— or optionally substituted lower alkylene,
  Rb is bond or optionally substituted alkylene, and
  R²⁰ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and
R³ is hydrogen, optionally substituted alkyl, optionally substituted alkenyl or optionally substituted alkynyl.

In further another embodiment of formula (I), such compounds comprise a formula (Ib)

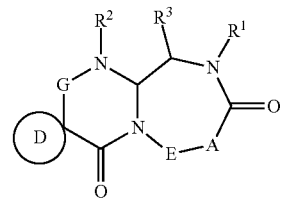

(Ib)

Wherein A is —CHR⁷—,
  wherein
  R⁷ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is —CHR⁵—, —O— or —NR⁸—,
  wherein
  R⁵ is hydrogen, optionally substituted alkyl, optionally substituted alkenyl, optionally substituted alkynyl, optionally substituted arylalkyl or optionally substituted heteroarylalkyl; and
  R⁸ is hydrogen, optionally substituted alkyl, optionally substituted alkenyl or optionally substituted alkynyl;
D is optionally substituted spiro ring,
G is —NR⁶—, —O—, —CHR⁶— or —C(R⁶)₂—,
  wherein
  each R⁶ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl;
R¹ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
R² is —W²¹—W²²—Rb—R²⁰,
  wherein
  W²¹ is —(CO)— or —(SO₂)—,
  W²² is bond, —O—, —NH— or optionally substituted lower alkylene,
  Rb is bond or optionally substituted alkylene, and
  R²⁰ is optionally substituted alkyl, optionally substituted alkenyl, optionally substituted alkynyl, optionally substituted aryl, optionally substituted heteroaryl, optionally substituted cycloalkyl or optionally substituted heterocycloalkyl;
R³ is hydrogen, optionally substituted alkyl, optionally substituted alkenyl or optionally substituted alkynyl.

In further another embodiment of formula (I), such compounds comprise a formula (Ic)

(Ic)

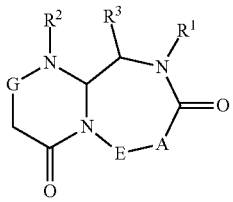

Wherein A is —CHR⁷—,
wherein
R⁷ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is —CHR⁵—, —O— or —NR⁸—,
wherein
R⁵ is hydrogen, optionally substituted alkyl, optionally substituted alkenyl, optionally substituted alkynyl, optionally substituted arylalkyl or optionally substituted heteroarylalkyl, and
R⁸ is hydrogen, optionally substituted alkyl, optionally substituted alkenyl or optionally substituted alkynyl;
G is —NR⁶—, —O—, —CHR⁶— or —C(R⁶)₂—,
wherein
each R⁶ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl;
R¹ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
R² is —W²¹—W²²—Rb—R²⁰,
wherein
W²¹ is —(CO)— or —(SO₂)—,
W²² is bond, —O—, —NH— or optionally substituted lower alkylene,
Rb is bond or optionally substituted alkylene,
R²⁰ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and
R³ is hydrogen or optionally substituted alkyl.

In further another embodiment of formula (I), such compounds comprise a formula (Id)

(Id)

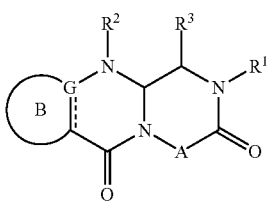

Wherein ≈≈≈ is single bond or double bond;
A is —CHR⁷—,
wherein
R⁷ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
B is optionally substituted monocyclic ring;
G is carbon atom or nitrogen atom;
R¹ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
R² is —W²¹—W²²—Rb—R²⁰,
wherein
W²¹ is —(CO)— or —(SO₂)—,
W²² is bond, —O—, —NH— or optionally substituted lower alkylene,
Rb is bond or optionally substituted alkylene, and
R²⁰ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and
R³ is hydrogen, optionally substituted alkyl, optionally substituted alkenyl or optionally substituted alkynyl;
with the proviso that
when B is benzene, and R² is —W²¹—W²²—Rb—R²⁰; wherein W²¹ is —(CO)—; W²² is —NH—; Rb is bond, then R²⁰ should not be optionally substituted phenyl.
WO 2010/044485. All compound genera, species and conformations thereof of WO 2010/044485, including the exemplary compounds of Tables thereof, the claimed compounds, and including the disclosed respective syntheses, are incorporated herein by reference in their entirety as exemplary compounds for use in applicant's presently claimed methods.
(1) A compound having the following general formula (I):

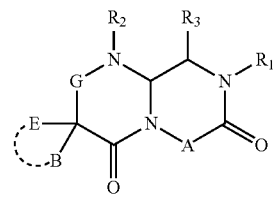

wherein A is —(CHR⁷)—;
wherein
R⁷ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl, or optionally substituted heterocycloalkylalkyl;
B and E are the same or different and independently selected from hydrogen, optionally substituted alkyl, optionally substituted alkenyl, and optionally substituted alkynyl or form an optionally substituted spiro ring indicated by dashed lines;
G is —NH—, —NR$^6$—, —O—, —CH$_2$—, —CHR$^6$— or —C(R$^6$)$_2$—;
wherein
each R$^6$ is the same or different and independently selected from optionally substituted alkyl, optionally substituted alkenyl, and optionally substituted alkynyl;
R$^1$ is optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl;
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl; and
R$^3$ is hydrogen, optionally substituted alkyl, optionally substituted alkenyl, or optionally substituted alkynyl;
with the proviso that
1) when Rb is optionally substituted lower alkylene, then W$^{22}$ should be —O— or —NH—,
2) when E and B are hydrogen, then R$^3$ should be hydrogen,
3) when G is —NH—, —CH$_2$—, —CHR$^6$— or —NR$^6$—, then B and E should not be hydrogen, and
4) when G is —O—, B and E are hydrogen and R$^3$ is hydrogen, then R$^1$ should not be 8-quinolylmethyl;
or a pharmaceutically acceptable salt thereof (2) The compound according to (1) mentioned above, wherein, in the formula (I),
B and E are the same or different and independently selected from hydrogen, optionally substituted alkyl, optionally substituted alkenyl, and optionally substituted alkynyl or form an optionally substituted 3-, 4-, 5-, 6- or 7 membered unsaturated monocyclic ring, when the formed spiro ring is heterocyclic ring, the hetero atom is selected from S, N and O and a number of hetero atom is 1.

(3) The compound according to (1) mentioned above, wherein, in the formula (I),
B and E are the same or different and independently selected from hydrogen, and optionally substituted alkyl or form an optionally substituted 3-, 4-, 5-, 6- or 7 membered unsaturated monocyclic ring, when the formed spiro ring is heterocyclic ring, the hetero atom is selected from S, N and O and a number of hetero atom is 1.

(4) The compound according to (1) mentioned above, wherein, in the formula (I),
G is —NR$^6$—, —O—, —CH$_2$— or —C(R$^6$)$_2$—;
wherein
each R$^6$ is the same or different and independently selected from optionally substituted alkyl, optionally substituted alkenyl, and optionally substituted alkynyl.

(5) The compound according to (1) mentioned above, wherein, in the formula (I),
G is —O—.

(6) The compound according to (1) mentioned above, wherein, in the formula (I),
G is —O—, and
B and E are hydrogen.

(7) The compound according to (1) mentioned above, wherein, in the formula (I),
R$^3$ is hydrogen.

(8) The compound according to (1) mentioned above, wherein, in the formula (I),
A is —(CHR$^7$)—;
wherein
R$^7$ is optionally substituted alkyl, optionally substituted aryl, or optionally substituted arylalkyl.

(9) The compound according to (1) mentioned above, wherein, in the formula (I),
R$^1$ is optionally substituted alkyl, optionally substituted arylalkyl, optionally substituted heteroarylalkyl, or optionally substituted cycloalkylalkyl.

(10) The compound according to (1) mentioned above, wherein, in the formula (I),
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted aryl, or optionally substituted heteroaryl.

(11) The compound according to (1) mentioned above, wherein, in the formula (I),
A is —(CHR$^7$)—;
wherein
R$^7$ is optionally substituted alkyl, or optionally substituted arylalkyl; and
R$^1$ is optionally substituted alkyl, optionally substituted arylalkyl, optionally substituted heteroarylalkyl, or optionally substituted cycloalkylalkyl; and
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted aryl, optionally substituted heteroaryl.

(12) The compound according to (1) mentioned above, wherein, in the formula (I),
R$^1$ is —Ra—R$^{10}$;
wherein
Ra is optionally substituted lower alkylene and
R$^{10}$ is optionally substituted aryl or optionally substituted heteroaryl.

(13) The compound according to (12) mentioned above, wherein, in the formula (I),
R$^{10}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(14) The compound according to (1) mentioned above, wherein, in the formula (I),
$R^2$ is $—W^{21}—W^{22}—Rb—R^{20}$;
wherein
$W^{21}$ is $—(CO)—$ or $—(SO_2)—$;
$W^{22}$ is bond, $—O—$, $—NH—$ or optionally substituted lower alkylene;
Rb is bond or optionally substituted lower alkylene; and
$R^{20}$ is optionally substituted aryl or optionally substituted heteroaryl.

(15) The compound according to (14) mentioned above, wherein, in the formula (I),
$R^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(16) The compound according to (1) mentioned above, wherein, in the formula (I),
$R^3$ is selected from hydrogen and $C_{1-4}$ lower alkyl group.

(17) The compound according to (1) mentioned above, wherein, in the formula (I),
$R^7$ of A is -Rc-$R^{70}$
wherein
Rc is bond or optionally substituted lower alkylene, and
$R^{70}$ is optionally substituted aryl or optionally substituted heteroaryl.

(18) The compound according to (17) mentioned above, wherein, in the formula (I),
$R^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(19) The compound according to (2) mentioned above, in which, in the formula (I),
$R^1$ is $—Ra—R^{10}$;
wherein
Ra is optionally substituted lower alkylene, and
$R^{10}$ is optionally substituted aryl, or optionally substituted heteroaryl, and
$R^3$ is selected from hydrogen and $C_{1-4}$ lower alkyl group.

(20) The compound according to (2) mentioned above, wherein, in the formula (I),
$R^2$ is $—W^{21}—W^{22}—Rb—R^{20}$;
wherein
$W^{21}$ is $—(CO)—$ or $—(SO_2)—$;
$W^{22}$ is bond, $—O—$, $—NH—$ or optionally substituted lower alkylene;
Rb is bond or optionally substituted lower alkylene; and
$R^{20}$ is optionally substituted aryl or optionally substituted heteroaryl; and
$R^3$ is selected from hydrogen and $C_{1-4}$ lower alkyl group.

(21) The compound according to (2) mentioned above, wherein, in the formula (I),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(22) The compound according to (2) mentioned above, wherein, in the formula (I),
G is $—NR^6—$, $—O—$, $—CH_2—$ or $—C(R^6)_2—$;
wherein
each $R^6$ is the same or different and independently selected from optionally substituted alkyl, optionally substituted alkenyl, and optionally substituted alkynyl; and
$R^3$ is selected from hydrogen and $C_{1-4}$ lower alkyl group.

(23) The compound according to (2) mentioned above, wherein, in the formula (I),
G is $—NR^6—$, $—O—$, $—CH_2—$ or $—C(R^6)_2—$;
wherein
each $R^6$ is the same or different and independently selected from optionally substituted alkyl, optionally substituted alkenyl, and optionally substituted alkynyl; and
$R^3$ is hydrogen.

(24) The compound according to (3) mentioned above, wherein, in the formula (I),
$R^1$ is —Ra—$R^{10}$;
wherein
Ra is optionally substituted lower alkylene, and
$R^{10}$ is optionally substituted allyl and
$R^3$ is selected from hydrogen and $C_{1-4}$ lower alkyl group.

(25) The compound according to (3) mentioned above, wherein, in the formula (I),
$R^2$ is —$W^{21}$—$W^{22}$—Rb—$R^{20}$;
wherein
$W^{21}$ is —(CO)— or —(SO$_2$)—;
$W^{22}$ is bond, —O—, —NH— or optionally substituted lower alkylene;
Rb is bond or optionally substituted lower alkylene; and
$R^{20}$ is optionally substituted aryl or optionally substituted heteroaryl, and
$R^3$ is selected from hydrogen and $C_{1-4}$ lower alkyl group.

(26) The compound according to (3) mentioned above, wherein, in the formula (I),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(27) The compound according to (3) mentioned above, wherein, in the formula (I),
G is —$NR^6$—, —O—, —$CH_2$— or —$C(R^6)_2$—;
wherein
each $R^6$ is the same or different and independently selected from optionally substituted alkyl, optionally substituted alkenyl, and optionally substituted alkynyl; and
$R^3$ is selected from hydrogen and $C_{1-4}$ lower alkyl group.

(28) The compound according to (3) mentioned above, wherein, in the formula (I),
G is —$NR^6$—, —O—, —$CH_2$— or —$C(R^6)_2$—;
wherein
each $R^6$ is the same or different and independently selected from optionally substituted alkyl, optionally substituted alkenyl, and optionally substituted alkynyl; and
$R^3$ is hydrogen.

(29) The compound according to (5) mentioned above, wherein, in the formula (I),
$R^1$ is —Ra—$R^{10}$;
wherein
Ra is optionally substituted lower alkylene, and
$R^{10}$ is optionally substituted allyl and
$R^3$ is selected from hydrogen or $C_{1-4}$ lower alkyl group.

(30) The compound according to (5) mentioned above, wherein, in the formula (I),
$R^2$ is —$W^{21}$—$W^{22}$—Rb—$R^{20}$;
wherein
$W^{21}$ is —(CO)— or —(SO$_2$)—;
$W^{22}$ is bond, —O—, —NH— or optionally substituted lower alkylene;
Rb is bond or optionally substituted lower alkylene; and
$R^{20}$ is optionally substituted aryl or optionally substituted heteroaryl, and
$R^3$ is selected from hydrogen and $C_{1-4}$ lower alkyl group.

(31) The compound according to (5) mentioned above, wherein, in the formula (I),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(32) The compound according to (5) mentioned above, wherein, in the formula (I),
$R^3$ is hydrogen.

(33) The compound according to (6) mentioned above, wherein, in the formula (I),
$R^1$ is —Ra—$R^{10}$;
wherein
Ra is optionally substituted lower alkylene, and
$R^{10}$ is optionally substituted allyl and
$R^3$ is selected from hydrogen and $C_{1-4}$ lower alkyl group.

(34) The compound according to (6) mentioned above, wherein, in the formula (I),
$R^2$ is —$W^{21}$—$W^{22}$—Rb—$R^{20}$;
wherein
$W^{21}$ is —(CO)— or —(SO$_2$)—;
$W^{22}$ is bond, —O—, —NH— or optionally substituted lower alkylene;
Rb is bond or optionally substituted lower alkylene; and
$R^{20}$ is optionally substituted aryl or optionally substituted heteroaryl, and
$R^3$ is selected from hydrogen and $C_{1-4}$ lower alkyl group.

(35) The compound according to (6) mentioned above, wherein, in the formula (I),
$R^7$ of A is -Rc-$R^{70}$
wherein
Rc is bond or optionally substituted lower alkylene, and
$R^{70}$ is 1 optionally substituted aryl or optionally substituted heteroaryl; and
$R^3$ is selected from hydrogen and $C_{1-4}$ lower alkyl group.

(36) The compound according to (6) mentioned above, wherein, in the formula (I),
$R^3$ is hydrogen.

(37) The compound according to any of (2), (3) and (5) mentioned above, wherein, in the formula (I),
$R^1$ is —Ra—$R^{10}$;
wherein
Ra is optionally substituted lower alkylene, and
$R^{10}$ is optionally substituted aryl, or optionally substituted heteroaryl,
$R^2$ is —$W^{21}$—$W^{22}$—Rb—$R^{20}$;
wherein
$W^{21}$ is —(CO)— or —(SO$_2$)—;
$W^{22}$ is bond, —O—, —NH— or optionally substituted lower alkylene;
Rb is bond or optionally substituted lower alkylene;
$R^{20}$ is optionally substituted aryl or optionally substituted heteroaryl;
$R^3$ is selected from hydrogen and $C_{1-4}$ lower alkyl group;
$R^7$ of A is -Rc-$R^{70}$
wherein
Rc is bond or optionally substituted lower alkylene, and
$R^{70}$ is optionally substituted aryl or optionally substituted heteroaryl.

(38) The compound according to any of (2), (3) mentioned above, wherein, in the formula (I),
G is —NR$^6$—, —O—, —CH$_2$— or —C(R$^6$)$_2$—;
wherein
each R$^6$ is the same or different and independently selected from optionally substituted alkyl, optionally substituted alkenyl, and optionally substituted alkynyl;
R$^1$ is —Ra—R$^{10}$;
wherein
Ra is optionally substituted lower alkylene, and
R$^{10}$ is optionally substituted aryl, or optionally substituted heteroaryl,
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted aryl or optionally substituted heteroaryl;
R$^3$ is hydrogen; and
R$^7$ of A is -Rc-R$^{70}$
wherein
Rc is bond or optionally substituted lower alkylene, and
R$^{70}$ is optionally substituted aryl or optionally substituted heteroaryl.

(39) The compound according to any of (19), (24) and (38) mentioned above, wherein, in the formula (I),
R$^{10}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(40) The compound according to any of (20), (25) and (38) mentioned above, in which, in the formula (I),
R$^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(41) The compound according to any of (21), (26) and (38) mentioned above, in which, in the formula (I),
R$^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(42) The compound according to any of (37) and (38) mentioned above, in which, in the formula (I),
R$^{10}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl;

$R^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl; and $R^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

Further Exemplary Compounds

In particular exemplary aspects, the CBP/β-catenin antagonists (e.g., of TABLE 1) comprises ICG-001, and salts (e.g., physiologically acceptable salts) and derivatives thereof having hair growth stimulating activity.

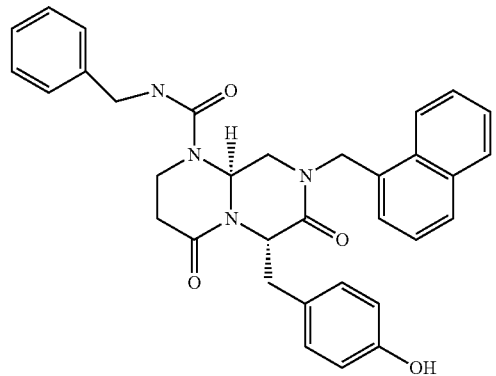

ICG-001

In particular aspects the useful CBP/β-catenin antagonists (e.g., of TABLE 1) comprise a fatty acid group esterified to a hydroxy benzyl group (e.g., lauryl ester), for example, in analogy with the following exemplary preferred compound genus:

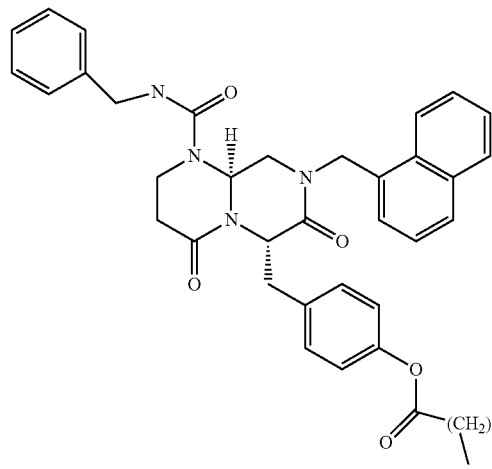

In particular aspects, the fatty acid ester is one derived from one of the fatty acids of Table 2.

In preferred aspects, the esters of the compounds of TABLE 1, comprise the lauryl ester (e.g., the lauric acid ester of ICG-001 (laura-8)):

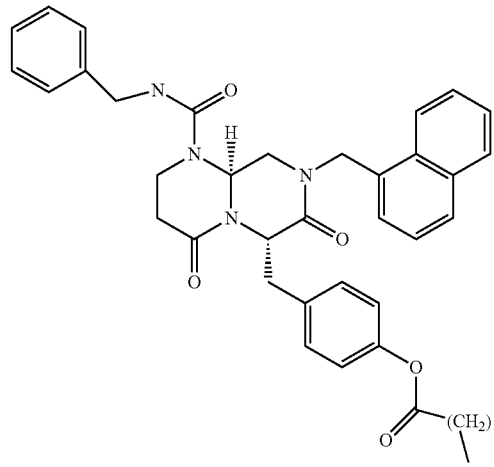

Laura8

In particular aspects, alkyl derivatives of the useful CBP/β-catenin antagonists of TABLE 1 are used, such as:

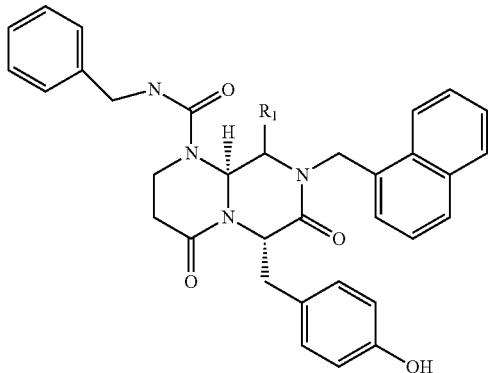

wherein $R_1$ is selected from C1-C6alkyl, wherein the adjoining moiety (here an exemplary bicyclic moiety) on the ring can be any of the substitutions at this position exemplified by the compounds of TABLE 1. In preferred aspects $R_1$ is —$CH_3$. In particular aspects, $R_1$ has the following conformation:

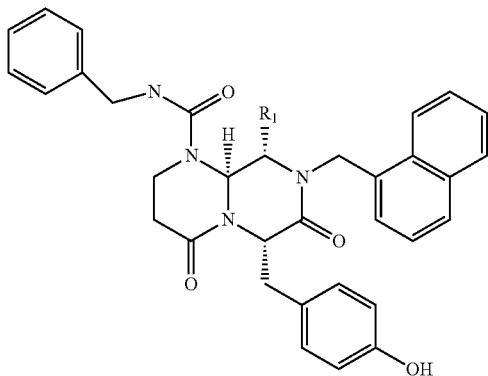

In particular aspects, the alkyl derivative of the useful CBP/β-catenin antagonists of TABLE 1 comprise a fatty acid (e.g., lauryl ester) group esterified to, for example a hydroxy benzyl group, such as in the exemplary compound below:

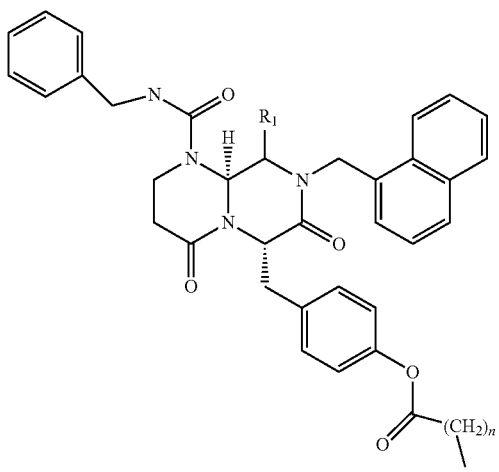

wherein $R_1$ is selected from C1-C6 alkyl. In preferred aspects $R_1$ is —$CH_3$. In particular aspects, $R_1$ has the following conformation:

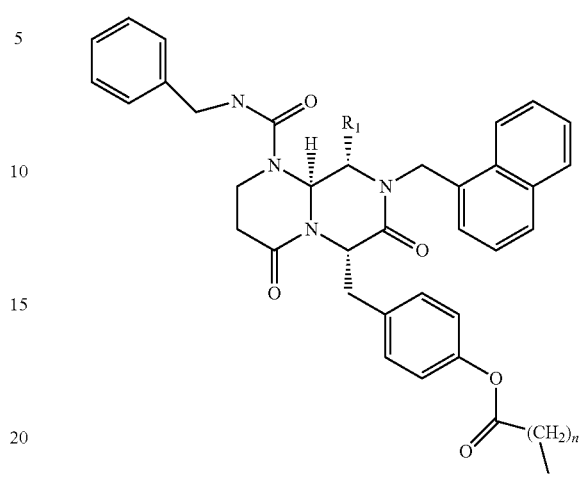

In particular aspects, the fatty acid ester is one derived from one of the fatty acids of Table 2. In preferred aspects, the lauryl ester is used.

TABLE 2

Examples of Saturated Fatty Acids

| Common name | Chemical structure | C:D |
|---|---|---|
| Acetic acid | $CH_3COOH$ | 2:0 |
| Propionic acid | $CH_3CH_2COOH$ | 3:0 |
| Butyric acid | $CH_3(CH_2)_2COOH$ | 4:0 |
| Valeric acid | $CH_3(CH_2)_3COOH$ | 5:0 |
| Caproic acid | $CH_3(CH_2)_4COOH$ | 6:0 |
| Enanthic acid | $CH_3(CH_2)_5COOH$ | 7:0 |
| Caprylic acid | $CH_3(CH_2)_6COOH$ | 8:0 |
| Pelargonic acid | $CH_3(CH_2)_7COOH$ | 9:0 |
| Capric acid | $CH_3(CH_2)_8COOH$ | 10:0 |
| Undecylic acid | $CH_3(CH_2)_9COOH$ | 11:0 |
| Lauric acid | $CH_3(CH_2)_{10}COOH$ | 12:0 |
| Tridecylic acid | $CH_3(CH_2)_{11}COOH$ | 13:0 |
| Myristic acid | $CH_3(CH_2)_{12}COOH$ | 14:0 |
| Pentadecylic acid | $CH_3(CH_2)_{13}COOH$ | 15:0 |
| Palmitic acid | $CH_3(CH_2)_{14}COOH$ | 16:0 |
| Margaric acid | $CH_3(CH_2)_{15}COOH$ | 17:0 |
| Stearic acid | $CH_3(CH_2)_{16}COOH$ | 18:0 |
| Nonadecylic acid | $CH_3(CH_2)_{17}COOH$ | 19:0 |
| Arachidic acid | $CH_3(CH_2)_{18}COOH$ | 20:0 |
| Heneicosylic acid | $CH_3(CH_2)_{19}COOH$ | 21:0 |
| Behenic acid | $CH_3(CH_2)_{20}COOH$ | 22:0 |
| Tricosylic acid | $CH_3(CH_2)_{21}COOH$ | 23:0 |
| Lignoceric acid | $CH_3(CH_2)_{22}COOH$ | 24:0 |
| Pentacosylic acid | $CH_3(CH_2)_{23}COOH$ | 25:0 |
| Cerotic acid | $CH_3(CH_2)_{24}COOH$ | 26:0 |
| Heptacosylic acid | $CH_3(CH_2)_{25}COOH$ | 27:0 |
| Montanic acid | $CH_3(CH_2)_{26}COOH$ | 28:0 |
| Nonacosylic acid | $CH_3(CH_2)_{27}COOH$ | 29:0 |
| Melissic acid | $CH_3(CH_2)_{28}COOH$ | 30:0 |
| Hentriacontylic acid | $CH_3(CH_2)_{29}COOH$ | 31:0 |
| Lacceroic acid | $CH_3(CH_2)_{30}COOH$ | 32:0 |
| Psyllic acid | $CH3(CH_2)_{31}COOH$ | 33:0 |
| Geddic acid | $CH3(CH_2)_{32}COOH$ | 34:0 |
| Ceroplastic acid | $CH3(CH_2)_{33}COOH$ | 35:0 |
| Hexatriacontylic acid | $CH3(CH_2)_{34}COOH$ | 36:0 |

Prodrugs

The present invention is also related to prodrugs using the libraries containing one or more compounds of formula (I). A prodrug is typically designed to release the active drug in the body during or after absorption by enzymatic and/or chemical hydrolysis. The prodrug approach is an effective means of improving the topical, oral, etc., bioavailability or i.v. administration of poorly water-soluble drugs by chemical derivatization to more water-soluble compounds. The most commonly used prodrug approach for increasing aqueous solubility of drugs containing a hydroxyl group is to produce esters containing an ionizable group; e.g., phosphate group, carboxylate group, alkylamino group (Fleisher et al., *Advanced Drug Delivery Reviews*, 115-130, 1996; Davis et al., *Cancer Res.*, 7247-7253, 2002, Golik et al., *Bioorg. Med. Chem. Lett.*, 1837-1842, 1996).

In certain embodiments of the compounds of this invention, the prodrugs of the present invention are capable of serving as a substrate for a phosphatase, a carboxylase, or another enzyme Screening Assays for Compounds Having Utility for the Present Invention According to additional aspects of the present invention, high-throughput assays are available to enable routine facile screening of compound libraries for compounds having utility for the present invention.

Inhibitors of the β-catenin:CBP interaction. As an initial matter, various methods for identifying small molecule inhibitors of the β-catenin:CBP interaction are well described in the art and are, for example, discussed in detail in the patents and patent applications listed in Table 1, herein, and thus will not be repeated here.

Primary screens for compounds affecting asymmetric versus symmetric division in stem cells. In vitro. Based on work that epidermal stem cells are heterogeneous in their capacity to be activated based on the status of their molecular circadian clock, an assay for screening activators of asymmetric division of this stem cell pool is utilized to identify compounds having utility for the present invention. More specifically, (Janisch P. et al. Nature 2011) demonstrated that the population of CD34 expressing bulge stem cells that express high levels of the genes Per 1/2 are more likely to respond to activation and stimuli that remove them from dormancy. The transcription factor BMAL1, a member of the ARNt family of transcription factors in conjunction with its molecular partner clock drive the expression of a core of circadian genes including Per1 and Per2. Mice deficient in BMAL1 exhibit an early aging phenotype including premature aging of the skin.

Accordingly, a high throughput screen to select compounds that induce asymmetric division of epidermal stem cells, is provided by human keratinocytes transfected with a Per/luciferase reporter gene. Keratinocytes, that have been stably transfected with the human Per/luc promoter are grown in vitro, and then plated in either 96 or 384 well plates and screened with a chemical compound collection for compounds that increase luciferase expression. After treatment with compounds for 24 h, the cells will be lysed and treated with luciferase substrate and then read for luciferase activity on a high throughput plate reader (example HP Topcount). Promising compounds can be secondarily screened (e.g., see below).

Secondary screens for compounds affecting asymmetric versus symmetric division in stem cells. Ex Vivo (human skin assay). Culture conditions and assay based on Varani J et al Experimental and Molecular Pathology, 2004.

According to further aspects, human skin (e.g., surgical waste from plastic surgery procedures) is obtained, and the subcutaneous layer of fat trimmed manually (e.g., with a scalpel). The skin is then cut into small fragments about 2 mm square and placed in 6 well plates. 1 ml of keratinocyte culture medium (Gibco 10724-011) with 1% P/S is added to each well. The epidermis, bathed in media is placed facing up. On the next day (overnight culture in the media above), the skin fragments are transferred to fresh wells that respectively contain the compounds to be tested. Approximately 24 hrs and 48 hrs skin samples in culture are removed for RNA isolation and qRT-PCR analysis of genes of interest (e.g., Per 1, 2). Some skin fragments are transferred to wells with new medium every second day (and continued to be treated with compounds. Approximately 7 days after culturing ex vivo, Brdu, 20 uM final concentration per well is added to evaluate proliferation. On approximately the 9th day of culturing the skin ex vivo, the skin fragments are harvested for histology, immunohistochemistry (e.g., staining for Per 1, 2) and BrdU staining to evaluate proliferation. Promising compounds can be subjected to tertiary screens (e.g., see below).

Tertiary screens for compounds affecting asymmetric versus symmetric division in stem cells. In Vivo. Asymmetric cell divisions are important regulators of the stem cell niche. During this process, evolutionarily conserved sets of proteins (e.g., form *C. elegans* and *Drosophila* to humans) are asymmetrically distributed to daughter cells during mitosis. These include proteins of the Par complex e.g. Par3 in mammals (Bazooka in *Drosophila*), Par 6 and atypical Protein Kinase C (aPKC) as well as transcriptional regulators (e.g., numb, a negative regulator of Notch signaling). This process is also important in the control of asymmetric division in the epidermal stem cells niche (Williams, S. et al. Nature 2011). According to particular aspects, therefore, in vivo assays can be to examine asymmetric distribution of these proteins during mitosis in the epidermal stem cell niche.

For example, Bultje et al. (Bultje R Neuron 63, 189-202, 2009) describe an assay to measure asymmetric distributions in the ventricular zone (vz) to evaluate asymmetric divisions during neurogenesis. Essentially this involves treating the animal (either adult or in utero) for a set period of time with compounds (either p.o., s.c., i.v. or topically) with compounds and then sacrificing the animal and examining the Par3 distribution (e.g., via immunohistochemistry) in mitotic cells vs. DNA distribution (e.g., using DAPI staining) Par3 distributes equally among the two daughter cells during symmetric division and unequally (essentially all in one daughter cell) during asymmetric differentiation. Applicant has utilized this assay to show that after topical or oral administration to pregnant mice, that the CBP/catenin antagonist ICG-001 does not affect the number of asymmetric divisions compared to vehicle control. However, the p300/catenin antagonist IQ-1, that increases CBP/catenin signaling at the expense of p300/catenin signaling decreases the number of asymmetric divisions and increases the number of symmetric divisions. Importantly, as discussed in more detail herein, treatment with excess ICG-001 corrects the defect in asymmetric divisions caused by IQ-1, confirming that re-equilibration of increased symmetric (i.e. CBP/catenin dependent) divisions can be corrected with a CBP/catenin antagonist like ICG-001.

EXAMPLES

Example 1

CBP/β-catenin Antagonists were Shown to Stimulate Hair Growth and Increase Wound Healing in a Leukemia Mouse Model Overview:

According to particular aspects as described herein, CBP/β-catenin antagonists have surprisingly substantial utility for stimulating hair growth and/or preventing hair loss. Applicants tested the ability of CBP/β-catenin antagonists to sensitize drug resistant leukemia cells to treatment with standard chemotherapy. Unexpected results from this experiment demonstrated that the CBP/β-catenin antagonists stimulated hair growth in the leukemia mouse model. Additional surprising results were seen in the skin wounds of the mice in the experiment.

Materials and Methods:

NOD/SCIDIL2R gamma−/− mice were shaved and sub-lethally irradiated prior intravenous injection of 50,000 cells per animal. Leukemic animals were treated with a combination of intraperitoneally administered vincristine/dexamethasone/L-Aspariginase (VDL) and ICG-001 (50 mg/kg/d), which was delivered via subcutaneous osmotic pumps to ensure stable plasma levels, with VDL only as a control for 20 days. The animals were checked periodically for survival, hair growth, and wound healing.

Figure 11:
FIG. 11 is a photograph taken at day 47 of treatment of a leukemia mouse model with either vincristine/dexamethasone/L-Asparginase (VDL) alone or in combination with ICG-001 (a CBP/catenin (e.g., CBP/β-catenin) antagonist).

Results:

The surprising results can be seen in FIG. 11. Within two weeks the intraperitoneally administered ICG-001 (50 mg/kg/d), but not the VDL alone treatment, resulted in substantial hair growth covering the entire previously shaved area. In addition, the wounds that were induced while inserting the pump were found to heal quicker in the mice treated with ICG-001 when compared to the VDL only control.

Conclusions:

The surprising results discovered in this experiment, stimulation of hair growth and increased speed of healing, led the Applicants to test the ability of CBP/catenin (e.g., CBP/β-catenin) antagonists to increase healing in normal mice and hairless mouse models (EXAMPLE 2) and to stimulate hair growth in hairless mouse model (EXAMPLE 3).

Example 2

CBP/Catenin (e.g., CBP/β-catenin) Antagonists were Shown to Stimulate Wound Healing in Both Normal Mice and Hair-less Mice Models The ability of CBP/catenin (e.g., CBP/β-catenin) antagonist to accelerate injured skin repair in normal mice models (having full hair growth and normal fur) and hair-less mice models was tested. In brief, on day 0, the animals were subjected to skin injury in two spots on the back, hind end of each animal. Each skin injury spot was treated with 500 μM of either Vaseline (petrolatum) (vehicle) or Laura-8 in vaseline once a day for eight days.

Figure 12:
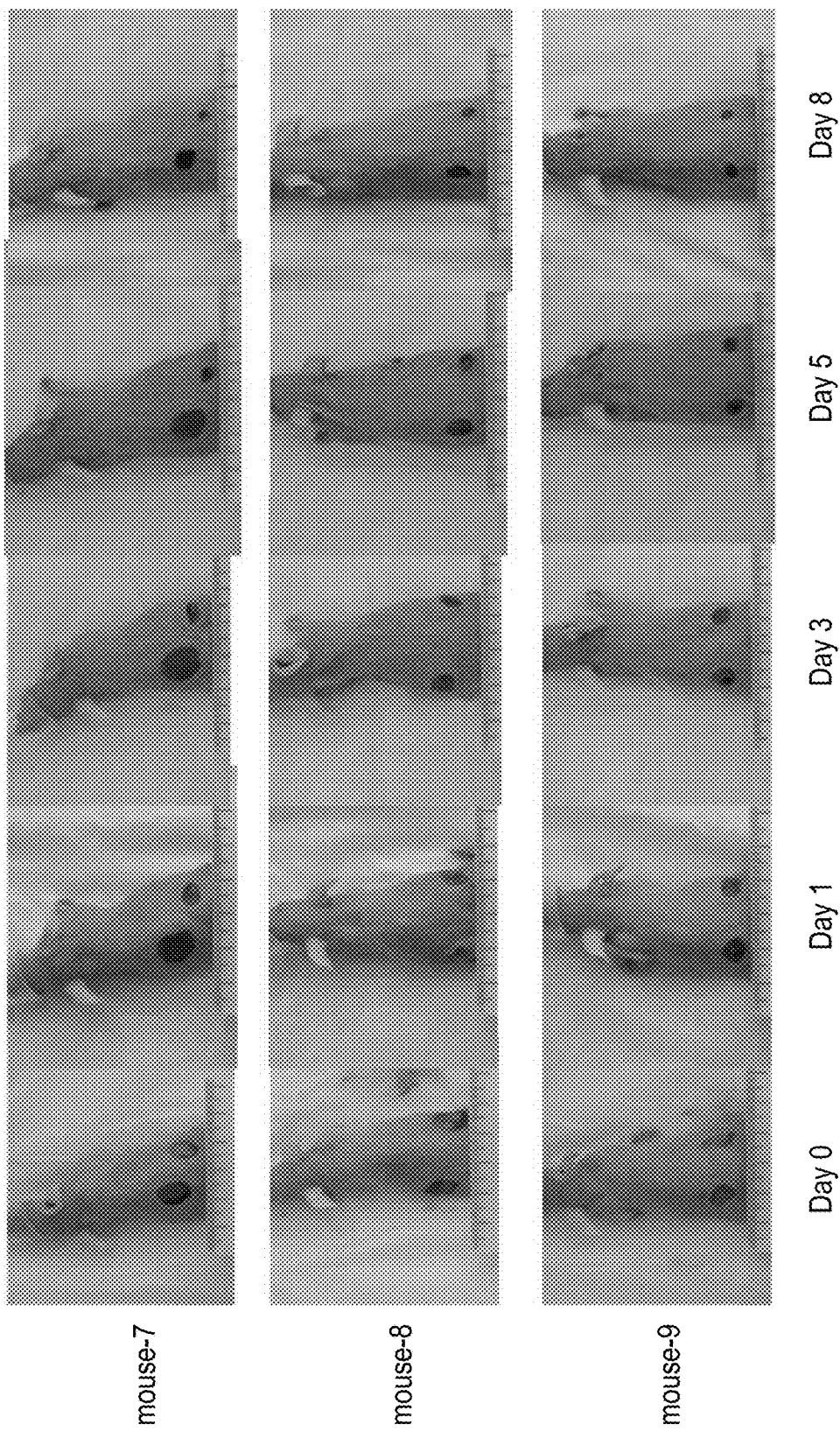
FIG. 12 is a series of photographs taken of three exemplary mice over an eight day time course (left flank wound is treated topically with petrolatum, right flank wound with petrolatum with 500 uM Laura8 a CBP/catenin antagonist).

As shown in FIG. 12, in both animal models, Laura-8 (a derivative of ICG-001), significantly accelerated skin healing process over the course of eight days.

Example 3

CBP/Catenin (e.g., CBP/β-catenin) Antagonists were Shown to Stimulate Hair Growth in a Hair-less Mouse Model The ability of CBP/β-catenin antagonist to stimulate hair growth in a hair-less mouse model was tested. In brief, the animals were treated with either petroleum jelly or Laura-8 for 16 days. In addition, skin samples from each animal were taken and examined for hair-follicle formulation.

Figure 13:
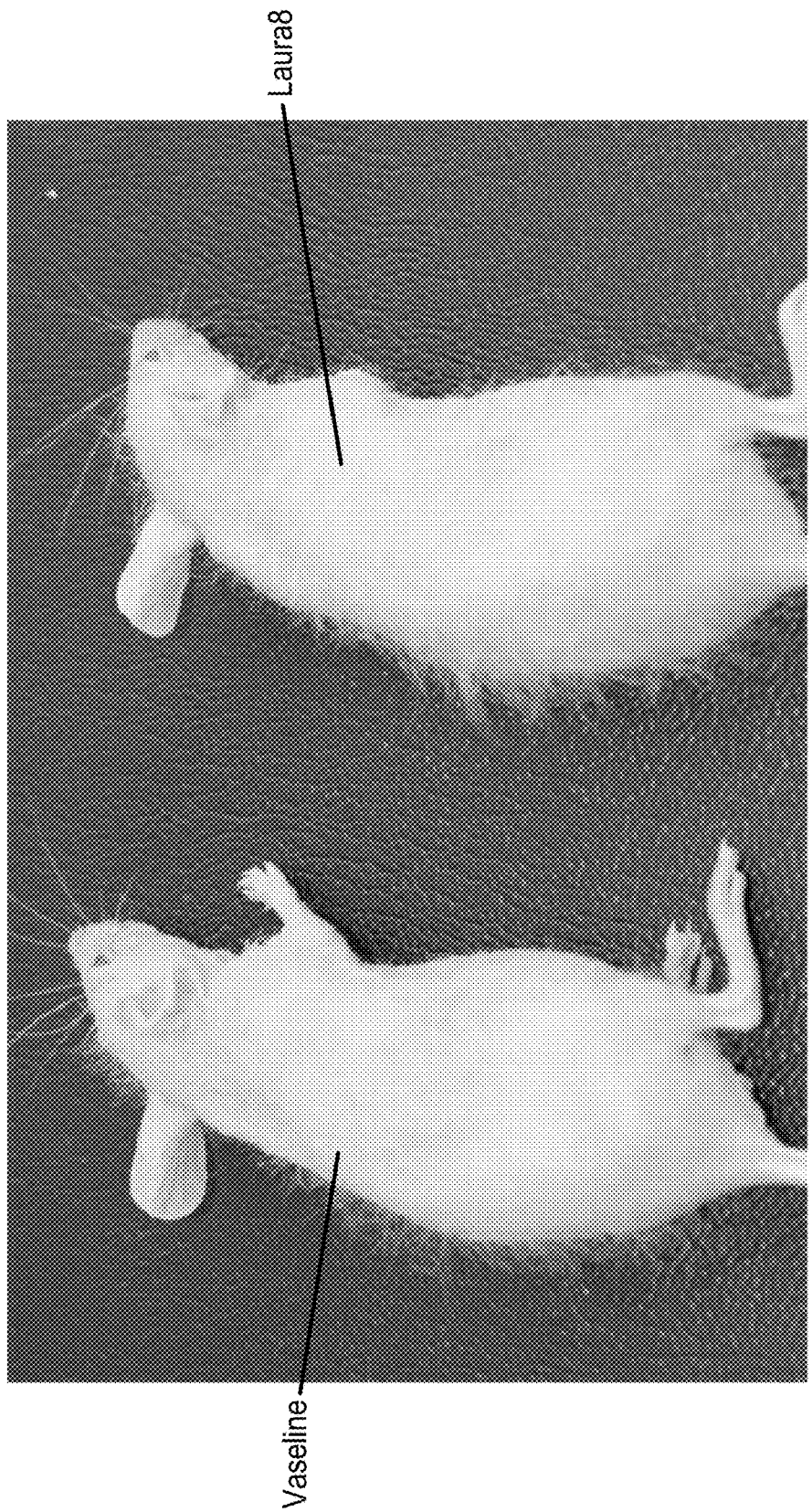
FIG. 13 is a photograph demonstrating the effects of CBP/catenin (e.g., CBP/β-catenin) antagonists in a hairless mouse model of alopecia. The mouse on the left was treated with Vaseline alone, whereas the mouse on the right was treated with Laura8 in Vaseline (petrolatum) (the laurate ester of ICG-001) (a CBP/catenin (e.g., CBP/β-catenin) antagonist).
Figure 14:
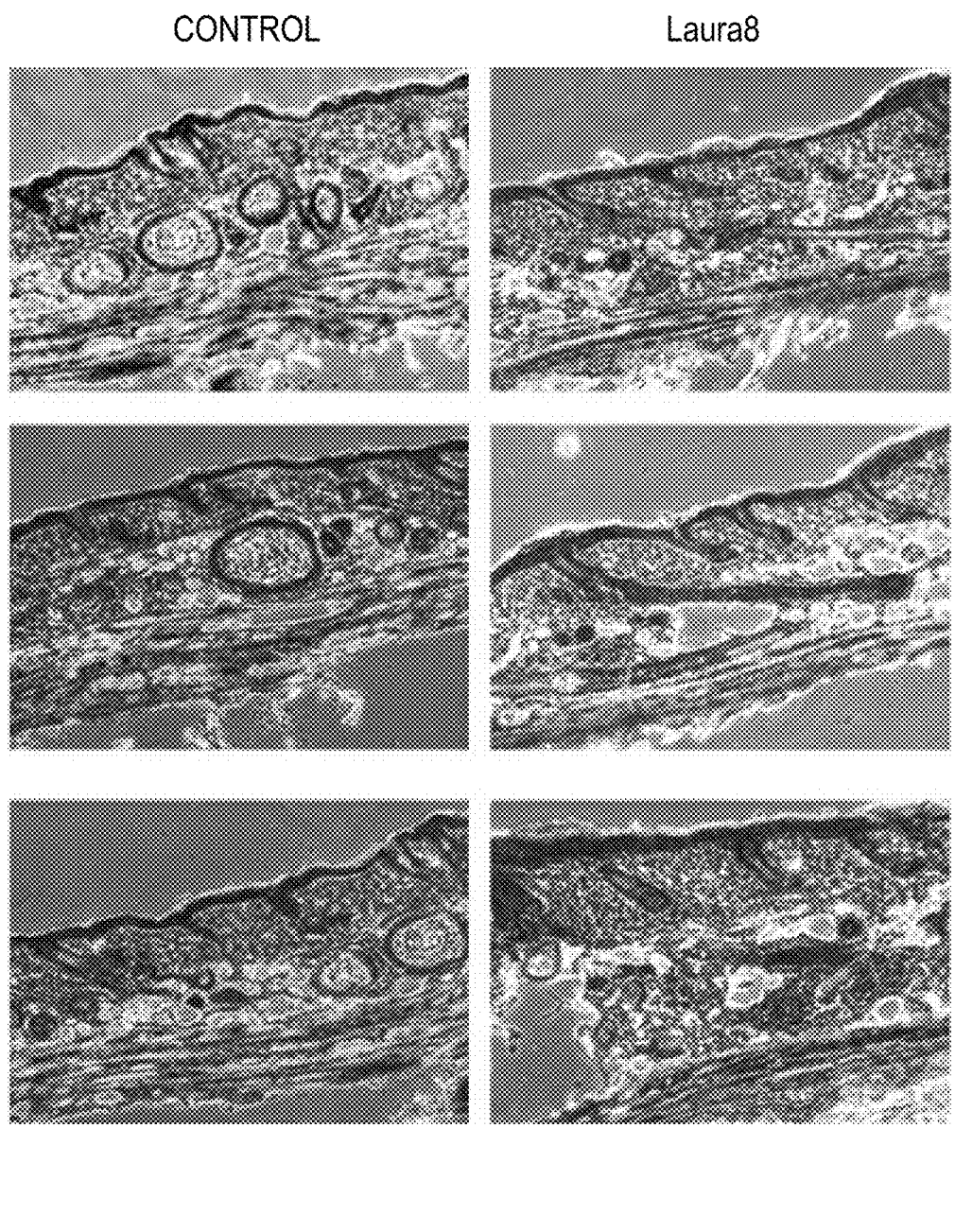
FIG. 14 is a series of photographs showing the effects of CBP/catenin (e.g., CBP/β-catenin) antagonists on the skin pathology of the mice in the hairless mouse model as shown in FIG. 13. These photographs demonstrate that new hair-follicles were formed in the Laura-8 (right side), but not the Vaseline control (left side) treated mice. Furthermore, due to a defect in a nuclear corepressor that is associated with this defect in hair growth, the hair follicle bulges proliferate symmetrically to form large cystic growths. Treatment with the CBP/catenin antagonist causes differentiation via increasing asymmetric divisions thereby causing new hair follicle formation.
Figure 15:
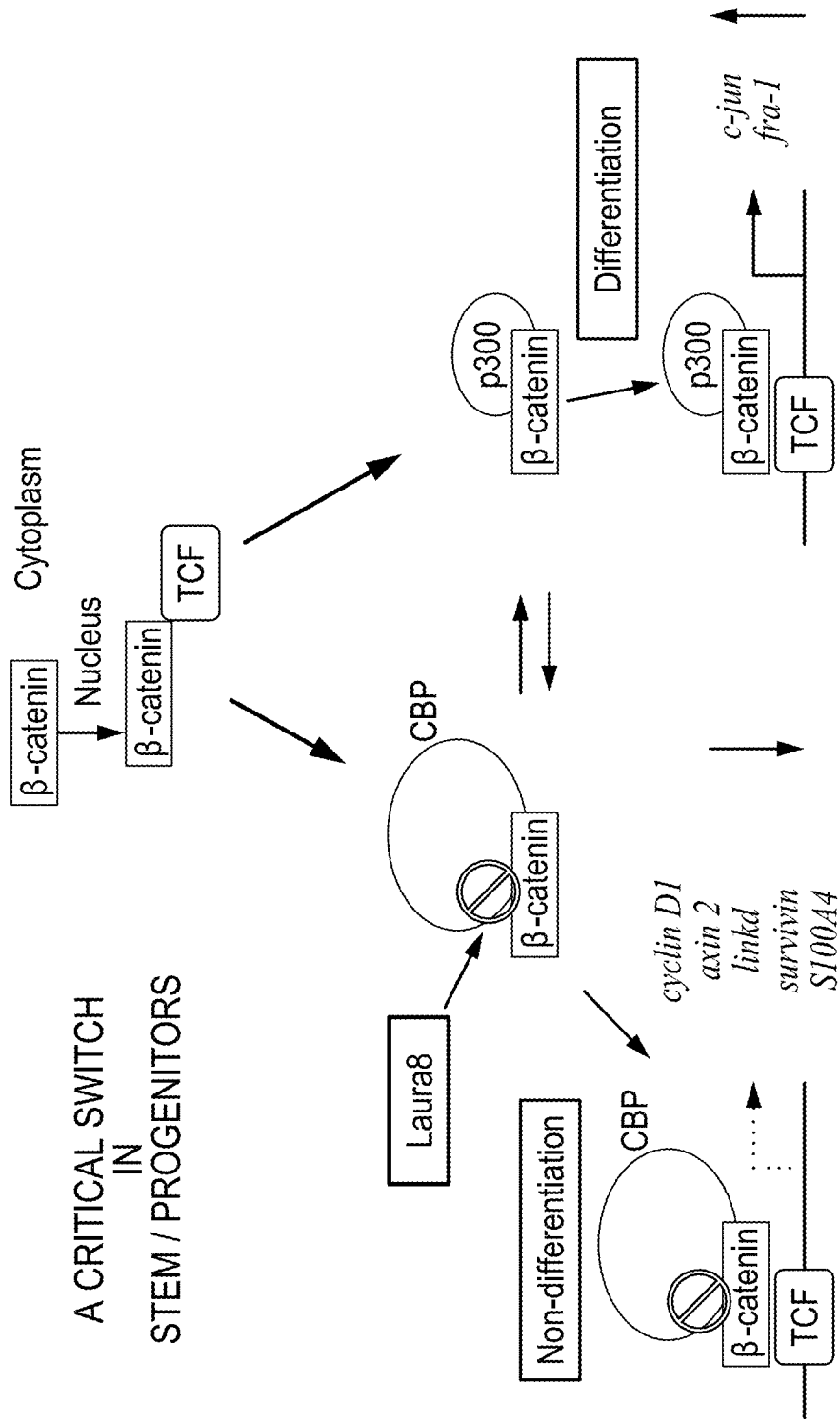
FIG. 15 is a schematic demonstrating the pathway that CBP/catenin (e.g., CBP/β-catenin) antagonists inhibit.
Figure 16:
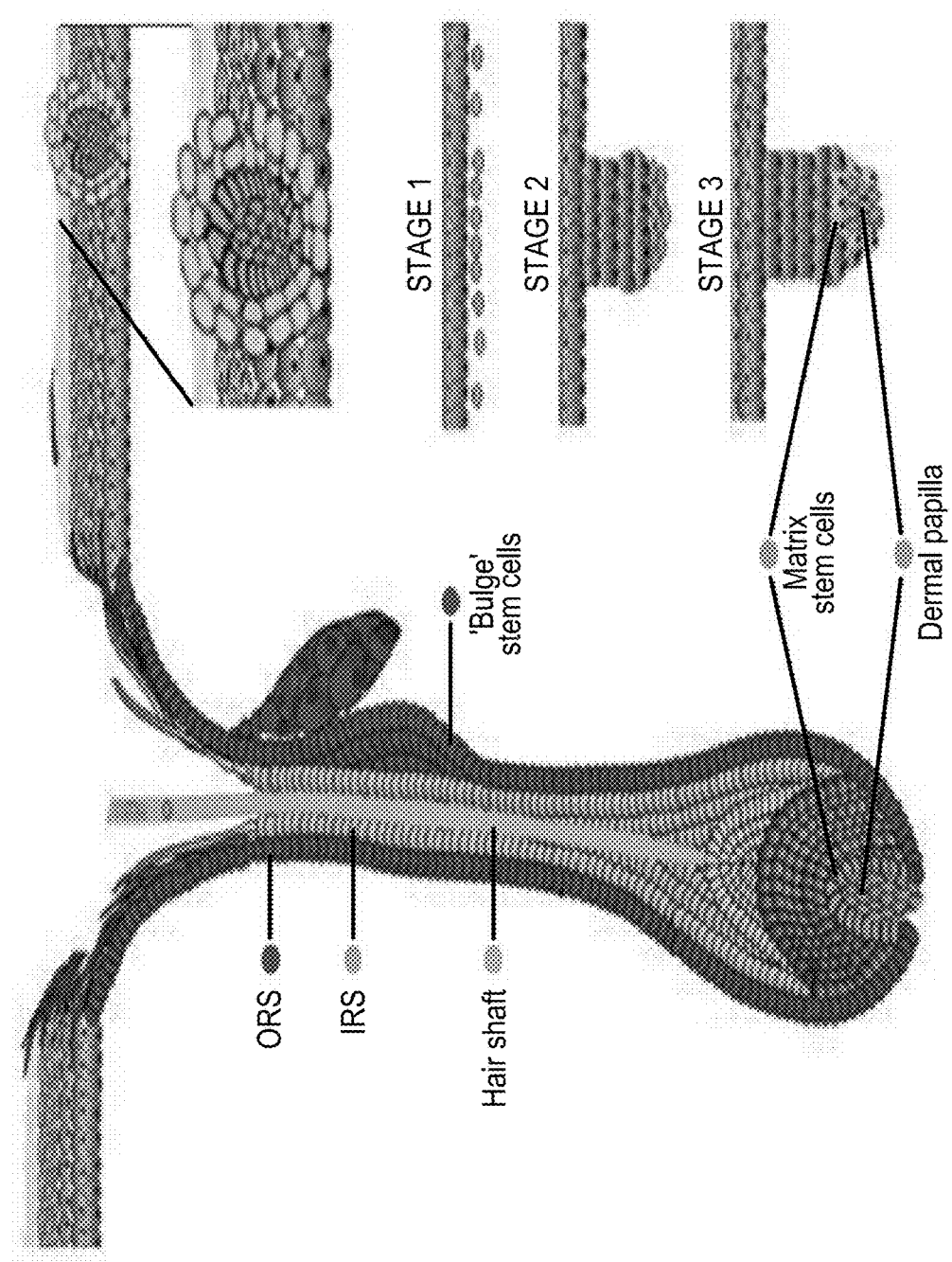
FIG. 16 is a schematic demonstrating a hair follicle and its formation.
Figure 17:
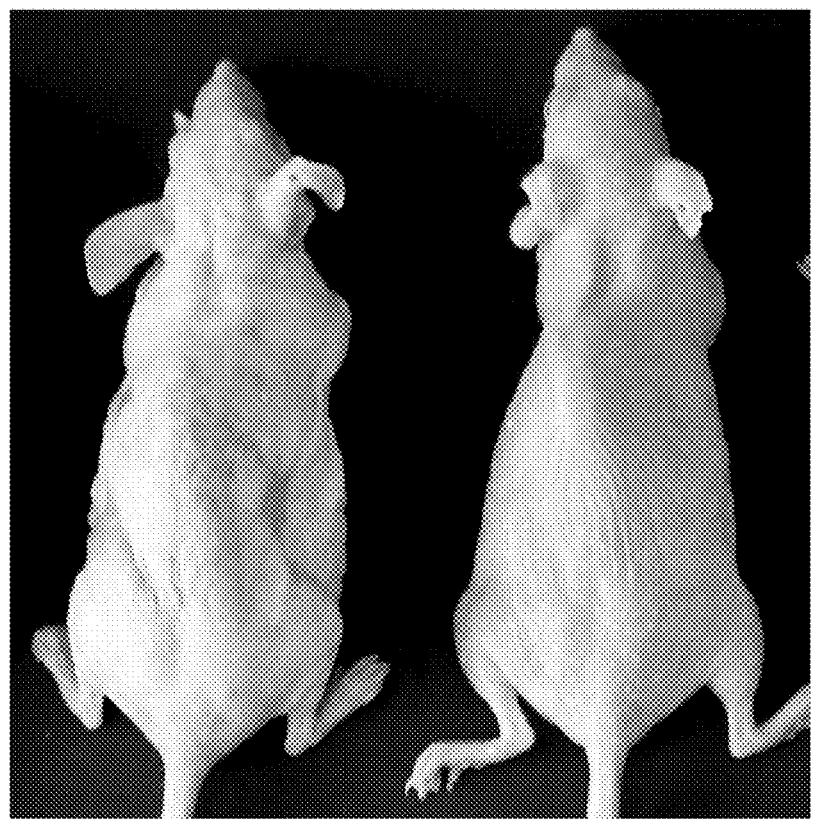
FIG. 17 shows aging mice. Left mouse is control, whereas right mouse received CBP/catenin (e.g., CBP/β-catenin) antagonists (topical Laura-8 as disclosed herein) for 12 months (from 6 months of age to 18 months of age). Importantly this proves that long term administration of a CBP/catenin antagonist does not deplete the normal stem cell niche as would be expected form an agent that induces asymmetric divisions in the normal stem cell niche thereby maintaining the normal stem cell population.

As shown in FIG. 13, the animals treated with Laura-8 resulted in significant hair growth over those treated with petroleum jelly, in this hair-less mouse model. FIG. 14 shows the skin pathology of the skin samples taken from the animals treated as described. This figure shows that there is substantial new hair-follicle formation in the Laura-8 treated mice, but not the petroleum jelly treated mice.

Example 4

CBP/Catenin (e.g., CBP/β-catenin) Antagonists Dramatically Increased the Expression of Adenosine Receptors Overview:

Minoxidil, the active ingredient in Rogaine, activity is mediated via the adenosine receptor in dermal papilla cells. Several adenosine receptors are expressed in dermal papilla cells (A1, A2A and A2B (Li M., J. Invest. Dermatol. 117, 1594-1600, 2001).

Applicants tested the ability of CBP/catenin antagonist to upregulate the expression of adenosine receptors.

Results:

Applicants conducted gene expression array experiments to demonstrate that treatment of cells in culture with a CBP/catenin antagonist (e.g., ICG-001; 10 uM) dramatically (~10x) increases the expression of adenosine receptors, e.g., in colonic epithelium Adenosine Receptor A2B (ADORA2B).

According to particular embodiments, therefore, administration of a CBP/catenin (e.g., CBP/β-catenin) antagonist with another hair stimulating agent (e.g., Minoxidil) provides a strong additive or synergistic effect in hair growth and/or regrowth when treating the scalp, e.g., topically with a CBP/catenin (e.g., CBP/β-catenin) antagonist to, for example, increase the expression of adenosine receptors and/or modulating the sulfonylurea receptor 2B believed to be the molecular target through which minoxidil works.

Example 5

Assay of ICG-001 and Methylated ICG-001 Compared to RA

According to particular aspects, Me-ICG-001 has substantial utility for the present invention.

Methods. Ex Vivo human skin assay culture conditions were based upon a paper by Varani J et al Experimental and Molecular Pathology, 2004.

Briefly, human skin (surgical waste from plastic surgery procedures) was obtained and the subcutaneous layer of fat was trimmed manually with a scalpel. The skin was then cut into small fragments about 2 mm square and placed in 6 well plates. 1 ml of keratinocyte culture medium (Gibco 10724-011) with 1% P/S (penstrep antibiotic) was added to each well. The epidermis, bathed in media was placed facing up. On the next day (overnight culture in the media above), the skin fragments were transferred to fresh wells that contained either 5 uM ICG-001, 5-uM methylated ICG-001 or 1 ug/ml of retinoic acid (RA). After 24 hrs, skin samples in culture were removed for RNA isolation and qRT-PCR analysis of genes of interest (e.g., elastin (a gene involved in skin appearance and pliability (e.g., wrinkling)) and aquaporin 1, which is involved with hydration.

Figure 18:
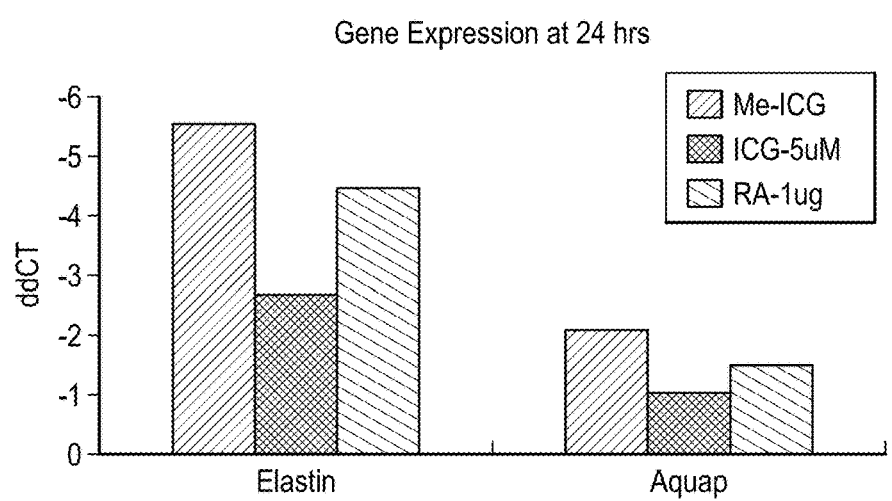
FIG. 18 shows treatment of human surgical waste skin as described herein. All compounds showed an increase in the expression of both elastin and aquaporin 1 with Me-ICG-001 showing a larger increase at 5 uM than either ICG-001 or RA.

Results. FIG. 18 shows treatment of human surgical waste skin as described herein.

All compounds showed an increase in the expression of both elastin and aquaporin 1 with Me-ICG-001 showing a larger increase at 5 uM than either ICG-001 or RA.

Example 6

Exemplary Adjunctive Therapies

According to particular aspects, the CBP/catenin (e.g., CBP/β-catenin) antagonists as disclosed herein have substantial utility for use in adjunctive therapy settings, including, but not limited to use with at least one of the following exemplary compositions and/or methods:

Use with at least one other hair growth stimulating agent is at least one selected from the group consisting of minoxidil, finasteride, dutasteride, bimatoprost and antiandrogen receptor blockers including fluridil.

Use with at least one anti-inflammatory agent is selected from the group consisting of: short-acting $\beta_2$-agonists, long-acting $\beta_2$-agonists, anticholinergics, corticosteroids, systemic corticosteroids, mast cell stabilizers, leukotriene modifiers, methylxanthines, $\beta_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, glucocorticoid steroids, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof.

Absorptive Dressing. Medipore (3M); Silon Dual-Dress 04P® Multi-Function Wound Dressing & Silon Dual-Dress 20F® Multi-Function Wound Dressing (Bio Med Sciences); Aquacel Hydrofiber CombiDERM (ConvaTec); Absorptive Border (DermaRite); MULTIPAD, SOF SORB (DeRoyal); IODOFLEX (HEALTHPOINT); TIELLE (Johnson & Johnson); CURITY ABD, TELFAMAX, TENDERSORB ABD (Kendall); Mepore (Molnlycke Health Care); EXU-DRY, Primapore (Smith & Nephew).

Alginates. AlgiCell (Dumex Medical); AlgiDERM (Bard); AlgiSite M (Smith & Nephew, Inc. Wound Management Division); Askina Sorg (Swiss-American); CarraSorb H, CarraGinate with Acemannan gel (Carrington); CURASORB, CURASORB Zinc (Kendall/Tyco); Dermacea (Sherwood—Davis & Geck); DermaGinate, DermaGinate AG (DermaRite); FyBron (B. Braun); Gentell (Gentell); Hyperion Advanced Alginate Dressing (Hyperion Medical, Inc.); KALTOSTAT (various presentations) (ConvaTec); KALGINATE, Algidex (various presentations)(DeRoyal); Maxorb (Medline); Melgisorb (Molnlycke Health Care); PolyMem (Ferris Mfg.); Restore CalciCare (Hollister); SILVERCELL (Johnson & Johnson); Sorbalgon (Harmann-Conco Inc.); SORBSAN (Mylan Bertek); SeaSorb (Coloplast Corp.); Tegagen H G, Tegagen H I (3M Health Care).

Antimicrobials. 3M Tegaderm Ag Mesh (3M); Amerigel (various presentations) (Amerx Health Care Corp); Anasept (Anacapa); Silverlon (Argentum Medical LLC); Di-Dak-Sol (Century Pharmaceuticals); Contreet (various presentations) (Coloplast Corp.); Aquacel Ag (ConvaTec); SilverDerm7 (DermaRite); Algidex (DeRoyal); ColActive Ag (Hartmann-Conco Inc.); Hydrofera Blue (Hydrofera Inc.); Actisorb (Johnson & Johnson); Kerlix AMD, Curity AMD, Excilon AMD, TELFA AMD (Kendall/Tyco); Arglase (various presentations), Maxorb Extra Ag, Optifoam AG, SilvaSorb (various presentations), XCell AM (Medline); SelectSilver (Milliken Company); Acticoat 3, Acticoat 7, Acticoat Moisture Control, IODOFLEX, IODOSORB (Smith & Nephew); Silver Seal (X-Static/Noble Biomaterials).

Cleansers. 3M Cavilon (3M); Wound Wash Saline (Blairex Labs); Clinical Care, Techni-Care (Care-Tech); Puri-Clens, Sea-Clens (Coloplast); Optipore Sponge, SAF-Clens, Shur-Clens (ConvaTec); Clean 'N Moist, Repair Wound Cleanser (Darja Laboratories Inc.); DermaKlenz (DermaRite); Dermagran (Derma Sciences); ALLCLENZ (HEALTHPOINT); Restore (Hollister); Hyperion Wound Cleanser (Hyperion Medical, Inc.); DEBRISAN (Johnson & Johnson); Constant-Clens (Kendall); Skin Tegrity (Medline); MPM, MPM Antimicrobial (MPM); Elta Dermal (Swiss-American Products).

Closure Devices. WoundTek's S.T.A.R. Device (Wound-Tek, Inc.); DP Woundcare Dressing (DP Wound Care); Dermabond (JnJ/Ethicon website); DermaClose RC (Woundcare Technologies).

Collagen. Medifil, Skin Temp (BioCore); BGC Matrix (Brennen); WOUN'DRESS (Coloplast Sween); Collagen/AG (DermaRite); ColActive Ag (Hartmann-Conco, Inc.); FIBRACOL plus Collagen Prisma, Promogran Prisma (Johnson & Johnson); Mepore Pro (Molnlycke); Stimulen (Southwest); Primatrix (TEI Biosciences); hyCURE, hyCURE Smart Gel (The Hymed Group); CellerateRx (Wound Care Innovations).

Compression Dressing & Wraps (Leg). 3M Coban 2 layer (3M); ArtAssist (ACI Medical); Gelocast Unna Boot, Artiflex, Comprilan, Tricofix (BSN); CIRCULON, DuoDERM SCB, Setopress, SurePress, UNNA-FLEX (ConvaTec); Primer, Unna-Pak (Glenwood, Inc.); 4-Layer Compression (Hartmann-Conco); DYNA-FLEX (Johnson & Johnson); TENDERWRAP (Kendall); Profore, Profore LF, Profore Lite (Smith & Nephew).

Composite Dressing. Tegaderm Transparent Dressing with Absorbent Pad (3M); Silon Dual-Dress 04P® Multi-Function Wound Dressing & Silon Dual-Dress 20F® Multi-Function Wound Dressing (Bio Med Sciences); Coverlet (BSN); COVADERM (DeRoyal); TELFA, VENTEX (Kendall); StrataSorb (Medline); Alldress (Molnlycke Health Care); MPM (MPM); Viasorb (Sherwood-Davis & Geck); AIRSTRIP, Coverlet, CovRSite Plus, Cutifilm, OpSite Plus, OpSite Post-Op (Smith & Nephew); Centurion SorbaView (Tri-State Hospital Supply).

Contact Layer. Tegapore (3M); Silon-TSR® Temporary Skin Replacement (Bio Med Sciences); DERMANET (DeRoyal); TELFA CLEAR (Kendall); Mepitel (Molnlycke Health Care) Profore Wound Contact Layer (Smith & Nephew); N-TERFACE (Winfield Laboratories).

Enzymatic Debriders. Accuzyme, Panafil, Collagenase (HEALTHPOINT); Ethezyme™ 830 Papain Urea Debriding Ointment (Ethex); Ethezyme™ Papain-Urea Debriding Ointment (Ethex); Kovia Ointment, Ziox Ointment (Stratus Pharmaceutical); Gladase (Smith & Nephew).

Fillers (Wound). AcryDerm Strands (AcryMed); DermAssist (AssisTec); Cutinova Cavity (Beiersdorf-Jobst); Humatrix Microclysmic Gel (Care-Tech); Mesalt (Molnlycke Health Care); MULTIDEX (DeRoyal); PolyWic (Ferris Mfg.); BIAFINE (Medix).

Foam Dressings. 3M Foam Dressing (nonadhesive), 3M Foam Adhesive Dressing (3M); Vigi-FOAM (Bard), FLEX-ZAN (Bertek (Dow Hickam)); Silon Dual-Dress 20F® Multi-Function Wound Dressing (Bio Med Sciences); Lyofoam, Lyofoam A, Lyofoam C, Lyofoam Extra, Lyofoam T (ConvaTec); POLYDERM (DeRoyal); PolyMem (Ferris Mfg.); Hydrofera Blue (Hydrofera LLC); BIOPATCH (Johnson & Johnson); CURAFOAM (Kendall); Mepilex, Mepilex Border, Mitraflex, Mitraflex Plus (Molnlycke Health Care); Allevyn Adhesive, Allevyn Cavity, Allevyn Dressing, Allevyn Island, Allevyn Tracheostomy, Allevyn Sacral (Smith & Nephew).

Hydrocolloid. Tegasorb, Tegasorb THIN (3M); Hydrocol (Bertek (Dow Hickam)); BGC Matrix (Brennen); Comfeel (multiple presentations) (Coloplast); DuoDERM CGF, DuoDERM (multiple presentations), SignaDRESS Sterile (ConvaTec); DermaFilm HD, DermaFilm Thin (DermaRite); Restore (multiple presentations) (Hollister); NU-DERM (Johnson & Johnson); Ultec (Kendall); ExuDERM (multiple presentations) (Medline); RepliCare (multiple presentations), Cutinova Hydro, Cutinova Thin (Smith & Nephew).

Hydrofiber. AQUACEL (ConvaTec).

Hydrogel. Tegagel (3M); Amerigel Topical Ointment (Amerx Health Care); Bard Absorption Dressing, Biolex, Iamin (Bard Medical); CarraSorb, Carrasyn, DIAB GEL (Carrington Laboratories); Woun'Dres, Purilon (Coloplast); DuoDERM, SAF-Gel (ConvaTec); Repair Hydrogel (Darja Laboratories Inc.); DermaSyn (DermaRite); Dermagran (Derma Sciences, Inc.); CURASOL (HEALTHPOINT); Restore (Hollister Inc.); NU-GEL (Johnson & Johnson); CURAFIL (Kendall); SkinTegrity (Medline); Hypergel, Normlgel (Molnlycke Health Care), MPM (MPM Medical, Inc.); Iamin (ProCyte); PanoPlex (Sage Laboratories); IntraSite, SoloSite (Smith & Nephew); Elta Dermal (Swiss-American Products, Inc.).

Hydrogel Impregnated Gauze. DermAssist (AssisTec Medical, Inc.); Biolex (Bard); CarraGauze (Carrington); ClearSite (Conmed Corp.); DermaGauze (DermaRite); Dermagran (Derma Sciences); Gentell (Gentell); CURASOL (HEALTHPOINT); Restore (Hollister); Hyperion Hydrophilic Wound Dressings (Hyperion Medical, Inc.); INTEGRA-GEL (Integrity Medical Devices, Inc.); CURAFIL (Kendall); SkinTegrity (Medline Industries); Normlgel Impregnated Gauze (Molnlycke Health Care); MPM Conductive Gel Pad, MPM GelPad (MPM); PanoGauze (Sage); SoloSite Gel Conformable (Smith & Nephew); Elta Dermal (Swiss-American Products, Inc.).

Hydrogel Sheet. Tegagel (3M); Vigilon (Bard); ClearSite (Conmed Corporation); AQUASORB (DeRoyal); FLEX-DERM (Bertek (Dow Hickam)); NU-GEL (Johnson & Johnson); CURAGEL (Kendall); Derma-Gel (Medline Industries); FlexiGel (Smith & Nephew).

Measuring Devices. (Molnlycke Health Care); Tru-Area Determination (NTL).

Miscellaneous Devices. EPIFLO—Transdermal sustained delivery of oxygen (Ogenix website); Circulator Boot (Circulator Boot Corporation website).

Negative Pressure Wound Therapy. Engenex (Boehringer Wound Systems, LLC website); Prospera PRO-I (Medica-Rents, Inc., website); V.A.C. (various models)(KCI website); Versatile 1, VISTA (Smith & Nephew); Invia (Medela).

Odor Absorbing. CarboFlex, LyoFoam C (ConvaTec); Odor Absorbing Dressing (Dumex).

Scar Therapy and Makeup. Oleeva (various), Silon (Bio Med Sciences); Mepiform (Molnlycke); Cica-Care (Smith & Nephew); Various (Local Pharmacy).

Skin Care

For patients with wounds or patients at risk of skin breakdown, some exemplary categories include: antifungals, anti-inflammatory, barriers, moisturizers, and sealants.

Skin Substitutes. Dermagraft, Transcyte (Advanced Biohealing); Hyalofil-F, Hyalofil-R (ConvaTec); Integra (various presentations) (Integra LifeSciences); Alloderm (Lifecell); Biobrane (Mylan Bertek); Apligraf (Organogenesis); Primatrix (TEI Biosciences).

Tissue Engineering/Growth Factors. Apligraf (Organogenesis website); Dermagraft, Transcyte (Advanced Biohealing website); GRAFTJACKET® Regenerative Tissue Matrix Ulcer Repair (Wright Medical Technologies, Inc., website); GRAFTJACKET® XPRESS Flowable Soft-Tissue Scaffold (Wright Medical Technologies, Inc., website); Oasis (Healthpoint website); Orcel (Ortec International, Inc., website); Regranex (Johnson & Johnson website).

Transparent Films. Tegaderm HP, Tegaderm (3M); Silon-TSR® Temporary Skin Replacement (Bio Med Sciences); CarraFilm (Carrington); DermaView (DermaRite); TRANSEAL (DeRoyal); BIOCLUSIVE MVP, BIOCLUSIVE (Johnson & Johnson); Blisterfilm, POLYSKIN II, POLYSKIN M.R. (Kendall); SureSite (Medline); Mefilm (Molnlycke Health Care); ProCyte (ProCyte); OpSite FLEXIGRID, OpSite, UniFlex (Smith & Nephew).

Incorporation by Reference

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

It should be understood that the drawings and detailed description herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the following claims. Thus, it is intended that the following claims be interpreted to embrace all such further modifications, changes, rearrangements, substitutions, alternatives, design choices, and embodiments.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method for treating aging or an age-related condition, symptom or disease of the skin, comprising:
    identifying a mammalian subject having somatic stem cells for least one tissue compartment or type having an age-related skin condition, symptom or disease selected from the group consisting of wrinkles, hyperpigmentation, redness, rosacea, dryness, cracking, loss of firmness, loss of elasticity, thinning, loss of vibrance, wounds, scars, fibrosis, acne, sun damage, ulcers including diabetic ulcers, burns, atopic dermatitis, psoriasis, reduced cuticle/nail growth, and hair loss or loss of hair coloration; and
    administering to the subject a CBP/catenin antagonist in an amount sufficient for increasing the number of asymmetric renewing divisions relative to, or at the expense of symmetric divisions of the somatic stem cells for the at least one tissue compartment or type, wherein the age related condition, symptom or disease of the tissue compartment or type is decreased or ameliorated, wherein the CBP/catenin antagonist is selected from the Formula (I) and Formula (II) compound group consisting of:

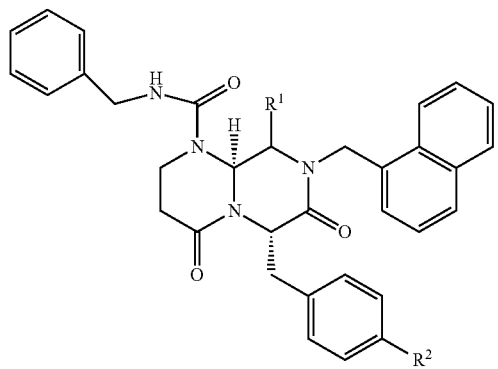

(I)

wherein $R^1$ is selected from hydrogen or C1-C6 alkyl, and wherein $R^2$ is selected from —OH or —O(CO)(CH$_2$)$_n$CH$_3$, wherein n is a value from 0 to 34, and provided that where $R^1$ is hydrogen, $R^2$ cannot be —OH; or a or a pharmaceutically acceptable salt thereof;
    the compound of Formula (I), wherein $R^1$ is selected from C1-C6 alkyl, and wherein $R^2$ is selected from —OH or —O(CO)(CH$_2$)$_n$CH$_3$, wherein n is a value from 0 to 34;

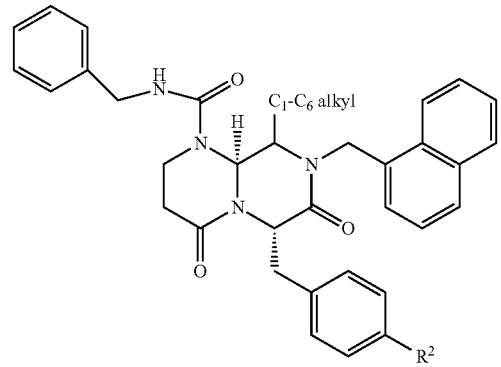

(II)

wherein $R^2$ is selected from —OH or —O(CO)(CH$_2$)$_n$CH$_3$, wherein n is a value from 0 to 34;
    the compound of Formula (II), wherein $R^1$ is —CH$_3$, and $R^2$ is —OH;
        the compound of Formula (II), wherein $R^1$ is —CH$_3$, and $R^2$ is selected from —O(CO)(CH$_2$)$_n$CH$_3$, wherein n is a value from 0 to 34; and
        the compound of Formula (II), wherein n is 10, where the compound is 4-(((6S,9S)-1-(benzylcarbamoyl)-9-methyl-8-(naphthalen-1-ylmethyl)-4,7-dioxooctahydro-1H-pyrazino[1,2-a]pyrimidin-6-yl)methyl)phenyl dodecanoate.

2. The method of claim 1, wherein the somatic stem cells for the at least one tissue compartment or type comprise quiescent somatic stem cells, and wherein administering the CBP/catenin antagonist comprises CBP/catenin antagonist-mediated activation of the quiescent somatic stem cells to enhance or accelerate asymmetric renewing divisions relative to, or at the expense of symmetric divisions among the somatic stem cells of the at least one tissue compartment or type.

3. The method of claim 1, wherein the somatic stem cells comprise at least one selected from the stem cell group consisting of skin including keratinocyte stem cells, epidermal, follicular, hematopoietic, mammary, intestinal epithelium including crypt cells, mesenchymal including muscle satellite cells, melanocyte stem cells, osteoblasts and chondrocyte progenitors, endothelial, neural, including either the ependymal or the subventricular zone cells, neural crest, olfactory, testicular, uterine, and cuticle stem cells.

4. The method of claim 1, wherein the somatic stem cells for the at least one tissue compartment or type, comprise hair follicle stem cells of a skin tissue compartment, and wherein increased hair growth, regrowth, or increased hair pigmentation is provided at the skin tissue compartment or type, preferably at the scalp or eye lid tissue compartment or type.

5. The method of claim 4, wherein the CBP/catenin antagonist is present in an amount sufficient to modulate or increase the expression of an A1, A2A, or A2B adenosine receptor in dermal cells, preferably dermal papilla cells.

6. The method of claim 4, wherein the CBP/catenin antagonist is present in an amount sufficient to modulate or increase the expression of sulfonylurea receptor 2B in dermal cells, preferably dermal papilla cells.

7. The method of claim 4, comprising co-administration of or adjunct treatment with at least one other hair growth stimulating agent, or hair loss preventing agent.

8. The method of claim 7, wherein the at least one other hair growth stimulating agent is at least one selected from the group consisting of minoxidil, finasteride, dutasteride, bimatoprost and antiandrogen receptor blockers including fluridil.

9. The method of claim 4, comprising at least one of hair growth, regrowth, thickening, lengthening and pigmentation.

10. The method of claim 1, wherein the somatic stem cells for the at least one tissue compartment or type, comprise skin stem cells of a skin tissue compartment or type, and wherein enhanced skin repair and/or homeostatic maintenance is provided at the skin tissue compartment or type.

11. The method of claim 10, comprising decreasing scarring in a wound to a surface tissue.

12. The method of claim 10, comprising accelerating epidermal or dermal layering.

13. The method of claim 10, comprising increasing cellular migration of at least one type of cell to the wound.

14. The method of claim 13, wherein the type of cellular migration or proliferation comprises at least one cell selected from the group consisting of: keratinocytes, fibroblasts, epidermal cells, dermal cells, epithelial cells, mast cells, neutrophils, lymphocytes, and macrophages.

15. The method of claim 10, comprising accelerating neoangiogenesis of blood vessels or lymphatic vessels.

16. The method of claim 10, comprising increasing collagen deposition at the wound.

17. The method of claim 10, wherein the wound is at least one wound type selected from the group consisting of lacerations, abrasions, rupture, puncture wounds, chemical, thermal, or radiation-induced burns, cuts, scrapes, incisions, blisters, diabetic ulcers, bedsores or pressure ulcers, skin grafts, and surgical wounds.

18. The method of claim 1, wherein administration of the CBP/β-catenin antagonist comprises at least of one topical, gingival, buccal, labial, vaginal, sub cutaneous, and oral administration routes.

19. The method of claim 1, comprising cosmetically treating a condition of the skin or at least one symptom thereof.

* * * * *